United States Patent
Seio et al.

(10) Patent No.: US 6,455,521 B1
(45) Date of Patent: Sep. 24, 2002

(54) CONDENSED THIOPHENE COMPOUNDS AND PHARMACEUTICAL USE THEREOF

(75) Inventors: Koji Seio; Hiroshi Tanaka; Toshiyuki Kohara; Kenji Hashimoto; Masatake Fujimura; Hideki Horiuchi, all of Iruma; Hiroshi Yasumatsu; Koreichi Kimura, both of Fukuoka, all of (JP)

(73) Assignee: Mitsubishi Pharma Corporation, Osaka (JP)

( * ) Notice: Subject to any disclaimer, the term of this patent is extended or adjusted under 35 U.S.C. 154(b) by 0 days.

(21) Appl. No.: 09/837,424

(22) Filed: Apr. 19, 2001

Related U.S. Application Data

(62) Division of application No. 09/341,317, filed on Jul. 8, 1999, now Pat. No. 6,271,225.

(30) Foreign Application Priority Data

| Sep. 2, 1997 | (JP) | 9-236700 |
| Oct. 9, 1997 | (JP) | 9-277771 |
| Jun. 12, 1998 | (JP) | 10-165725 |

(51) Int. Cl.[7] .................. A61K 31/55; C07D 409/00; C07D 241/00; C07D 223/18; C07D 281/10
(52) U.S. Cl. .................. 514/218; 514/219; 514/212.03; 514/217.03; 544/358; 544/359; 544/374; 540/485; 540/526; 540/527
(58) Field of Search .................. 540/485, 526, 540/527; 544/358, 374; 514/212.03, 217.03, 218

(56) References Cited

U.S. PATENT DOCUMENTS

| 3,474,099 A | | 10/1969 | Renz et al. | 260/268 |
| 3,546,226 A | | 12/1970 | Schmutz et al. | 260/268 |
| 3,683,084 A | | 8/1972 | Schmutz et al. | 424/250 |
| 3,726,977 A | | 4/1973 | Schmutz et al. | 424/250 |
| 3,962,248 A | * | 6/1976 | Josef | 260/268 |
| 4,115,568 A | | 9/1978 | Chakrabarti et al. | 424/250 |
| 4,115,574 A | | 9/1978 | Chakrabarti et al. | 424/250 |
| 4,157,444 A | | 6/1979 | Press et al. | 544/359 |
| 4,172,831 A | | 10/1979 | Chakrabarti et al. | 260/239.3 |

FOREIGN PATENT DOCUMENTS

| DE | 2 552 403 | 8/1976 |
| EP | 0 454 436 | 10/1991 |
| GB | 1 533 235 | 11/1974 |
| GB | 1 533 236 | 11/1974 |
| WO | 95/17400 | 6/1995 |
| WO | 96/18621 | 6/1996 |
| WO | 96/18622 | 6/1996 |
| WO | 96/18623 | 6/1996 |
| WO | 96/18629 | 6/1996 |
| WO | 96/18630 | 6/1996 |
| WO | 96/19479 | 6/1996 |

OTHER PUBLICATIONS

J. Chakrabarti et al., "Effects of conformationally restricted 4-piperazinyl-10H-thienobenzodiazepine neuroleptics on central dopaminergic and cholinergic systems", J. Med. Chem. 1982, vol. 25, No. 10, pp. 1133–1140.

I. Laimer et al., "Studies on the chemistry of thienoanellated O,N- and S,N-containing heterocycles, 6[1]. Synthesis of some thienoanellated [1,4]benzoxazepines", J. Het. Chem. 31, pp. 1053–1059, 1994.

J. Chakrabarti et al., "4-piperazinyl-10H-thieno[2,3-b][1,5] benzodiazepines as potential neuroleptics[1]", J. Med. Chem. 1980, vol. 23, No. 10, pp. 878–884.

* cited by examiner

Primary Examiner—Mukund J. Shah
Assistant Examiner—Sudhaker B. Patel
(74) Attorney, Agent, or Firm—Wenderoth, Lind & Ponack, L.L.P.

(57) ABSTRACT

A condensed thiophene compound of the formula (I)

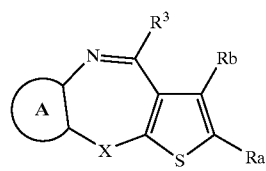

(I)

wherein each symbol is as defined in the specification, a pharmaceutically acceptable salt thereof and hydrates thereof. The compound of the formula (I) of the present invention is useful as a novel antipsychotic agent which is effective for both positive symptoms and negative symptoms of schizophrenia, which is associated with less side effects such as extrapyramidal motor disorder and the like and which is less associated with serious side effects such as agranulocytosis and the like. In addition, this compound is also useful as a therapeutic agent of Alzheimer's disease and manic-depressive illness.

16 Claims, No Drawings

CONDENSED THIOPHENE COMPOUNDS AND PHARMACEUTICAL USE THEREOF

This application is a Div of U.S. application Ser. No. 09/341,317 filed Jul. 8, 1999, now U.S. Pat. No. 6,271,225.

TECHNICAL FIELD

The present invention relates to condensed thiophene compounds useful for the treatment of schizophrenia, Alzheimer's disease, manic-depressive illness and the like, pharmaceutical use thereof and a synthetic intermediate thereof.

BACKGROUND ART

Schizophrenia is a mental illness having a high incidence of about 1% of the entire population. In most cases, convalescence is inferior and patients and their families are forced to suffer from a great burden over a long period of time. To avoid this, many studies have been done as to the etiology of schizophrenia, development of therapeutic drugs thereof and the like.

The first hypothesis proposed on the etiology of schizophrenia was an excess dopamine hypothesis. Based on this hypothesis, various compounds having a dopamine receptor inhibitory action have been developed as antipsychotic agents and achieved certain therapeutic effects.

The conditions of schizophrenia include positive symptoms mainly showing delusion, hallucination and the like, negative symptoms mainly showing social withdrawal, emotional torpor and the like, recognition function disorder such as defects of memory, learning disability and the like, and the like. A so-called typical antipsychotic agent centering on inhibition of dopamine receptor is comparatively effective on positive symptoms but ineffective against negative symptoms and recognition function disorders. When a typical antipsychotic agent is used, extrapyramidal side effects (e.g., dystonia, akathisia, delayed dyskinesia and the like) are inevitably caused by the dopamine receptor inhibitory action. These difficulties suggest a limit on the development of antipsychotic agent based solely on a so-called excess dopamine hypothesis.

In an attempt to solve the above-mentioned problems, antipsychotic agents, namely, serotonin-dopamine antagonist (SDA), having a serotonin receptor inhibitory action as a main action, have been studied and developed instead of dopamine receptor inhibitory action. Representative antipsychotic agents of SDA include risperidone, Seroquel and the like. However, the problems of poor effectiveness against negative symptoms and recognition function disorder or extrapyramidal side effects have not been entirely overcome [American Journal of Psychiatry 151, 825 (1994)].

One of the etiologic hypotheses of schizophrenia that have overtaken the excess dopamine hypothesis and the serotonin/dopamine hypothesis is a functional depression of glutamic acid nerve hypothesis [Trends in Neuroscience 13, 272 (1990)]. This hypothesis has been supported by the facts that (1) phencyclidine (PCP) which is an inhibitor of NMDA (N-methyl-D-aspartic acid) receptor induces mental conditions in human that are similar to schizophrenia with positive symptoms and negative symptoms [American Journal of Psychiatry 135, 1081 (1978), ibid. 148, 1301 (1991)], (2) cerebral cortex of schizophrenia patients shows lower reactivity of glutamic acid nervous system [Neuroscience Letters 121, 77 (1991)], (3) the number of NMDA receptors also present in the glutamic acid nervous system shows compensatory increase [Life Science 55, 1683 (1994)], (4) NMDA receptor agonists, such as glycine, D-cycloserine and the like, are effective for ameliorating the negative symptoms of schizophrenia [British Journal of Psychiatry 169, 610 (1996), American Journal of Psychiatry 152, 1213 (1995), ibid. 151, 1234 (1994)], and the like.

Clozapine and olanzapine are atypical antipsychotic agents characterized by their effectiveness against positive symptoms as well as negative symptoms of schizophrenia [Psychopharmacology 63,51 (1992), Neuropsychopharmacology 14, 111(1996)]. These atypical antipsychotic agents suppress abnormal behaviors induced in test animals [Psychopharmacology 120, 67 (1995), ibid, 129, 79 (1997), Pharmacology, Biochemistry and Behavior 47, 579 (1994)] and abnormal physiological function [Psychopharmacology 111, 339 (1993), Journal of Pharmacology and Experimental Therapeutics 271, 787 (1994)] by the functional depression of the glutamic acid nervous system by NMDA receptor inhibitors such as PCP and MK-801 (dizocilpine maleate), and their inhibitory capability is frequently stronger than that of typical antipsychotic agents. In other words, the superior clinical effects of the atypical antipsychotic agent may be ascribed to amelioration of functional depression of glutamic acid nervous system in addition to conventional dopamnine receptor inhibitory action and serotonin receptor inhibitory action.

The neurophysiological function abnormalities induced by an NMDA receptor inhibitor includes NMDA receptor inhibitor-induced neurotoxicity [Archive of General Psychiatry 52, 998 (1995)], and MK-801-induced neurotoxicity has been studied profoundly. This neurotoxic action can be inhibited by varioius antipsychotic agents, wherein the inhibitory action is stronger in clozapine and olanzapine that are atypical antipsychotic agents than in haloperidol and the like that are typical antipsychotic agents [Schizophrenia Research 15, 57 (1995), ibid. 21, 33 (1996)]. Using this MK-801-induced neurotoxic action as an index, an antipsychotic agent having an ameliorating action of functional depression of glutamic acid nervous system, that is one of the characteristics of clozapine and olanzapine, can be screened for. In addition, an MK-801-induced neurotoxic action is also considered a model of recognition function disorder observed in various diseases such as Alzheimer's disease and the like [Brain Research—Brain Research Reviews, 20, 250–267 (1995)], and a compound capable of inhibiting this neurotoxicity is also effective as a therapeutic drug of Alzheimer's disease, manic-depressive illness and the like.

Meanwhile, the use of clozapine is limited, since it induces serious agranulocytosis, thougn it also shows superior antipsychotic action [New England Journal of Medicine 324, 746 (1991)]. Reduction of the possibility of side effects is also an important aspect in developing an antipsychotic agent. A report has been recently documented that a cation radical generated as a metabolitic intermediate of clozapine may be involved in the mechanism of onset of agranulocytosis [CNS-Drugs 7, 139 (1997)]. It is significant, therefore, to inhibit generation of cation radical to avoid the onset of agranulocytosis.

Heretofore, there are various reports on suitable modification of the chemical structures of clozapine and olanzapine. For example, WO95/17400, WO96/18621, WO96/18623, WO96/18629, WO96/18630 and WO96/19479 disclose dibenzoxazepine compound, Japanese Patent Examined Publication Nos. 42-24513, 42-24514, 43-27404, 45-20909, 45-6822, 46-29861, 48-34599 and 49-40236, and Japanese Patent Unexamined Publication No. 47-4425 disclose dibenzoxazepine or dibenzothiazepine compound, WO93/07143 discloses pyridobenzoxazepine compound, Journal of Heterocyclic Chemistry 31, 1053 (1994) discloses thienobenzoxazepine compound, and Japanese Patent Unexamined Publication No. 63-8378 discloses dibenzothiazapine compound.

In addition, benzothiophene compound is disclosed in, for example, Japanese Patent Unexamined Publication Nos. 52-87196 and 51-76296 with regard to 1,2,3,4-tetrahydrobenzothieno[2,3-b][1,5]benzodiazepine derivative.

However, these compounds have remotely overcome the problems of effectiveness against negative symptoms and recognition function disorder, extrapyramidal side effects and the like, and activation of function of glutamic acid nervous system of the compounds of clozapine and olanzapine having suitably modified chemical structures has not been reported.

DISCLOSURE OF THE INVENTION

The present inventors took note of the glutamic acid nervous functional depression hypothesis, and conducted intensive studies in an attempt to develop a compound which ameliorates positive symptoms as well as negative symptoms of schizophrenia and recognition function disorder, and which is free of serious side effects such as extrapyramidal disorders, agranulocytosis and the like. As a result, it has been found that the condensed thiophene compound of the formula (I) has superior dopamine receptor inhibitory action and glutamic acid nervous system function depression-ameliorating action, shows anti-methamphetamine action, anti-apomorphine action, conditioned avoidance response inhibitory action, MK-801-induced neurotoxicity inhibitory action, MK-801 discrimination antagonistic action, clozapine discrimination generalization action and the like in test animals such as mouse, rat and the like, and is useful as an antipsychotic agent; that the compound shows less side effects in the extrapyramidal system, such as catalepsy induction and the like; and that a reaction intermediate corresponding to the cation radical intermediate considered to cause agranulocytosis induced by clozapine was not detected when the reaction intermediate was analyzed by an ESR spectrum, using oxydation of the compound of the formula (I) by horseradish peroxidase as a model reaction of the metabolitic reaction of this compound, which resulted in the completion of the present invention.

It is therefore an object of the present invention to provide a condensed thiophene compound useful as a therapeutic agent for schizophrenia and the like and an important synthetic intermediate therefor. The condensed thiophene compound of the formula (I) is also useful as a therapeutic agent for Alzheimer's disease and manic-depressive illness.

Accordingly, the present invention provides the following.

(1) A condensed thiophene compound of the formula (I)

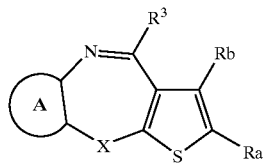

(I)

wherein

Ra and Rb are the same or different and each is hydrogen, alkyl, cycloalkyl, acyl, alkenyl, aryl, heteroaryl, aralkyl, alkoxy, hydroxyalkyl, aminoalkyl, monoalkylaminoalkyl, dialkylaminoalkyl, alkoxyalkyl, acyloxyalkyl, acylaminoalkyl, halogen, alkyl halide or nitro, or Ra and Rb in conjunction may form a benzene ring or cyclohexene ring optionally having substituents $R^1$, $R^2$ wherein $R^1$, $R^2$ are the same or different and each is hydrogen, alkyl, alkoxy, hydroxyl or halogen;

X is NH, O, S, SO, $SO_2$ or N-$R^4$ wherein $R^4$ is alkyl, provided that when X is NH, Ra and Rb in conjunction form a benzene ring optionally having substituents $R^1$, $R^2$, and when X is S, SO or $SO_2$, Ra and Rb in conjunction form a benzene ring or cyclohexene ring optionally having substituents $R^1$, $R^2$;

ring A is a benzene ring having 1 to 4 the same or different substituents thereon selected from the group consisting of alkyl, cycloalkyl, alkoxy, alkoxyalkyl, halogen, alkyl halide, nitro, amino, monoalkylamino, dialkylamino, acylamino, hydroxyl and cyano or a benzene ring without a substituent; and $R^3$ is a grou of the formula (1), formula (2), formula (3), formula (26), formula (27), formula (28), formula (29) or formula (30)

(1)

(2)

(3)

(26)

(27)

(28)

(29)

(30)

in the formula (1), formula (26), formula (27) and formula (30), $R^5$, $R^6$ and $R^7$ are the same or different and each is hydrogen, alkyl, cycloalkyl, aryl, heteroaryl, aralkyl, hydroxyalkyl, hydroxyalkoxyalkyl, amninoalkyl, monoalkylaminoalkyl, dialkylaminoalkyl or alkoxyalkyl and a is an integer of 2–4, in the formula (2) and formula (28), $R^8$ is hydrogen, alkyl, cycloalkyl, aryl, heteroaryl, aralkyl, hydroxyalkyl, hydroxyalkoxyalkyl, aminoallyl, monoalkylaminoalkyl, dialkylaminoalkyl, acyl, alkoxycarbonyl or alkoxyalkyl, b is 1 or 2, provided that the combination of X is O and $R^8$ is aralkyl is excluded and when X is O, alkyl of alkyl, hydroxyalkyl or alkoxyalkyl at $R^8$ has 1 to 4 carbon atoms, in the formula (3) and formula (29), $R^9$ is hydrogen, alkyl, cycloalkyl, aryl, heteroaryl, aralkyl, hydroxyalkyl, hydroxyalkoxyalkyl, aminoalkyl, monoalkylaminoalkyl, dialkylaminoalkyl, acyl, alkoxycarbonyl or alkoxyalkyl, or a pharmaceutically acceptable salt thereof or a hydrate thereof.

(2) The condensed thiophene compound of (1) above, wherein the formula (I) is formula (IA)

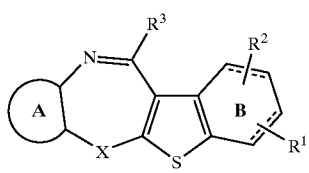

(IA)

wherein

X is NH, O, S, SO, $SO_2$ or N-$R^4$ wherein $R^4$ is alkyl;

$R^1$ and $R^2$ are the same or different and each is hydrogen, alkyl, alkoxy, hydroxyl or halogen;

ring A is a benzene ring having 1 to 4 the same or different substituents thereon selected from the group consisting of alkyl, cycloalktyl, alkoxy, alkoxyalkyl, halogen, alkyl halide, nitro, amino, monoalkylamino, dialkylamino, acylamino, hydroxyl and cyano or a benzene ring without a substituent;

ring B is a benzene ring wherein the bond shown by a dotted line and a solid line is a double bond or a cyclohexane ring wherein said bond is a single bond, provided that when X is NH, the bond shown by a dotted line and a solid line is not a single bond; and $R^3$ is a group of the formula (1), formula (2), formula (3), formula (26), formula (27), formula (28), formula (29) or formula (30)

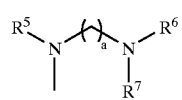

(1)

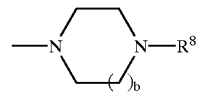

(2)

(3)

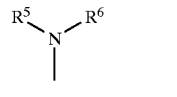

(26)

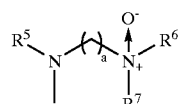

(27)

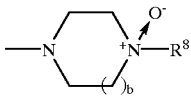

(28)

(29)

(30)

in the formula (1), formula (26), formula (27) and formula (30), $R^5$, $R^6$ and $R^7$ are the same or different and each is hydrogen, alkyl, cycloalkyl, aryl, heteroaryl, aralkyl, hydroxyallyl, hydroxyalkoxyalkyl, aminoalkyl, monoalkylaminoalkyl, dialkylaminoalkyl or alkoxyalkyl and a is an integer of 2–4, in the formula (2) and formula (28), $R^8$ is hydrogen, alkyl, cycloalkyl, aryl, heteroaryl, aralkyl, hydroxyalkyl, hydroxyalkoxyalkyl, aminoalkyl, monoalkylaminoalkyl, dialkylaminoalkyl, acyl, alkoxycarbonyl or alkoxyalkyl, b is 1 or 2, in the formula (3) and formula (29), $R^9$ is hydrogen, alkyl, cycloalkyl, aryl, heteroaryl, aralkyl, hydroxyalkyl, hydroxyalkoxyalkyl, aminoalkyl, monoalkylaminoalkyl, dialkylaminoalkyl, acyl, alkoxycarbonyl or alkoxyalkyl, or a pharmaceutically acceptable salt thereof or a hydrate thereof.

(3) The condensed thiophene compound of (2) above, wherein the ring B is a benzene ring wherein the bond shown by a dotted line and a solid line is a double bond, or a pharmaceutically acceptable salt thereof or a hydrate thereof.

(4) The condensed thiophene compound of (2) above, wherein X is NH, O or S, $R^1$ and $R^2$ are the same or different and each is hydrogen, halogen, alkoxy or alkyl, the ring A is a benzene ring having 1 to 4 the same or different substituents thereon selected from the group consisting of alkyl, alkoxy, halogen and alkyl halide, or a benzene ring without a substituent, the ring B is a benzene ring wherein the bond shown by a dotted line and a solid line is a double bond, and $R^3$ is a group of the formula (2) wherein $R^8$ is hydroxyalkoxyalkyl, methyl or ethyl and b is 1, or a pharmaceutically acceptable salt thereof or a hydrate thereof.

(5) The condensed thiophene compound of (2) above, wherein X is NH, $R^1$ and $R^2$ are the same or different and each is hydrogen, halogen, alkoxy or alkyl, the ring A is a benzene ring having 1 to 4 the same or different substituents thereon selected from the group consisting of alkyl, alkoxy, halogen and alkyl halide, or a benzene ring without a substituent, the ring B is a benzene ring wherein the bond shown by a dotted line and a solid line is a double bond, and $R^3$ is a group of the formula (2) wherein $R^8$ is methyl or ethyl and b is 1, or a pharmaceutically acceptable salt thereof or a hydrate thereof.

(6) The condensed thiophene compound of (2) above, which is a member selected from the group consisting of 12-(4-methylpiperazin-1-yl)-6H-[1]benzothieno[2,3-b][1,5]benzodiazepine, 8-fluoro-12-(4-methylpiperazin-1-yl)-6H-[1]benzothieno[2,3-b][1,5benzodiaze, 8-methyl-12-(4-methylpiperazin-1-yl)-6H-[1]benzothieno [2,3-b][1,5]benzodiazepine,
8-chloro-12-(4-methylpiperazin-1-yl)-6H-[1]benzothieno [2,3-b][1,5]benzodiazepine,
8-bromo-12-(4-methylpiperazin-1-yl)-6H-[1]benzothieno [2,3-b][1,5]benzodiazepine,
9-fluoro-12-(4-methylpiperazin-1-yl)-6H-[1]benzothieno[2, 3-b][1,5]benzodiazepine,
9-methyl-12-(4-methylpiperazin-1-yl)-6H-[1]benzothieno [2,3-b][1,5]benzodiazepine,
9-chloro-12-(4-methylpiperazin-1-yl)-6H-[1]benzothieno [2,3-b][1,5]benzodiazepine,
9-bromo-12-(4-methylpiperazin-1-yl)-6H-[1]benzothieno [2,3-b][1,5]benzodiazepine,
9-methoxy-12-(4-methylpiperazin-1-yl)-6H-[1]benzothieno [2,3-b][1,5,]benzodiazepine,
8,9-difluoro-12-(4-methylpiperazin-1-yl)-6H-[1] benzothieno[2,3-b][1,5]benzodiazepine,
8,10-difluoro-12-(4-methylpiperazin-1-yl)-6H-[1] benzothieno[2,3-b][1,5]benzodiazepine,
3-methyl-12-(4-methylpiperazin-1-yl)-6H-[1]benzothieno [2,3-b][1,5]benzodiazepine,
8-fluoro-3-methyl-12-(4-methylpiperazin-1-yl)-6H-[1] benzothieno[2,3-b ][1,5]benzodiazepine,
2-methyl-12-(4-methylpiperazin-1-yl)-6H-[1]benzothieno [2,3-b][1,5]benzodiazepine,
8-fluoro-2-methyl-12-(4-methylpiperazin-1-yl)-6H-[1] benzothieno[2,3-b][1,5]benzodiazepine,
3-methoxy-12-(4-methylpiperazin-1-yl)-6H-[1]benzothieno [2,3-b][1,5]benzodiazepine,
8-fluoro-3-methoxy-12-(4-methylpiperazin-1-yl)-6H-[1] benzothieno[2,3-b][1,5]benzodiazepine
8,9-dichloro-12-(4-methylpiperazin-1-yl)-6H-[1] benzothieno[2,3-b][1,5]benzodiazepine,
7,8-dichloro-12-(4-methylpiperazin-1-yl)-6H-[1] benzothieno[2,3-b][1,5]benzodiazepine,
3-bromo-8-fluoro-12-(4-methylpiperazin-1-yl)-6H-[1] benzothieno[2,3-b][1,5]benzodiazepine,
3-fluoro-12-(4-methylpiperazin-1-yl)-6H-[1]benzothieno[2, 3-b][1,5]benzodiazepine,
3-chloro-12-(4-methylpiperazin-1-yl)-6H-[1]benzothieno [2,3-b][1,5]benzodiazepine,
1-methyl-12-(4-methylpiperazin-1-yl)-6H-[1]benzothieno [2,3-b][1,5]benzodiazepine,
4-methyl-12-(4-methylpiperazin-1-yl)-6H-[1]benzothieno [2,3-b][1,5]benzodiazepine,
3,8-difluoro-12-(4-methylpiperazin-1-yl)-6H-[1] benzothieno[2,3-b][1,5]benzodiazepine,
3-fluoro-8-methyl-12-(4-methylpiperazin-1-yl)-6H-[1] benzothieno[2,3-b][1,5]benzodiazepine and
12-(4-ethylpiperazin-1-yl)-8-fluoro-6H-[1]benzothieno[2,3-b][1,5]benzodiazepine or a pharmaceutically acceptable salt thereof or a hydrate thereof.

(7) A pharmaceutical agent comprising a condensed thiophene compound of formula (IA) or a pharmaceutically acceptable salt thereof or a hydrate thereof, a pharmaceutical composition comprising said compound and a pharmaceutically acceptable additive, and an antipsychotic agent comprising, as an active ingredient, a compound of the formula (IA).

(8) A benzothiophene compound of the formula (IIA)

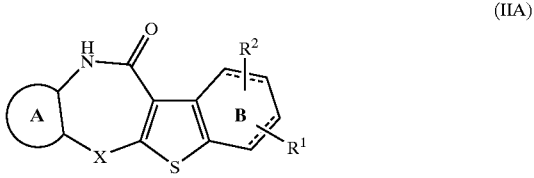

(IIA)

wherein X is NH, O, S, SO, $SO_2$ or $N-R^4$ wherein $R^4$ is alkyl, $R^1$ and $R^2$ are the same or different and each is hydrogen, alkyl, alkoxy, hydroxyl or halogen, ring A is a benzene ring having 1 to 4 the same or different substituents thereon selected from the group consisting of alkyl, cycloalkyl, alkoxy, alkoxyalkyl, halogen, alkyl halide, nitro, amino, monoalkylamino, dialkylamino, acylamino, hydroxyl and cyano or a benzene ring without a substituent, and ring B is a benzene ring wherein the bond shown by a dotted line and a solid line is a double bond or a cyclohexane ring wherein said bond is a single bond, provided that when X is NH, the bond shown by a dotted line and a solid line is not a single bond, which is an important intermediate for the synthesis of the of compound of the formula (IA).

(9) A benzothiophene compound of (8) above, wherein X is NH, O or S, $R^1$ and $R^2$ are the same or different and each is hydrogen, halogen, alkoxy or alkyl, the ring A is a benzene ring having 1 to 4 the same or different substituents thereon selected from the group consisting of alkyl, alkoxy, halogen, hydroxyl and alkyl halide, or a benzene ring without a substituent, and the ring B is a benzene ring wherein the bond shown by a dotted line and a solid line is a double bond or a cyclohexane ring wherein said bond is a single bond, provided that when X is NH, the bond shown by a dotted line and a solid line is not a single bond.

(10) The benzothiophene compound of (8) above, which is a member selected from the group consisting of 6H-[1]benzothieno[2,3-b][1,5]benzodiazepin-12(11H)-one,
8-fluoro-6H-[1]benzothieno[2,3-b][1,5]benzodiazepin-12 (11H)-one,
8-chloro-6H-[1]benzothieno[2,3-b][1,5]benzodiazepin-12 (11H)-one,
8-bromo-6H-[1]benzothieno[2,3-b][1,5]benzodiazepin-12 (11H)-one,
8-methyl-6H-[1]benzothieno[2,3-b][1,5]benzodiazepin-12 (11H)-one,
9-fluoro-6H-[1]benzothieno[2,3-b][1,5]benzodiazepin-12 (11H)-one,
9-chloro-6H-[1]benzothieno[2,3-b][1,5]benzodiazepin-12 (11H)-one,
9-bromo-6H-[1]benzothieno[2,3-b][1,5]benzodiazepin-12 (11H)-one,
9-methyl-6H-[1]benzothieno[2,3-b][1,5]benzodiazepin-12 (11H)-one,
9-methoxy-6H-[1 ]benzothieno[2,3-b][1,5]benzodiazepin-12(11H)-one,
8,9-difluoro-6H-[1]benzothieno[2,3-b][1,5]benzodiazepin-12(11H)-one,
3-methyl-6H-[1]benzothieno[2,3-b][1,5]benzodiazepin-12 (11H)-one,
8-fluoro-3-methyl-6H-[1]benzothieno[2,3-b][1,5] benzodiazepin-12(11H)-one,
3-methoxy-6H-[1]benzothieno[2,3-b][1,5]benzodiazepin-12(11H)-one,
8-fluoro-3-methoxy-6H-1]benzothieno[2,3-b][1,5] benzodiazepin-12(11H)-one, 2-methyl-6H-[1]benzothieno[2,3-b][1,5]benzodiazepin-12 (11H)-one,
8-fluoro-2-methyl-6H-[1]benzothieno[2,3-b][1,5] benzodiazepin-12(11H)-one,
3,9-dimethyl-6H-[1]benzothieno[2,3-b][1,5]benzodiazepin-12(11H)-one,
1,2,3,4-tetrahydro-[1]benzothieno[2,3-b][1,5] benzoxazepin-12(11H)-one,
1,2,3,4-tetrahydro-8-methyl-[1]benzothieno[2,3-b][1,5] benzoxazepin-12(11H)-one,
8-fluoro-1,2,3,4-tetrahydro-[1]benzothieno[2,3-b][1,5] benzoxazepin-12(11H)-one,
[1]benzothieno[2,3-b][1,5]benzoxazepin-12(11H)-one,
8-methyl-[1]benzothieno[2,3-b][1,5]benzoxazepin-12 (11H)-one,
8-fluoro-[1]benzothieno[2,3-b][1,5]benzoxazepin-12(11H)-one,
1,2,3,4-tetrahydro-[1]benzothieno[2,3-b][1,5] benzothiazepin-12(11H)-one,
1,2,3,4-tetrahydro-8-methyl-[1]benzothieno[2,3-b][1,5] benzothiazepin-12(11H)-one,
8-fluoro-1,2,3,4-tetrahydro-[1]benzothieno[2,3-b][1,5] benzothiazepin-12(11H)-one,
[1]benzothieno[2,3-b][1,5]benzothiazepin-12(11H)-one,
8-methyl-[1]benzothieno[2,3-b][1,5]benzothiazepin-12 (11H)-one,
8-fluoro-[1]benzothieno[2,3-b][1,5]benzothiazepin-12 (11H)-one,
8,9-dichloro-6H-[1]benzothieno[2,3-b][1,5]benzodiazepin-12(11H)-one,
7,8-dichloro-6H-[1]benzothieno[2,3-b][1,5]benzodiazepin-12(11H)-one,
9-trifluoromethyl-6H-[1]benzothieno[2,3-b][1,5] benzodiazepin-12(11H)-one,
3-bromo-8-fluoro-6H-[1]benzothieno[2,3-b][1,5] benzodiazepin-12(11H)-one,
6-methyl-[1]benzothieno[2,3-b][1,5]benzodiazepin-12 (11H)-one,
3-fluoro-6H-[1]benzothieno[2,3-b][1,5]benzodiazepin-12 (11H)-one,
3-chloro-6H-[1]benzothieno[2,3-b][1,5]benzodiazepin-12 (11H)-one,
1-methyl-6H-[1]benzothieno[2,3-b][1,5]benzodiazepin-12 (11H)-one,
4-methyl-6H-[1]benzothieno[2,3-b][1,5]benzodiazepin-12 (11 H)-one,
3,8-difluoro-6H-[1]benzothieno[2,3-b][1,5]benzodiazepin-12(11H)-one and
3-fluoro-8-methyl-6H-[1]benzothieno[2,3-b][1,5] benzodiazepin-12(11H )-one.

(11) The condensed thiophene compound of (1) above, wherein the formula (I) is formula (IB)

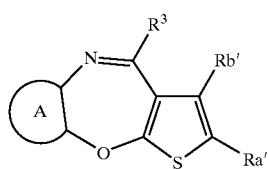

(IB)

wherein
Ra' and Rb' are the same or different and each is hydrogen, alkyl, cycloalkyl, acyl, alkenyl, aryl, heteroaryl, aralkyl, alkoxy, hydroxyalkyl, aminoalkyl, monoalkylaminoalkyl, dialkylaminoalkyl, alkoxyalkyl, acyloxyalkyl, acylaminoalkyl, halogen, alkyl halide or nitro, and ring A is a benzene ring having 1 to 4 the same or different substituents thereon selected from the group consisting of alkyl, cycloalkyl, alkoxy, alkoxyalkyl, halogen, alkyl halide, nitro, amino, monoalkylamino, dialkylamino, acylamino, hydroxyl and cyano or a benzene ring without a substituent; and $R^3$ is a group of the formula (1), formula (2), formula (3), formula (26), formula (27), formula (28), formula (29) or formula (30)

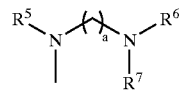

(1)

(2)

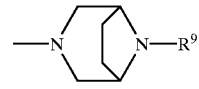

(3)

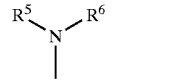

(26)

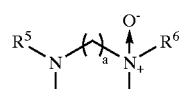

(27)

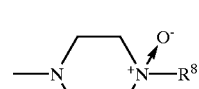

(28)

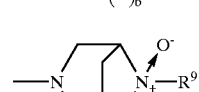

(29)

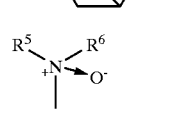

(30)

in the formula (1), formula (26), formula (27) and formula (30), $R^5$, $R^6$ and $R^7$ are the same or different and each is hydrogen, alkyl, cycloalkyl, aryl, heteroaryl, aralkyl, hydroxyalkyl, hydroxyalkoxyalkyl, aminoalkyl, monoalkylaminoalkyl, dialkylaminoalkyl or alkoxyalkyl and a is an integer of 2–4, in the formula (2) and formula (28), $R^8$ is hydrogen, alkyl having 1 to 4 carbon atoms, cycloalkyl, hydroxyalkyl having 1 to 4 carbon atoms, hydroxyalkoxyalkyl, aminoalkyl, monoalkylaminoalkyl, dialkylaminoalkyl, acyl, alkoxycarbonyl or alkoxyalkyl wherein alkyl having 1 to 4 carbon atoms is substituted by alkoxy, and b is 1 or 2, in the formula (3) and formula (29), $R^9$ is hydrogen, alkyl, cycloalkyl, aryl, heteroaryl, aralkyl, hydroxyalkyl, hydroxyalkoxyalkyl, aminoalkyl, monoalkylaminoalkyl, dialkylaminoalkyl, acyl, alkoxycarbonyl or alkoxyalkyl, or a pharmaceutically acceptable salt thereof or a hydrate thereof.

(12) The condensed thiophene compound of (11) above, wherein Ra' and Rb' are the same or different and each is hydrogen or alkyl, the ring A is a benzene ring having 1 to 4 the same or different substituents thereon selected from the group consisting of alkyl, alkoxy, halogen and alkyl halide, or a benzene ring without a substituent, and $R^3$ is a group of the formula (2) wherein $R^8$ is hydroxyalkoxyalkyl, methyl or ethyl and b is 1, or a pharmaceutically acceptable salt thereof or a hydrate thereof.

(13) The condensed thiophene compound of (11) above, wherein Ra' is alkyl, Rb' is hydrogen or alkyl the ring A is a benzene ring having one substituent thereon selected from the group consisting of alkyl, alkoxy and halogen, or a benzene ring without a substituent, and $R^3$ is a group of the formula (2) wherein $R^8$ is methyl and b is 1, or a pharmaceutically acceptable salt thereof or a hydrate thereof.

(14) The condensed thiophene compound of (11) above, which is a member selected from the group consisting of 2-methyl-4-(4-methylpiperazin-1-yl)thieno[2,3-b][1,5] benzoxazepine,
2-ethyl-4-(4-methylpiperazin-1-yl)thieno[2,3-b][1,5] benzoxazepine,
2,8-dimethyl-4-(4-methylpiperazin-1-yl)thieno[2,3-b][1,5] benzoxazepine,
8-methoxy-2-methyl-4-(4-methylpiperazin-1-yl)thieno[2,3-b][1,5]benzoxazepine,
2,6-dimethyl-4-(4-methylpiperazin-1-yl)thieno[2,3-b][1,5] benzoxazepine,
2,9-dimethyl-4-(4-methylpiperazin-1-yl)thieno[2,3-b][1,5] benzoxazepine,
2,3-dimethyl-4-(4-methylpiperazin-1-yl)thieno[2,3-b][1,5] benzoxazepine,
8-chloro-2-methyl-4-(4-methylpiperazin-1-yl)thieno[2,3-b][1,5]benzoxazepine and
8-fluoro-2-methyl-4-(4-methylpiperazin-1-yl)thieno[2,3-b][1,5]benzoxazepine or a pharmaceutically acceptable salt thereof or a hydrate thereof.

(15) A pharmaceutical agent comprising a condensed thiophene compound of formula (IB) or a pharmaceutically acceptable salt thereof or a hydrate thereof, a pharmaceutical composition comprising said compound and a pharmaceutically acceptable additive, and an antipsychotic agent comprising, as an active ingredient, a compound of formula (IB).

(16) A thienobenzoxazepinone compound of the formula (IIB)

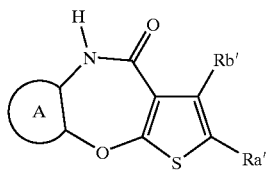

(IIB)

wherein Ra' and Rb' are the same or different and each is hydrogen, alkyl, cycloalkyl, acyl, alkenyl, aryl, heteroaryl, aralkyl, alkoxy, hydroxyalkyl, aminoalkyl, monoalkylaminoalkyl, dialkylaminoalkyl, alkoxyalkyl, acyloxyalkyl, acylaminoalkyl, halogen, alkyl halide or nitro, and ring A is a benzene ring having 1 to 4 the same or different substituents thereon selected from the group consisting of alkyl, cycloalkyl, alkoxy, alkoxyalkyl, halogen, alkyl halide, nitro, amino, monoalkylamino, dialkylamino, acylamino, hydroxyl and cyano or a benzene ring without a substituent, which is an important intermediate for the synthesis of the of compound of the formula (IB).

(17) The thienobenzoxazepinone compound of (16) above, wherein Ra' and Rb' are the same or different and each is hydrogen or alkyl, and the ring A is a benzene ring having 1 to 4 the same or different substituents thereon selected from the group consisting of alkyl, alkoxy, halogen, hydroxyl and alkyl halide, or a benzene ring without a substituent.

(18) The thienobenzoxazepinone compound of (16) above, which is a member selected from the group consisting of 2-methylthieno[2,3-b][1,5]benzoxazepin-4(5H)-one,
2,3-dimethylthieno[2,3-b][1,5]benzoxazepin-4(5H)-one,
2,8-dimethylthieno[2,3-b][1,5]benzoxazepin-4(5H)-one,
8-chloro-2-methylthieno[2,3-b][1,5]benzoxazepin-4(5H)-one,
8-fluoro-2-methylthieno[2,3-b][1,5]benzoxazepin-4(5H)-one,
8-methoxy-2-methylthieno[2,3-b][1,5]benzoxazepin-4(5H)-one,
2,6-dimethylthieno[2,3-b][1,5]benzoxazepin-4(5H)-one,
2,9-dimethylthieno[2,3-b][1,5]benzoxazepin-4(5H)-one and
2-ethylthieno[2,3-b][1,5]benzoxazepin-4(5H)-one

DETAILED DESCRIPTION OF THE INVENTION

In the present invention, each symbol used specifically means the following.

Alkyl is alkyl having 1 to 5 carbon atoms, such as methyl, ethyl, propyl, isopropyl, butyl, isobutyl, tert-butyl and pentyl.

Cycloalkyl is cycloalkyl having 3 to 6 carbon atoms, such as cyclopropyl, cyclopentyl, cyclohexyl and the like.

Alkoxy is alkoxy having 1 to 5 carbon atoms, such as methoxy, ethoxy, propoxy, isopropoxy, butoxy, isobutoxy, tert-butoxy and the like.

Aryl is phenyl or naphthyl, with preference given to phenyl.

Heteroaryl is pyridyl, furyl, thienyl and the like.

Aralkyl is that wherein aryl has been substituted by alkyl having 1 to 5 carbon atoms and is exemplified by benzyl, 1-phenylethyl, 2-phenylethyl, 3-phenylpropyl, 4-phenylbutyl and the like.

Hydroxyalkyl is hydroxyalkyl having 1 to 5 carbon atoms, such as hydroxymethyl, 2-hydroxyethyl, 1-hydroxyethyl, 3-hydroxypropyl, 1-hydroxypropyl, 4-hydroxybutyl, 1-hydroxy-1-methylethyl and the like.

Hydroxyalkoxyalkyl is that wherein alkyl having 1 to 4 carbon atoms has been bonded to hydroxyalkyl having 1 to 4 carbon atoms via one oxygen atom, and is exemplified by 2-(2-hydroxyethoxy)ethyl and the like.

Aminoalkyl is that wherein alkyl having 1 to 5 carbon atoms has been substituted by amino, which is exemplified by aminomethyl, 2-aminoethyl, 1-aminoethyl, 3-aminopropyl, 1-aminopropyl, 4-aminobutyl, 1-amino-1-methylethyl and the like.

Monoalkylaminoalkyl is that wherein nitrogen atom of aminoalkyl is substituted by one alkyl having 1 to 5 carbon atoms, which is exemplified by methylaminomethyl, N-methyl-2-aminoethyl, N-methyl-1-aminoethyl, N-methyl-3-aminopropyl, N-methyl-1-aminopropyl, N-methyl-4-aminobutyl, N-methyl-1-amino-1-methylethyl and the like.

Dialkylaminoalkyl is that wherein nitrogen atom of aminoalkyl has been substituted by two alkyl having 1 to 5 carbon atoms, which is exemplified by dimethylaminomethyl, N,N-dimethyl-2-aminoethyl, N,N-dimethyl-1-aminoethyl, N,N-dimethyl-3-aminopropyl, N,N-dimethyl-1-aminopropyl, N,N-dimethyl-4-aminobutyl, N,N-dimethyl-1-amino-1-methylethyl and the like.

Alkoxyalkyl is that wherein alkyl having 1 to 5 carbon atoms has been substituted by alkoxy, such as methoxymethyl, methoxyethyl, ethoxymethyl, ethoxyethyl and the like.

Halogen is fluorine, chlorine, bromine or iodine.

Alkyl halide is that having 1 to 5 carbon atoms, such as fluoromethyl, difluoromethyl, trifluoromethyl, chloromethyl, dichloromethyl, trichloromethyl and the like.

Monoalkylamino is amino substituted by one alkyl having 1 to 5 carbon atoms, such as methylamino, ethylamino and the like.

Dialkylamino is amino substituted by two alkyl having 1 to 5 carbon atoms, such as dimethylamino, diethylamino and the like.

Acyl is that having 2 to 7 carbon atoms, such as acetyl, propanoyl, butanoyl, pivaloyl, benzoyl and the like.

Acylamino is that wherein amino or monoalkylamino is bonded to acyl having 1 to 5 carbon atoms, such as acetylamino, N-acetyl-N-methylamino and the like. As used herein, acyl means that having 2 to 5 carbon atoms, such as acetyl, propanoyl, butanoyl, pivaloyl and the like.

Alkoxycarbonyl is that having 2 to 8 carbon atoms, such as methoxycarbonyl, ethoxycarbonyl, propoxycarbonyl, butoxycarbonyl, tert-butoxycarbonyl, benzyloxycarbonyl, pentoxycarbonyl and the like.

The ring B is preferably a benzene ring wherein the bond shown by a dotted line and a solid line is a double bond.

The group of the formula (1) as defined by the above-mentioned $R^5$, $R^6$, $R^7$ and integer a is N-(N',N'-dimethyl-2-aminoethyl)amino, N-(N',N'-dimethyl-2-aminoethyl)-N-methylamino and the like.

The group of the formula (2) as defined by the above-mentioned $R^8$ and integer b is piperazin-1-yl, 4-methylpiperazin-1-yl, 4-ethylpiperazin-1-yl, 4-propylpiperazin-1-yl, 4-isopropylpiperazin-1-yl, 4-[2-(2-hydroxyethoxy)ethyl]piperazin-1-yl, 4-methylhomopiperazin-1-yl and the like, with preference given to 4-methylpiperazin-1-yl.

The group of the formula (3) as defined by the above-mentioned $R^9$ is 8-methyl-3,8-diazabicyclo[3,2,1]octan-3-yl and the like.

The group of the formula (26) as defined by the above-mentioned $R^5$ and $R^6$ is amino, N,N-dimethylamino and the like.

The group of the formula (27) as defined by the above-mentioned $R^5$, $R^6$, $R^7$ and integer a is N-(N',N'-dimethyl-2-aminoethyl)amino-N'-oxide, N-(N',N'-dimethyl-2-aminoethyl)-N-methylamino-N'-oxide and the like.

The group of the formula (28) as defined by the above-mentioned $R^8$ and integer b is 4-methylpiperazine-4-oxide-1-yl and the like.

The group of the formula (29) as defined by the above-mentioned $R^9$ is 8-methyl-3,8-diazabicyclo[3,2,1]octane-8-oxide-3-yl and the like.

The group of the formula (30) as defined by the above-mentioned $R^5$ and $R^6$ is amino-N-oxide, N,N-dimethylamino-N-oxide and the like.

The compound of the formula (I) is specifically a compound of the formula (IA) or a compound of the formula (IB).

The compound of the formula (IA), a pharmaceutically acceptable salt thereof and hydrates thereof are preferably a condensed thiophene compound of the formula (IA) wherein X is NH, O or S, $R^1$ and $R^2$ are the same or different and each is hydrogen, halogen, alkoxy or alkyl, ring A is a benzene ring having 1 to 4 the same or different substituents thereon selected from the group consisting of alkyl, alkoxy, halogen and alkyl halide, or a benzene ring without a substituent, ring B is a benzene ring wherein the bond shown by a dotted line and a solid line is a double bond, and $R^3$ is a group of the formula (2) wherein $R^8$ is hydroxyalkoxyalkyl, methyl or ethyl and b is 1, a pharmaceutically acceptable salt thereof and hydrates thereof.

More preferred are a condensed thiophene compound of the formula (IA) wherein

X is NH, $R^1$ and $R^2$ are the same or different and each is hydrogen, halogen, alkoxy or alkyl, ring A is a benzene ring having 1 to 4 the same or different substituents thereon selected from the group consisting of alkyl, alkoxy, halogen and alkyl halide, or a benzene ring without a substituent, ring B is a benzene ring wherein the bond shown by a dotted line and a solid line is a double bond, and $R^3$ is a group of the formula (2) wherein $R^8$ is methyl or ethyl and b is 1, a pharmaceutically acceptable salt thereof and hydrates thereof.

Preferable compounds of the formula (IA) include the following compounds wherein the number denotes Example numbers.

(1) 12-(4-methylpiperazin-1-yl)-6H-[1]benzothieno[2,3-b][1,5]benzodiazepine, (2) 8-fluoro-12-(4-methylpiperazin-1-yl)-6H-[1]benzothieno[2,3-b][1,5]benzodiazepine, (6) 8-methyl-12-(4-methylpiperazin-1-yl)-6H-[1]benzothieno[2,3-b][1,5]benzodiazepine, (7) 8-chloro-12-(4-methylpiperazin-1-yl)-6H-[1]benzothieno[2,3-b][1,5]benzodiazepine, (8) 8-bromo-12-(4-methylpiperazin-1-yl)-6H-[1]benzothieno[2,3-b][1,5]benzodiazepine,

(49) 9-fluoro-12-(4-methylpiperazin-1-yl)-6H-[1]benzothieno[2,3-b][1,5]benzodiazepine,

(10) 9-methyl-12-(4-methylpiperazin-1-yl)-6H-[1]benzothieno[2,3-b][1,5]benzodiazepine,

(11) 9-chloro-12-(4-methylpiperazin-1-yl)-6H-[1]benzothieno[2,3-b][1,5]benzodiazepine,

(12) 9-bromo-12-(4-methylpiperazin-1-yl)-6H-[1]benzothieno[2,3-b][1,5]benzodiazepine,

(13) 9-methoxy-12-(4-methylpiperazin-1-yl)-6H-[1]benzothieno[2,3-b][1.5]benzodiazepine,

(50) 8,9-difluoro-12-(4-methylpiperazin-1-yl)-6H-[1]benzothieno[2,3-b][1,5]benzodiazepine,

(15) 8,10-difluoro-12-(4-methylpiperazin-1-yl)-6H-[1]benzothieno[2,3-b][1,5]benzodiazepine,

(16) 3-methyl-12-(4-methylpiperazin-1-yl)-6H-[1]benzothieno[2,3-b][1,5]benzodiazepine,

(17) 8-fluoro-3-methyl-12-(4-methylpiperazin-1-yl)-6H-[1]benzothieno[2,3-b][1,5]benzodiazepine,

(18) 2-methyl-12-(4-methylpiperazin-1-yl)-6H-[1]benzothieno[2,3-b][1,5]benzodiazepine,

(19) 8-fluoro-2-methyl-12-(4-methylpiperazin-1-yl)-6H-[1]benzothieno[2,3-b][1,5]benzodiazepine,

(20) 3-methoxy-12-(4-methylpiperazin-1-yl)-6H-[1]benzothieno[2,3-b][1,5]benzodiazepine,
(21) 8-fluoro-3-methoxy-12-(4-methylpiperazin-1-yl)-6H-[1]benzothieno[2,3-b][1,5]benzodiazepine,
(22) 8,9-dichloro-12-(4-methylpiperazin-1-yl)-6H-[1]benzothieno[2,3-b][1,5]benzodiazepine,
(23) 7,8-dichloro-12-(4-methylpiperazin-1-yl)-6H-[1]benzothieno[2,3-b][1,5]benzodiazepine,
(25) 3-bromo-8-fluoro-12-(4-methylpiperazin-1-yl)-6H-[1]benzothieno[2,3-b][1,5]benzodiazepine,
(42) 3-fluoro-12-(4-methylpiperazin-1-yl)-6H-[1]benzothieno[2,3-b][1,5]benzodiazepine,
(43) 3-chloro-12-(4-methylpiperazin-1-yl)-6H-[1]benzothieno[2,3-b][1,5]benzodiazepine,
(45) 1-methyl-12-(4-methylpiperazin-1-yl)-6H-[1]benzothieno[2,3-b][1,5]benzodiazepine,
(46) 4-methyl-12-(4-methylpiperazin-1-yl)-6H-[1]benzothieno[2,3-b][1,5]benzodiazepine,
(47) 3,8-difluoro-12-(4-methylpiperazin-1-yl)-6H-[1]benzothieno[2,3-b][1,5]benzodiazepine,
(48) 3-fluoro-8-methyl-12-(4-methylpiperazin-1-yl)-6H-[1]benzothieno[2,3-b][1,5]benzodiazepine, and
(51) 12-(4-ethylpiperazin-1-yl)-8-fluoro-6H-[1]benzothieno[2,3-b][1,5]benzodiazepine.

The present invention also encompasses pharmaceutically acceptable salts of the above-mentioned compounds and hydrates thereof.

The compound of the formula (IIA) is preferably a benzothiophene compound wherein X is NH, O or S, $R^1$ and $R^2$ are the same or different and each is hydrogen, halogen, alkoxy or alkyl, ring A is a benzene ring having 1 to 4 the same or different substituents thereon selected from the group consisting of alkyl, alkoxy, halogen and alkyl halide, or a benzene ring without a substituent, and ring B is a benzene ring wherein the bond shown by a dotted line and a solid line is a double bond or a cyclohexane ring wherein said bond is a single bond, provided that when X is NH, the bond shown by a dotted line and a solid line is not a single bond.

Specific compounds of the formula (IIA) include the following:

6H-[1]benzothieno[2,3-b][1,5]benzodiazepin-12(11H)-one,
8-fluoro-6H-[1]benzothieno[2,3-b][1,5]benzodiazepin-12(11H)-one,
8-chloro-6H-[1]benzothieno[2,3-b][1,5]benzodiazepin-12(11H)-one,
8-bromo-6H-[1]benzothieno[2,3-b][1,5]benzodiazepin-12(11H)-one,
8-methyl-6H-[1]benzothieno[2,3-b][1,5]benzodiazepin-12(11H)-one,
9-fluoro-6H-[1]benzothieno [2,3-b][1,5benzodiazepin-12(11H)-one,
9-chloro-6H-[1]benzothieno[2,3-b][1,5]benzodiazepin-12(11H)-one,
9-bromo-6H-[1]benzothieno[2,3-b][1,5]benzodiazepin-12(11H)-one,
9-methyl-6H-[1]benzothieno[2,3-b][1,5]benzodiazepin-12(11H)-one,
9-methoxy-6H-[1]benzothieno[2,3-b][1,5]benzodiazepin-12(11H)-one,
8,9-difluoro-6H-[1]benzothieno2,3-b][1,5benzodiazepin-12(11 H)-one,
3-methyl-6H-[1]benzothieno[2,3-b][1,5]benzodiazepin-12(11H)-one,
8-fluoro-3-methyl-6H-[1]benzothieno[2,3-b][1,5]benzodiazepin-12(11 H)-one,
3-methoxy-6H-[1]benzothieno[2,3-b][1,5]benzodiazepin-12(11H)-one,
8-fluoro-3-methoxy-6H-[1]benzothieno[2,3-b][1,5]benzodiazepin-12(11H)-one,
2-methyl-6H-[1]benzothieno[2,3-b][1,5]benzodiazepin-12(11H)-one,
8-fluoro-2-methyl-6H-[1]benzothieno[2,3-b][1,5]benzodiazepin-12(11H)-one,
3,9-dimethyl-6H-[1]benzothieno[2,3-b][1,5]benzodiazepin-12(11H)-one,
1,2,3,4-tetrahydro-[1]benzothieno[2,3-b][1,5]benzoxazepin-12(11H)-one,
1,2,3,4-tetrahydro-8-methyl-[1]benzothieno[2,3-b][1,5]benzoxazepin-12(11H)-one,
8-fluoro-1,2,3,4-tetrahydro-[1]benzothieno[2,3-b] 1,5]benzoxazepin-12(11H)-one,
[1]benzothieno[2,3-b][1,5]benzoxazepin-12(11H)-one,
8-methyl-[1]benzothieno[2,3-b][1,5]benzoxazepin-12(11H)-one,
8-fluoro-[1]benzothieno[2,3-b][1,5]benzoxazepin-12(11H)-one,
1,2,3,4-tetrahydro-[1]benzothieno[2,3-b][1,5]benzothiazepin-12(11H)-one,
1,2,3,4-tetrahydro-8-methyl-[1]benzothieno[2,3-b][1,5]benzothiazepin-12(11H)-one,
8-fluoro-1,2,3,4-tetrahydro-[1]benzothieno[2,3-b][1,5]benzothiazepin-12(11H)-one,
[1]benzothieno[2,3-b][1,5]benzothiazepin-12(11H)-one,
8-methyl-[1]benzothieno[2,3-b][1,5]benzothiazepin-12(11H)-one,
8-fluoro-[1]benzothieno[2,3-b][1,5]benzothiazepin-12(11H)-one,
8,9-dichloro-6H-[1]benzothieno[2,3-b][1,5]benzodiazepin-12(11H)-one,
7,8-dichloro-6H-[1]benzothieno[2,3-b][1,5]benzodiazepin-12(11H)-one,
9-trifluoromethyl-6H-[1]benzothieno[2,3-b][1,5]benzodiazepin-12(11H)-one, 3-bromo-8-fluoro-6H-[1]benzothieno[2,3-b][1,5]benzodiazepin-12(11H)-one,
6-methyl-[1]benzothieno[2,3-b][1,5]benzodiazepin-12(11H)-one,
3-fluoro-6H-[1]benzothieno[2,3-b][1,5]benzodiazepin-12(11H)-one,
3-chloro-6H-[1]benzothieno[2,3-b][1,5]benzodiazepin-12(11H)-one,
1-methyl-6H-[1]benzothieno[2,3-b][1,5]benzodiazepin-12(11H)-one,
4-methyl-6H-[1]benzothieno[2,3-b][1,5]benzodiazepin-12(11H)-one,
3,8-difluoro-6H-[1]benzothieno[2,3-b][1,5]benzodiazepin-12(11H)-one and
3-fluoro-8-methyl-6H-[1]benzothieno[2,3-b][1,5]benzodiazepin-12(11H)-one.

The compound of the formula (IB) is preferably a condensed thiophene compound wherein Ra' and Rb' are the same or different and each is hydrogen or alkyl, ring A is a benzene ring having 1 to 4 the same or different substituents thereon selected from the group consisting of alkyl, alkoxy, halogen and alkyl halide, or a benzene ring without a substituent, and $R^3$ is a group of the formula (2) wherein $R^8$ is hydroxyalkoxyalkyl, methyl or ethyl and b is 1, a pharmaceutically acceptable salt thereof and hydrates thereof.

More preferred are a condensed thiophene compound of the formula (IB) wherein
Ra' is alkyl,
Rb' is hydrogen or alkyl,
ring A is a benzene ring having one substituent thereon selected from the group consisting of alkyl, alkoxy and halogen, or a benzene ring without a substituent, and
$R^3$ is a group of the formula (2) wherein $R^8$ is methyl and b is 1, a pharmaceutically acceptable salt thereof and hydrates thereof.

Preferable compounds of the formula (IB) include the following compounds wherein the numbers in parentheses are Example numbers:

(125) 2-methyl-4-(4-methylpiperazin-1-yl)thieno[2,3-b][1,5]benzoxazepine,
(130) 2-ethyl-4-(4-methylpiperazin-1-yl)thieno[2,3-b][1,5]benzoxazepine,
(138) 2,8-dimethyl-4-(4-methylpiperazin-1-yl)thieno[2,3-b][1,5]benzoxazepine,
(142) 8-methoxy-2-methyl-4-(4-methylpiperazin-1-yl)thieno[2,3-b][1,5]benzoxazepine,
(143) 2,6-dimethyl-4-(4-methylpiperazin-1-yl)thieno[2,3-b][1,5]benzoxazepine,
(145) 2,9-dimethyl-4-(4-methylpiperazin-1-yl)thieno[2,3-b][1,5]benzoxazepine,
(144) 2,3-dimethyl-4-(4-methylpiperazin-1-yl)thieno[2,3-b][1,5]benzoxazepine,
(146) 8-chloro-2-methyl-4-(4-methylpiperazin-1-yl)thieno[2,3-b][1,5]benzoxazepine, and
(147) 8-fluoro-2-methyl-4-(4-methylpiperazin-1-yl)thieno[2,3-b][1,5]benzoxazepine.

The present invention also encompasses pharmaceutically acceptable salts of the above-mentioned compounds and hydrates thereof The compound of the formula (IIB) is preferably a thienobenzoxazepinone compound wherein
Ra' and Rb' are the same or different and each is hydrogen or alkyl and
ring A is a benzene ring having 1 to 4 the same or different substituents thereon selected from the group consisting of alkyl, alkoxy, halogen, hydroxyl and alkyl halide, or a benzene ring without a substituent.

Preferable compounds of the formula (IIB) include the following compounds wherein the numbers in parentheses are Example numbers:

(98) 2-methylthieno[2,3-b][1,5]benzoxazepin-4(5H)-one,
(101) 2,3-dimethylthieno[2,3-b][1,5]benzoxazepin-4(5H)-one,
(102) 2,8-dimethylthieno[2,3-b][1,5]benzoxazepin-4(5H)-one,
(105) 8-chloro-2methylthieno[2,3-b][1,5]benzoxazepin-4(5H)-one,
(106) 8-fluoro-2-methylthieno[2,3-b][1,5]benzoxazepin-4(5H)-one,
(107) 8-methoxy-2-methylthieno[2,3-b][1,5]benzoxazepin-4(5H)-one,
(108) 2,6-dimethylthieno[2,3-b][1,5]benzoxazepin-4(5H)-one,
(109) 2,9-dimethylthieno[2,3-b][1,5]benzoxazepin-4(5H)-one, and
(116) 2-ethylthieno[2,3-b][1,5]benzoxazepin-4(5H)-one.

The pharmaceutically acceptable salt of the compound of the formula (I), particularly formula (IA) or formula (IB), includes salts with inorganic acid, such as hydrochloric acid, hydrobromic acid, sulfuric acid, nitric acid, phosphoric acid and the like, and salts with organic acid, such as acetic acid, propionic acid, succinic acid, glycolic acid, lactic acid, malic acid, methanesulfonic acid, benzenesulfonic acid, p-toluenesulfonic acid, camphorsulfonic acid, ascorbic acid, maleic acid, citric acid, tartaric acid, fumaric acid and the like. The compound of the formula (I), particularly formula (IA) or formula (IB) and pharmaceutically acceptable salts thereof may exist in the form of hydrates or solvates, and their hydrates (1/2 hydrates, monohydrates, dihydrates, trihydrates and the like) and solvates are also encompassed in the present invention.

When the inventive compounds include asymmetric atom, they can be obtained in the form of racemic mixture or optically active compound. When the inventive compounds include at least two asymmetric atoms, they can be obtained in the form of respective diastereomers or mixtures thereof. The present invention also encompasses these mixtures and individual isomers. The present invention further encompasses stereoisomers.

The synthetic methods of the compounds of the present invention are as follows.

Method 1: Synthetic Method of Compound of Formula (IA)

A benzothiophene compound of the formula (IIA)

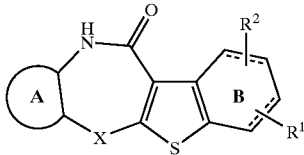

(IIA)

wherein each symbol is as defined above is kept with a suitable chlorinating agent such as thionyl chloride, phosphorus oxychloride, phosphorus pentachloride and the like, in a solvent that does not adversely affect the reaction, such as benzene, toluene, xylene, chloroform, 1,2-dichloroethane, an optionally mixed solvents therefrom and the like or without solvent, at room temperature to 170° C. for 1 to 24 hr to give a compound of the formula (4A)

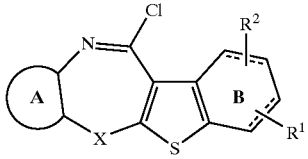

(4A)

wherein each symbol is as defined above. The obtained compound of the formula (4A) is kept with a compound of the formula (5)

$$H-R^3 \quad (5)$$

wherein $R^3$ is as defined above, in a solvent that does not adversely affect the reaction such as benzene, toluene, xylene, chloroform, 1,2-dichloroethane, an optionally mixed solvents therefrom and the like or without solvent, at room temperature to 170° C. for 1 to 24 hr to give a compound of the formula (IA).

Method 2: Synthetic Method of Compound of Formula (IA)

A benzothiophene compound of the formula (IIA) is kept with a suitable sulfurating agent such as diphosphorus tetrasulfate, Lawesson reagent and the like in a solvent that does not adversely affect the reaction, such as benzene, toluene, xylene, chloroform, 1,2-dichloroethane, an optionally mixed solvents therefrom and the like, or without solvent at room temperature to 170° C. for 1 to 24 hr to give a compound of the formula (7)

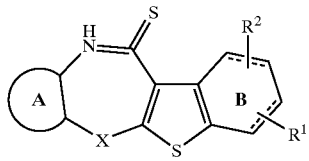

(7)

wherein each symbol is as defined above. The obtained compound of the formula (7) is reacted with a suitable methylating agent such as methyl iodide, methyl bromide and the like in a solvent that does not adversely affect the reaction such as tetrahydrofuran, N,N-dimethylformamide, acetonitrile, N-methylpyrolidone, dichloromethane, chloroform, 1,2-dichloroethane, an optionally mixed solvents therefrom and the like, in the presence of an organic base such as pyridine, triethylamine, diisopropylethylamine and the like or an inorganic base such as sodium hydride, potassium carbonate, sodium carbonate, sodium hydroxide, potassium hydroxide, potassium tert-butoxide, sodium alkoxide, butyllithium and the like, or without a base to give a compound of the formula (8)

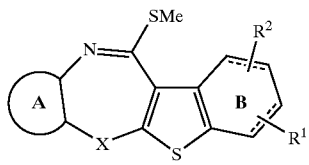

(8)

wherein each symbol is as defined above. The obtained compound of the formula (7) or the formula (8) is kept with a compound of the formula (5) in a solvent that does not adversely affect the reaction, such as tetrahydrofuran, N,N-dimethylformamide, acetonitrile, N-methylpyrolidone, dichloromethane, benzene, toluene, xylene, chloroform, 1,2-dichloroethane, an optionally mixed solvents therefrom and the like, or without solvent, at room temperature to 170° C. for 1 to 24 hr to give a compound of the formula (IA).

Method 3: Synthetic Method of Compound of Formula (IA) Wherein X is NH, N-R$^4$, O or S A benzothiophene compound of the formula (9)

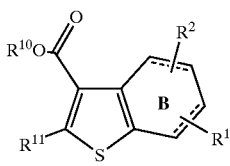

(9)

wherein R$^{10}$ is alkyl, R$^{11}$ is halogen and other symbols are as defined above, is kept with a compound of the formula (10)

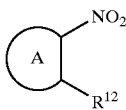

(10)

wherein R$^{12}$ is NH$_2$, NH-R$^4$, OH or SH and ring A is as defined above, in a solvent that does not adversely affect the reaction, such as N,N-dimethylformamide, dimethyl sulfoxide, N-methylpyrolidone, tetrahydrofuran, ethanol, 1,4-dioxane, an optionally mixed solvent therefrom and the like, or without solvent, in the presence of an organic base such as pyridine, triethylamine, diisopropylethylamine and the like or an inorganic base such as sodium hydride, potassium carbonate, sodium carbonate, sodium hydroxide, potassium hydroxide, potassium tert-butoxide, sodium alkoxide, butyllithium and the like at −20° C. to 170° C. for 1 to 24 hr to give a compound of the formula (11)

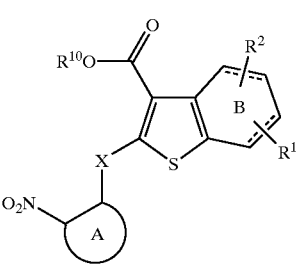

(11)

wherein each symbol is as defined above.

A compound of the formula (11a)

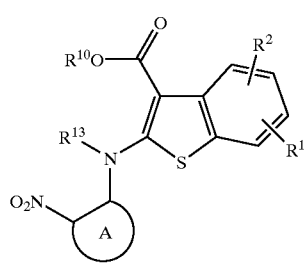

(11a)

wherein R$^{13}$ is hydrogen or alkyl and other symbols are as defined above, which is a compound of the formula (11) wherein X is NH or N-R$^4$, can be also synthesized by the following method.

For example, a benzothiophene compound of the formula (12)

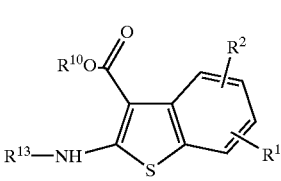

(12)

wherein each symbol is as defined above, is kept with a compound of the formula (13)

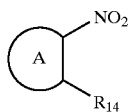

(13)

wherein $R^{14}$ is halogen and ring A is as defined above, in a solvent that does not adversely affect the reaction, such as N,N-dimethylformamide, dimethyl sulfoxide, N-methylpyrolidone, tetrahydrofuran, ethanol, 1,4-dioxane, an optionally mixed solvents therefrom and the like, or without solvent, in the presence of an organic base such as pyridine, triethylamine, diisopropylethylamine and the like or an inorganic base such as sodium hydride, potassium carbonate, sodium carbonate, sodium hydroxide, potassium hydroxide, potassium tert-butoxide, sodium alkoxide, butyllithium and the like at −20° C. to 170° C. for 1 to 24 hr to give the above-mentioned compound of the formula (11a).

In particular, of the compounds of the formula (11a), a compound wherein $R^{13}$ is alkyl can be also obtained by keeping a compound wherein $R^{13}$ is hydrogen with an alkyl halide of the formula (6) to be mentioned later, in a solvent that does not adversely affect the reaction, such as N,N-dimethylformamide, dimethyl sulfoxide, N-methylpyrolidone, tetrahydrofuran, 1,4-dioxane, an optionally mixed solvent therefrom and the like, or without solvent, in the presence of an organic base such as pyridine, triethylamine, diisopropylethylamine and the like, or an inorganic base such as sodium hydride, potassium carbonate, sodium carbonate, sodium hydroxide, potassium hydroxide, potassium tert-butoxide, sodium alkoxide, butyllithium, lithium diisopropylamine and the like at room temperature to 170° C. for 1 to 24 hr.

The obtained compound of the formula (11) is kept with hydrogen at normal pressure to 100 atm, in a solvent that does not adversely affect the reaction such as ethanol, methanol, ethyl acetate, dimethylformamide, acetic acid, water, an optionally mixed solvent therefrom and the like, or without solvent, in the presence of a suitable metal catalyst such as palladium-carbon, palladium black, palladium hydroxide, Raney nickel, platinium oxide and the like at room temperature to 150° C. for 1 to 24 hr to give a compound of the formula (14)

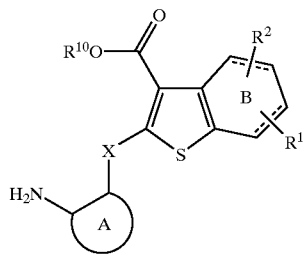

(14)

wherein each symbol is as defined above.

The compound of the formula (14) can be also obtained by keeping a compound of the formula (11) with a suitable inorganic reagent such as iron, zinc, tin(II) chloride and the like, in a solvent that does not adversely affect the reaction, such as ethanol, methanol, 1,4-dioxane, dimethylformamide, acetic acid, water, an optionally mixed solvent therefrom and the like, in the presence of a suitable acid such as hydrochloric acid, acetic acid and the lik at −20° C. to 150° C. for 1 to 24 hr.

In addition, of the compounds of the formula (14), a compound wherein X is S or O can be also obtained by keeping a compound of the formula (9) with a compound of the formula (25)

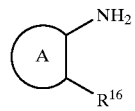

(25)

wherein $R^{16}$ is OH or SH and ring A is as defined above, in a solvent that does not adversely affect the reaction, such as N,N-dimethyformamide, dimethyl sulfoxide, N-methylpyrolidone, tetrahydrofuran, ethanol, 1,4-dioxane, an optionally mixed solvent therefrom and the like, or without solvent, in the presence of an organic base such as pyridine, triethylamine, diisopropylethylamine and the like or an inorganic base such as sodium hydride, potassium carbonate, sodium carbonate, sodium hydroxide, potassium hydroxide, potassium tert-butoxide, sodium alkoxide, butyllithium and the like at −20° C. to 150° C. for 1 to 24 hr.

The obtained compound of the formula (14) is kept with a compound of the formula (5) in a solvent that does not adversely affect the reaction, such as anisole, toluene, xylene, mesitylene, nitrobenzene, 1,2-dichloroethane, an optionally mixed solvent therefrom and the like, or without solvent, in the presence of a suitable Lewis acid such as titanium tetrachloride, thin tetrachloride, aluminium chloride and the like at room temperature to 170° C. for 1 to 24 hr to give a compound of the formula (IA).

Method 4:

A compound of the formula (IAa)

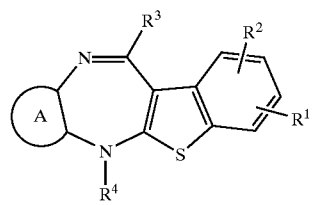

(IAa)

wherein each symbol is as defined above, which is a compound of the formula (IA) wherein X is N-$R^4$, can be also obtained by keeping a benzothiophene compound of the formula (IAb)

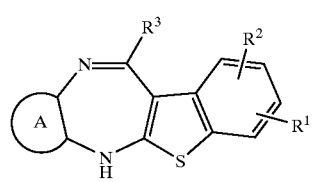

(IAb)

wherein each symbol is as defined above, with an alkyl halide of the formula (6)

Hal-$R^4$ (6)

wherein Hal is halogen and $R^4$ is as defined above, in a solvent that does not adversely affect the reaction, such as N,N-dimethylformamide, dimethyl sulfoxide, N-methylpyrolidone, tetrahydrofuran, 1,4-dioxane, an optionally mixed solvent therefrom and the like, or without solvent, in the presence of an organic base such as pyridine, triethylamine, diisopropylethylamine and the like, or an inorganic base such as sodium hydride, potassium carbonate, sodium carbonate, sodium hydroxide, potassium hydroxide, potassium tert-butoxide, sodium alkoxide, butyllithium and the like at room temperature to 170° C. for 1 to 24 hr.

Method 5:

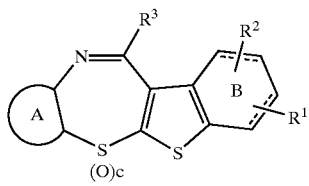

(IAc)

A compound of the formula (IAc) wherein c is 1 or 2 and other symbols are as defined above, which is a compound of the formula (IA) wherein X is SO or $SO_2$, can be also obtained by keeping a benzothiophene compound of the formula (IAd) wherein each symbol is as defined above, with an oxidizing agent such as hydrogen peroxide, m-chloroperbenzoic acid, sodium periodate, sodium perbromate and the like, in a solvent that does not adversely affect the reaction, such as water, ethanol, acetic acid, formic acid, dichloromethane, chloroform, an

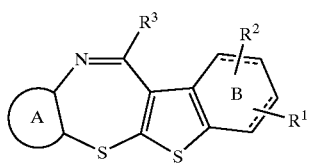

(IAd)

optionally mixed solvent therefrom and the like, or without solvent, at −78° C. to 120° C. for 1 to 24 hr.

Method 6: Synthetic Method of Compound of Formula (IIA)

A compound of the formula (14) is kept with an organic base, such as pyridine, triethylamine, diisopropylethylamine and the like, or an inorganic base, such as sodium hydride, potassium carbonate, sodium carbonate, sodium hydroxide, potassium hydroxide, potassium tert-butoxide, sodium alkoxide, butyllithium and the like, or a suitable Lewis acid, such as titanium tetrachloride, thin tetrachloride, aluminium chloride, boron trifluoride and the like, or a suitable acid, such as sulfuric acid, phosphoric acid and the like, in a solvent that does not adversely affect the reaction, such as dichloromethane, chloroform, tetrahydrofuran, dimethyl sulfoxide, N,N-dimethylformamide, benzene, toluene, xylene, an optionally mixed solvent therefrom and the like, at room temperature to 170° C. for 1 to 24 hr to give a compound of the formula (IIA).

A compound of the formula (14) is kept with a suitable inorganic base, such as sodium hydroxide, potassium hydroxide, barium hydroxide and the like, in a solvent that does not adversely affect the reaction, such as methanol, ethanol, water, tetrahydrofuran, 1,4-dioxane, an optionally mixed solvent therefrom and the like, at room temperature to 150° C. for 1 to 24 hr to give a compound of the formula (15)

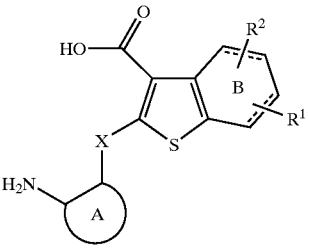

(15)

wherein each symbol is as defined above. The obtained compound of the formula (15) is kept with a suitable condensing agent, such as dicyclohexylcarbodiimide, diisopropylcarbodiimide, N-ethyl-N'-3-dimethylaminopropylcarbodiimide, diethylphosphoryl azide, diphenylphosphoryl azide and the like, in a solvent that does not adversely affect the reaction, such as benzene, toluene, xylene, hexane, ethyl acetate, diethyl ether, tetrahydrofuran, dioxane, chloroform, dichloromethane, 1,2-dichloroethane, N,N-dimethylformamide, dimethyl sulfoxide, N-methylpyrolidone, pyridine, an optionally mixed solvent therefrom and the like, at room temperature to 100° C. for 10 min to 24 hr to give a compound of the formula (IIA).

Method 7: Synthetic Method of Compound of Formula (IIA)

A compound of the formula (16)

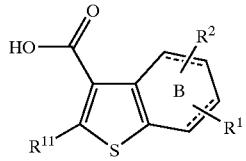

(16)

wherein each symbol is as defined above, is kept with a suitable chlorinating agent such as thionyl chloride, phosphorus oxychloride, phosphorus pentachloride, oxalyl chloride and the like in a solvent that does not adversely affect the reaction such as benzene, toluene, xylene, chloroform, 1,2-dichloroethane, an optionally mixed solvent therefrom and the like, or without solvent, at room temperature to 170° C. for 1 to 24 hr to give a compound of the formula (17)

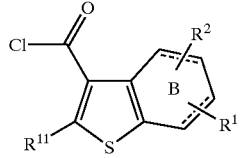

(17)

wherein each symbol is as defined above. The obtained compound of the formula (17) is kept with a compound of the formula (18)

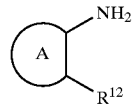

(18)

wherein each symbol is as defined above, in a solvent that does not adversely affect the reaction such as benzene, toluene, xylene, hexane, ethyl acetate, diethyl ether, tetrahydrofuran, dioxane, chloroform, dichloromethane, 1,2-dichloroethane, N,N-dimethylformamide, dimethyl sulfoxide, N-methylpyrolidone, pyridine, an optionally mixed solvent therefrom and the like, or without solvent, in the presence of an organic base, such as pyridine, triethylamine, diisopropylethylamine and the like, or an inorganic base, such as potassium carbonate, sodium carbonate, sodium hydroxide, potassium hydroxide and the like at room temperature to 170° C. for 10 min to 24 hr to give a compound of the formula (19)

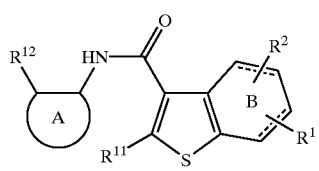

(19)

wherein each symbol is as defined above.

A compound of the formula (19) can be also obtained by keeping a compound of the formula (16) with a compound of the formula (18) in a solvent that does not adversely affect the reaction such as benzene, toluene, xylene, hexane, ethyl acetate, diethyl ether, tetrahydrofuran, dioxane, chloroform, dichloromethane, 1,2-dichloroethane, N,N-dimethylformamide, dimethyl sulfoxide, N-methylpyrolidone, pyridine, an optionally mixed solvent therefrom and the like and a suitable condensing agent, such as dicyclohexylcarbodiimide, diisopropylcarbodiimide, N-ethyl-N'-3-dimethylaminopropylcarbodiimide, diethylphosphoryl azide, diphenylphosphoryl azide and the like at room temperature to 100° C. for 10 min to 24 hr.

The obtained compound of the formula (19) is kept in a solvent that does not adversely affect the reaction, such as methanol, ethanol, N,N-dimethylformamide, dimethyl sulfoxide, N-methylpyrolidone, hexamethylphosphorous triamide, benzene, toluene, xylene, chloroform, dichloroethane and the like, an optionally mixed solvent therefrom and the like, in the presence of an organic base, such as pyridine, triethylamine, N,N-diisopropylethylamine and the like, or an inorganic base, such as potassium carbonate, sodium carbonate, sodium hydroxide, potassium hydroxide, sodium hydride and the like at room temperature to 170° C. for 10 min to 24 hr to give a compound of the formula (IIA).

Method 8:

A compound of the formula (IIAa)

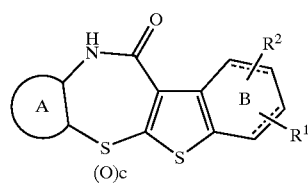

(IIAa)

wherein each symbol is as defined above, which is a compound of the formula (IIA) wherein X is SO or SO$_2$, can be obtained by keeping a benzothiophene compound of the formula (IIAb)

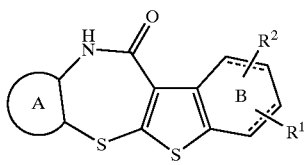

(IIAb)

wherein each symbol is as defined above, with an oxidizing agent, such as hydrogen peroxide, m-chloroperbenzoic acid, sodium periodate, sodium perbromate and the like, in a solvent that does not adversely affect the reaction, such as water, ethanol, acetic acid, formic acid, dichloromethane, chloroform, an optionally mixed solvent therefrom and the like, or without solvent, at −78° C. to 120° C. for 1 to 24 hr.

Method 9:

A compound of the formula (IIAc)

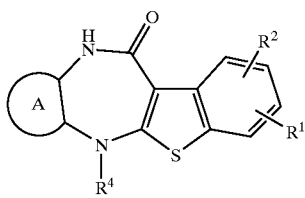

(IIAc)

wherein each symbol is as defined above, which is a compound of formula (IIA) wherein X is N-R$^4$, can be also obtained by, for example, keeping a benzothiophene compound of the formula (IIAd)

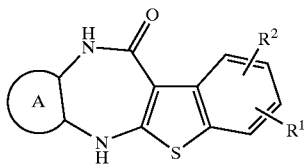

(IIAd)

wherein each symbol is as defined above, with an alkyl halide of the formula (6), in a solvent that does not adversely affect the reaction, such as N,N-dimethylformamide, dimethyl sulfoxide, N-methylpyrolidone, tetrahydrofuran, 1,4-dioxane, an optionally mixed solvent therefrom and the like, or without solvent, in the presence of an organic base, such as pyridine, triethylamine, diisopropylethylamine and the like, or an inorganic base, such as sodium hydride, potassium carbonate, sodium carbonate, sodium hydroxide, potassium hydroxide, potassium tert-butoxide, sodium alkoxide, butyllithium, lithium diisopropylamide and the like at room temperature to 170° C. for 1 to 24 hr.

Method 10:

A compound of the formula (IIAe)

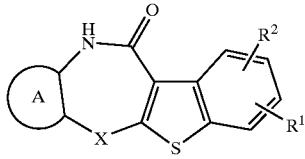

(IIAe)

wherein each symbol is as defined above provided that a compound wherein X is NH is excluded, which is a compound of formula (IIA) wherein ring B is a benzene ring, can be also obtained by keeping a 1,2,3,4-tetrahydrobenzothiophene compound of the formula (IIAf)

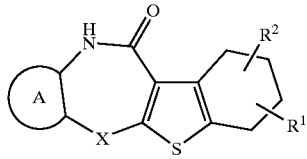
(IIAf)

wherein each symbol is as defined above, with a suitable oxidizing agent, such as sulfur, N-bromosuccinimide, N-chrolosuccinimide, N-iodosuccinimide, dichlorodicyano-p-benzoquinone, or a suitable noble metallic catalyst, such as palladium-carbon, palladium hydroxide, palladium black, platinum oxide and the like, in a solvent that does not adversely affect the reaction, such as benzene, toluene, xylene, mesitylene, chloroform, carbon tetrachloride, 1,4-dioxane, an optionally mixed solvent therefrom and the like, or without solvent at 0° C. to 250° C. for 1 to 48 hr.

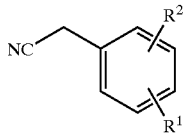
(IIAg)

wherein each symbol is as defined above, which is a compound of formula (IIA) wherein substituent on ring A is amino, can be obtained by keeping a compound of the formula (IIAh)

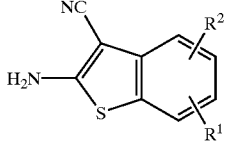
(IIAh)

wherein each symbol is as defined above, which is a compound of formula (IIA) wherein a substituent on ring A is nitro, with hydrogen, in a solvent that does not adversely affect the reaction, such as methanol, ethanol, ethyl acetate, dioxane, benzene, toluene, xylene, diethyl ether, chloroform, 1,2-dichloroethane, an optionally mixed solvent therefrom and the like, using palladium-carbon, palladium hydroxide, platinum oxide and the like as a catalyst at 0°C. to 100° C. and from normal pressure to 100 atm for 10 min to 24 hr.

Method 12:
A compound of the formula (IIAi)

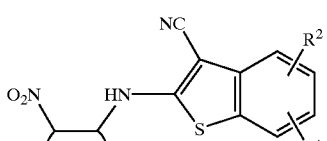
(IIAi)

wherein $R^{15}$ is fluorine, chlorine, bromine, iodine or cyano and other symbols are as defined above, which is a compound of formula (IIA) wherein substituent on ring A is cyano or halogen, can be obtained by diazotizing a compound of the formula (IIAg) in a solvent that does not adversely affect the reaction, such as water, diluted hydrochloric acid and the like and using sodium nitrite and the like at −10° C. to room temperature and keeping with fluoroboric acid, hydrogen fluoride-pyridine, sodium chloride, cuprous chloride, sodium bromide, cuprous bromide, sodium iodide, potassium iodide and the like at −10° C. to 100° C.

Method 13: Synthetic Method of Compound of Formula (IA) Wherein X is NH and Bond Shown by Dotted Line and Solid Line in B Ring is Double Bond Using a benzylcyanide compound of the formula (20)

(20)

wherein each symbol is as defined above, as a starting material and according to the method described in Japanese Patent Unexamined Publication No. 7-89965 to give a benzothiophene compound of the formula (21)

(21)

wherein each symbol is as defined above.

The obtained compound of the formula (21) is kept with a compound of the formula (13) in a solvent that does not adversely affect the reaction, such as N,N-dimethylformamide, dimethyl sulfoxide, N-methylpyrolidone, tetrahydrofuran, ethanol, 1,4-dioxane, an optionally mixed solvent therefrom and the like, or without solvent, in the presence of an organic base, such as pyridine, triethylamine, diisopropylethylamine and the like, or inorganic base, such as sodium hydride, potassium carbonate, sodium carbonate, sodium hydroxide, potassium hydroxide, potassium tert-butoxide, sodium alkoxide, butyl-lithium or the like at −50° C. to 170° C. for 1 to 24 hr to give a compound of the formula (22)

(22)

wherein each symbol is as defined above.

The obtained compound of the formula (22) is kept with a suitable reducing agent such as iron, zinc, tin(II) chloride and the like, in a solvent that does not adversely affect the reaction, such as ethanol, methanol, 1,4-dioxane, dimethylformamide, acetic acid, water, an optionally mixed solvent therefrom and the like, in the presence of a suitable acid, such as hydrochloric acid, sulfuric acid, nitric acid, phosphoric acid, acetic acid and the like at −20° C. to 150° C. for 1 to 24 15 hr to give a compound of the formula (23)

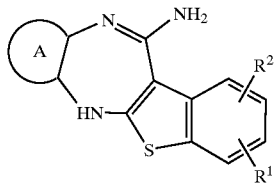

(23)

wherein each symbol is as defined above or a salt thereof with an inorganic acid, such as hydrochloric acid, sulfuric acid, nitric acid, phosphoric acid and the like.

A compound of the formula (23) can be obtained by keeping a compound of the formula (22) with hydrogen from normal pressure to 100 atm in a solvent that does not adversely affect the reaction, such as ethanol, methanol, ethyl acetate, dimethylformamide, acetic acid, water, an optionally mixed solvent therefrom and the like or without solvent, in the presence of a suitable metallic catalyst, such as palladium-carbon, palladium black, palladium hydroxide, Raney nickel, platinium oxide and the like at room temperature to 150° C. for 1 to 24 hr, or by keeping a compound of the formula (24)

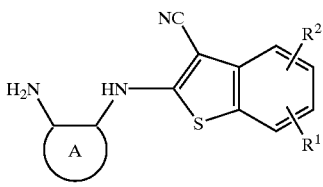

(24)

wherein each symbol is as defined above, which is obtained by keeping with a suitable reducing agent, such as sodium hydrosulfite, iron, zinc, tin(II) chloride and the like in the presence of hydrochloric acid, acetic acid and the like, or under neutral conditions, at −20° C. to 150° C. for 1 to 24 hr is kept in a solvent that does not adversely affect the reaction, such as benzene, toluene, xylene, dimethyl sulfoxide, N,N-dimethylformamide, 1,4-dioxane, ethanol, methanol, acetic acid, water, an optionally mixed solvent therefrom and the like, in the presence or absence of an suitable inorganic acid, such as hydrochloric acid, sulfuric acid, nitric acid, phosphoric acid and the like, at room temperature to 180° C. for 1 to 24 hr.

The obtained compound of the formula (23) is kept with a compound of the formula (1), (2), (3), (26), (27), (28), (29) or (30) in a solvent that does not adversely affect the reaction, such as benzene, toluene, xylene, dimethyl sulfoxide, N,N-dimethylformamide, an optionally mixed solvent therefrom and the like, or without solvent, in the presence of a suitable organic base, such as pyridine, triethylamine, diisopropylethylamine and the like, or inorganic base, such as potassium carbonate, sodium carbonate and the like, or in the absence of a base at room temperature to 180° C. for 1 to 20 hr to give a compound of the formula (IA) wherein X is NH and the bond shown by a dotted line and a solid line in the B ring is a double bond.

Method 14 Compounds of Formulas (IAe) and (IAf)

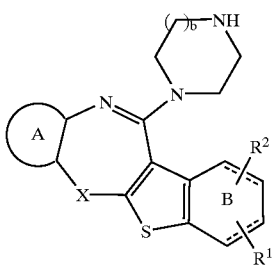

(IAe)

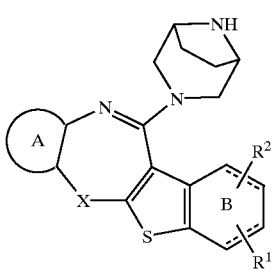

(IAf)

wherein each symbol is as defined above, provided that when X is NH, the bond shown by a dotted line and a solid line is not a single bond, which are the compounds of the formula (IA) wherein $R^3$ is of formula (2) or (3) and $R^8$ or $R^9$ is hydrogen, can be also obtained by keeping a compound wherein $R^3$ is alkoxycarbonyl or acyl of the formula (2a), (2b), (3a) or (3b)

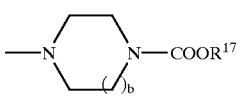

(2a)

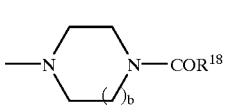

(2b)

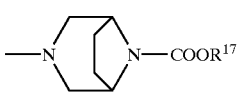

(3a)

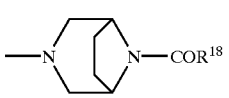

(3b)

wherein $R^{17}$ is alkyl or aralkyl, $R^{18}$ is alkyl or aryl and b is as defined above, in a solvent that does not adversely affect the reaction, such as ethanol, methanol, 1,4-dioxane, tetrahydrofuran, benzene, toluene, water, an optionally mixed solvent therefrom and the like or without using a solvent, in the presence of an inorganic acid such as hydrochloric acid, sulfuric acid and the like or an organic acid such as acetic acid, trifluoroacetic acid, p-toluenesulfonic acid and the like at 0° C. to 150° C. for 1 to 18 hr.

The compounds (IAe) and (IAf) can be also obtained by keeping compounds of the formulas (2c) and (3c)

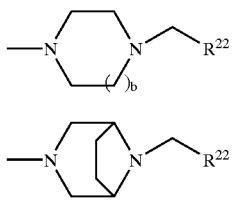

(2c)

(3c)

wherein $R^{22}$ is aryl and b is as defined above, with hydrogen at normal pressure to 100 atm in a solvent that does not adversely affect the reaction, such as ethanol, methanol, ethyl acetate, dimethylformamide, acetic acid, water, an optionally mixed solvent therefrom and the like, or without solvent, in the presence of a suitable metallic catalyst, such as palladium-carbon, palladium black, palladium hydroxide, Raney nickel, platinium oxide and the like at room temperature to 150° C. for 1 to 24 hr.

Method 15: Compounds of Formulas (IAg) and (IAh)

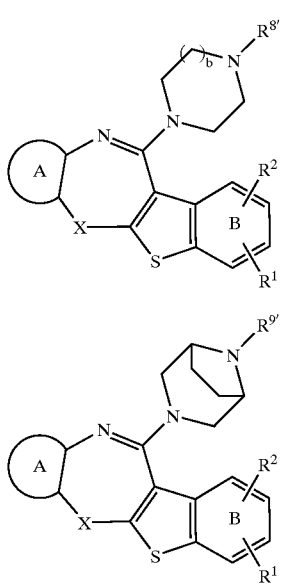

(IAg)

(IAh)

wherein $R^{8'}$ and $R^{9'}$ are each acyl or alkoxycarbonyl and other symbols are as defined above, provided that when X is NH and the bond shown by a dotted line and a solid line is not a single bond, which are the compounds of the formula (IA) wherein $R^3$ is formula (2) or (3) and $R^8$ or $R^9$ is acyl or alkoxycarbonyl, can be obtained by keeping compounds (IAe) and (IAf) ($R^8$ or $R^9$ is hydrogen) with a suitable acylating agent, such as acyl halide of the formula (31)

 (31)

wherein Hal is halogen and $R^{19}$ is alkyl or aryl, or acid anhydride of the formula (32)

 (32)

wherein $R^{19}$ is as defined above, or ester halide of the formula (33)

 (33)

wherein Hal is halogen and $R^{20}$ is alkyl or aralkyl as an alkoxycarbonylating agent, in a solvent that does not adversely affect the reaction such as benzene, toluene, xylene, chloroform, 1,4-dioxane, tetrahydrofuran, an optionally mixed solvent therefrom and the like, or without solvent, in the presence of a basic reagent, such as pyridine, triethylamine, N, N-dimethylaminopyridine, sodium hydride, potassium carbonate, sodium hydroxide, potassium tert-butoxide, sodium alkoxide, butyllithium, lithium diisopropylamine and the like, at −50 to 150° C. for 10 min to 15 hr.

Method 16: Compounds of Formulas (IAi) and (IAj)

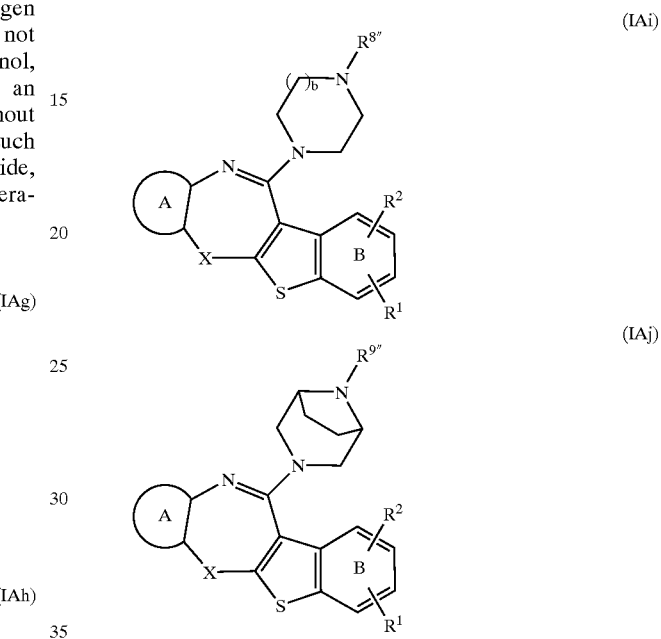

(IAi)

(IAj)

wherein $R^{8''}$ and $R^{9''}$ are each alkyl, cycloalkyl, aralkyl, hydroxyalkyl, hydroxyalkoxyalkyl, aminoalkyl, monoalkylaminoalkyl, dialkylaminoalkyl or alkoxyalkyl and other symbols are as defined above, provided that when X is NH, the bond shown by a dotted line and a solid line is not a single bond, which are the compounds of the formula (IA) wherein $R^3$ is of formula (2) or (3) and $R^8$ or $R^9$ is alkyl, cycloalkyl, aralkyl, hydroxyalkyl, hydroxyalkoxyalkyl, aminoalkyl, monoalkylaminoalkyl, dialkylaminoalkyl or alkoxyalkyl, can be obtained by keeping compounds (IAe) and (IAf) ($R^8$ or $R^9$ is hydrogen) with a suitable alkylating agent, such as compound of the formula (34)

 (34)

wherein Hal is halogen and $R^{21}$ is alkyl, cycloalkyl, aralkyl, hydroxyalkyl, hydroxyalkoxyalkyl, aminoalkyl, monoalkylaminoalkyl, dialkylaminoalkyl or alkoxyalkyl in a solvent that does not adversely affect the reaction, such as benzene, toluene, xylene, chloroform, 1,4-dioxane, tetrahydrofuran, an optionally mixed solvent therefrom and the like, or without solvent, in the presence of a suitable basic reagent such as pyridine, triethylamine, N,N-dimethylaminopyridine, sodium hydride, potassium carbonate, sodium hydroxide, potassium tert-butoxide, sodium alkoxide, butyllithium, lithium diisopropylamine and the like at −50 to 200° C. for 10 min to 24 hr.

Method 17:

Of the compounds of the formula (IA), a compound wherein $R^3$ is of the formula (27), (28), (29) or (30) can be obtained by keeping the corresponding compound (1), (2), (3) or (26) with a suitable oxidizing agent, such as aqueous hydrogen peroxide, m-chloroperbenzoic acid, tert-butyl hydroperoxide and the like in a solvent that does not adversely affect the reaction such as methylene chloride, chloroform, 1,2-dimethoxyethane, benzene, toluene, diethyl ether, tetrahydrofuran, 1,4-dioxane, methanol, ethanol, water, an optionally mixed solvent therefrom and the like at −30 to 130° C. for 10 min to 12 hr.

Method 18:

A compound of the formula (IIA) wherein X is O, S, SO or $SO_2$ and the bond shown by a dotted line and a solid line in the B ring is a double bond can be also obtained by keeping a compound of the formula (IIA) wherein X is O, S, SO or $SO_2$ and the bond shown by a dotted line and a solid line in the B ring is a single bond in a solvent that does not adversely affect the reaction, such as benzene, toluene, xylene, mesitylene, dichloromethane, chloroform, ethyl acetate, methanol, ethanol, tetrahydrofuran, 1,4-dioxane, dimethyl sulfoxide, N,N-dimethylformamide, an optionally mixed solvent therefrom and the like, in the presence of a suitable oxidizing agent, such as 2,3-dichloro-5,6-dicyano-1,4-benzoquinone, chloranil, manganese dioxide, nickel peroxide, palladium-carbon, lead tetraacetate and the like at room temperature to 200° C. for 1 to 24 hr.

Method 19: Synthetic Method of Compound of Formula (IB)

A thienobenzoxazepinone compound of the formula (IIB)

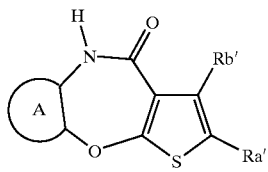

(IIB)

wherein each symbol is as defined above, is kept with a suitable chlorinating agent such as thionyl chloride, phosphorus oxychloride, phosphorus pentachloride and the like in a suitable solvent, such as a solvent that does not adversely affect the reaction (e.g., benzene, toluene, xylene, chloroform, 1,2-dichloroethane, an optionally mixed solvent therefrom and the like), or without solvent, at room temperature to 170° C. for 1 to 24 hr to give a compound of the formula (4B)

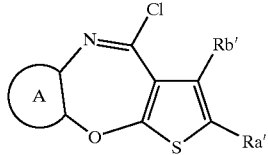

(4B)

wherein each symbol is as defined above. Then, a compound of the formula (4B) is kept with a compound of the formula (5)

$H-R^3$ (5)

wherein $R^3$ is as defined above, in a suitable solvent, such as a solvent that does not adversely affect the reaction (e.g., benzene, toluene, xylene, chloroform, 1,2-dichloroethane, an optionally mixed solvent therefrom and the like), or without solvent, at room temperature to 170° C. for 1 to 24 hr to give a compound of the formula (IB).

Method 20: Synthetic Method of Compound of Formula (IBa)

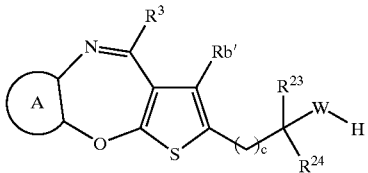

(IBa)

wherein W is an oxygen atom or nitrogen atom bonded with hydrogen or one $C_1$–$C_5$ alkyl, $R^{23}$ and $R^{24}$ are the same or different and each is hydrogen, $C_1$–$C_4$ alkyl and the like, c is an integer of 0 to 4, and other symbols are as defined above, which is a compound of formula (IB) (Ra' is hydroxyalkyl, aminoalkyl or monoalkylaminoalkyl)

For example, a compound of the formula (IBb) (Ra' is acyloxyalkyl or acylaminoalkyl), which is synthesized according to Method 19

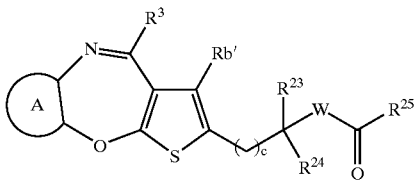

(IBb)

wherein $R^{25}$ is hydrogen or alkyl having 1 to 4 carbon atoms, and the like and other symbols are as defined above, is kept with a base such as sodium hydroxide, potassium hydroxide, ammonia and the like or an acid such as hydrochloric acid, hydrobromic acid, acetic acid, formic acid, sulfuric acid and the like, in water or in a mixed solvent of water and a suitable solvent, such as methanol, ethanol, pyridine, dioxane and the like at room temperature to 100° C. for 10 min to 24 hr to give a compound of the formula (IBa).

Method 21: Synthetic Method of Compound of Formula (IBc)

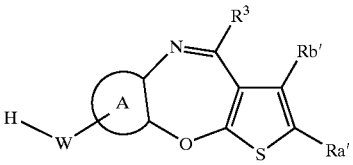

(IBc)

wherein each symbol is as defined above, which is a compound of the formula (IB) wherein substituent on ring A is hydroxy, amino or monoalkyamino For example, a compound of the formula (IBd) which is a compound of the formula (IB) wherein substituent on ring A is acyloxy or acylamino

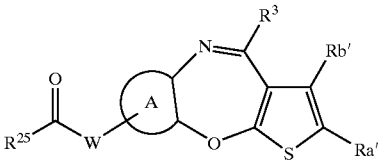

(IBd)

wherein each symbol is as defined above, is kept with a base such as sodium hydroxide, potassium hydroxide, ammonia and the like or an acid such as hydrochloric acid, hydrobromic acid, acetic acid, formic acid, sulfuric acid and the like in water or a mixed solvent of water and a suitable solvent, such as methanol, ethanol, pyridine, dioxane and the like, at room temperature to 100° C. for 10 min to 24 hr to give a compound of the formula (IBc).

Method 22: Synthetic Method of Compound of Formula (IBe)

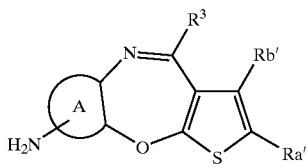
(IBe)

wherein each symbol is as defined above, which is the compound of formula (IB) wherein substituent on ring A is amino A compound of the formula (IBf)

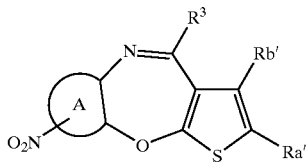
(IBf)

wherein each symbol is as defined above, which is the compound of the formula (IB) wherein substituent on ring A is nitro, and which is synthesized according to Method 19, is kept with hydrogen in a suitable solvent, such as a solvent that does not adversely affect the reaction (e.g., methanol, ethanol, ethyl acetate, dioxane, benzene, toluene, xylene, diethyl ether, chloroform, 1,2-dichloroethane, an optionally mixed solvent therefrom and the like), using palladium-activated carbon, palladium hydroxide, platinium oxide and the like as a catalyst, at 0° C. to 100° C. at normal pressure to 100 atm for 10 min to 24 hr, to give a compound of the formula (IBe).

Method 23: Synthetic Method of Compound of Formula (IIB)

2-Halogeno-3-thiophenecarboxylic acid derivative of the formula (35)

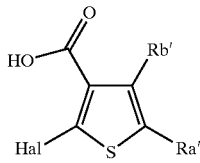
(35)

wherein Hal is halogen and other symbols are as defined above, is kept with a suitable chlorinating agent, such as thionyl chloride, phosphorus oxychloride, phosphorus pentachloride, oxalyl chloride and the like in a suitable solvent, such as a solvent that does not adversely affect the reaction (e.g., benzene, toluene, xylene, chloroform, 1,2-dichloroethane, an optionally mixed solvent therefrom and the like), or without solvent, at room temperature to 170° C. for 1 to 24 hr to give a compound of the formula (36)

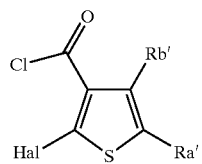
(36)

wherein each symbol is as defined above.

The obtained compound of the formula (36) is kept with a compound of the formula (37)

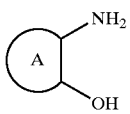
(37)

wherein ring A is as defined above, in a suitable solvent such as a solvent that does not adversely affect the reaction (e.g., benzene, toluene, xylene, hexane, ethyl acetate, diethyl ether, tetrahydrofuran, dioxane, chloroform, dichloromethane, 1,2-dichloroethane, N,N-dimethylformamide, dimethyl sulfoxide, N-methylpyrolidone, pyridine, an optionally mixed solvent therefrom and the like), or without solvent, in the presence of an organic base, such as pyridine, triethylamine, diisopropylethylamine and the like, or an inorganic base, such as potassium carbonate, sodium carbonate, sodium hydroxide, potassium hydroxide and the like, at room temperature to 170° C. for 10 min to 24 hr to give a compound of the formula (38)

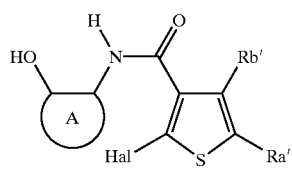
(38)

wherein each symbol is as defined above.

The compound of the formula (38) can be also obtained by keeping a compound of the formula (35) and a compound of the formula (37) in a suitable solvent, such as a solvent that does not adversely affect the reaction (e.g., benzene, toluene, xylene, hexane, ethyl acetate, diethyl ether, tetrahydrofuran, dioxane, chloroform, dichloromethane, 1,2-dichloroethane, N,N-dimethylformamide, dimethyl sulfoxide, N-methylpyrolidone, pyridine, an optionally mixed solvent therefrom and the like), together with a suitable condensing agent, such as dicyclohexylcarbodiimide, diisopropylcarbodiimide, N-ethyl-N'-3-dimethylaminopropylcarbodiimide, diethylphosphoryl azide, diphenylphosphoryl azide and the like at room temperature to 100° C. for 10 min to 24 hr.

The obtained compound of the formula (38) is kept in suitable solvent, such as a solvent that does not adversely affect the reaction (e.g., methanol, ethanol, N,N-dimethylformamide, dimethyl sulfoxide, N-methylpyrolidone, hexamethylphosphorus triamide, benzene, toluene, xylene, chloroform, dichloroethane and the like, an optionally mixed solvent therefrom and the like), in the presence of an organic base, such as pyridine, triethylamine, N,N-diisopropylethylamine and the like, or an inorganic base, such as potassium carbonate, sodium carbonate, sodium hydroxide, potassium hydroxide, sodium hydride and the like or metal alkoxide or sodium ethoxide, sodium methoxide, potassium tert-butoxide and the like at room temperature to 170° C. for 10 min to 24 hr to give a compound of the formula (IIB).

Method 24: Synthetic Method of Compound of Formula (IIBa)

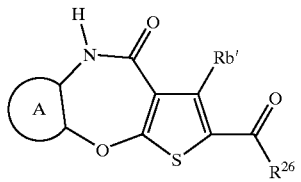

(IIBa)

wherein $R^{26}$ is alkyl having 1 to 4 carbon atoms such as methyl, ethyl, propyl, butyl and the like and other symbols are as defined above, which is a compound of formula (IIB) wherein Ra' is acyl other than formyl A compound of the formula (IIBb) which is a compound of the formula (IIB) wherein Ra' is hydrogen and synthesized according to Method 23

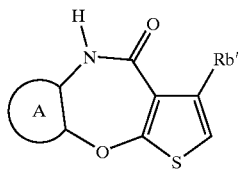

(IIBb)

wherein each symbol is as defined above, is kept with a compound of the formula (39)

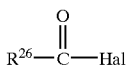

(39)

wherein each symbol is as defined above or a compound of the formula (40)

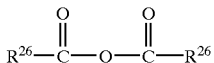

(40)

wherein $R^{26}$ is as defined above, in the presence of an aluminium chloride and the like in a suitable solvent, such as a solvent that does not adversely affect the reaction (e.g., nitrobenzene, hexane, chloroform, 1,2-dichloroethane and the like, an optionally mixed solvent therefrom and the like), from 0° C. to 100° C. for 10 min to 24 hr to give a compound of the formula (IIBa).

Method 25: Synthetic Method of Compound of Formula (IIBc)

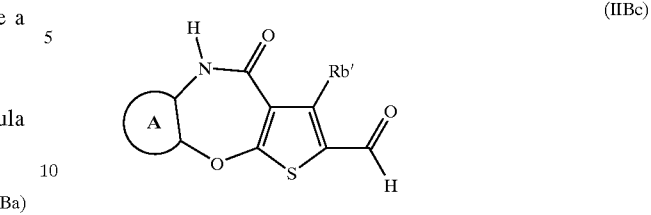

(IIBc)

wherein each symbol is as defined above, which is a compound of formula (IIB) wherein Ra' is formyl A compound of the formula (IIBc) can be obtained by keeping a compound of the formula (IIBb) with aluminium chloride and the like in a suitable solvent, such as a solvent that does not adversely affect the reaction (e.g., nitrobenzene, hexane, chloroform, 1,2-dichloroethane and the like, an optionally mixed solvent therefrom and the like), in the presence of dichloromethylmethyl ether and the like at 0° C. to 100° C. for 10 min to 24 hr.

In addition, a compound of the formula (IIBc) can be also obtained by keeping a compound of the formula (IIBb) with N,N-dimethylformamide, N-methylformanilide, N-methylmorpholine, N,N-diisopropylformamide and the like, in a suitable solvent, such as a solvent that does not adversely affect the reaction (e.g., N,N-dimethylformamide, dimethyl sulfoxide, N-methylpyrolidone, hexamethylphosphorous triamide, benzene, toluene, xylene, chloroform, dichloroethane and the like, an optionally mixed solvent therefrom and the like), or without solvent, in the presence of an halogenating agent such as phosphorus oxychloride, phosgene, oxalyl chloride, thionyl chloride and the like, at 0° C. to 100° C. for 10 min to 24 hr.

Method 26: Synthetic Method of Compound of Formula (IIBd)

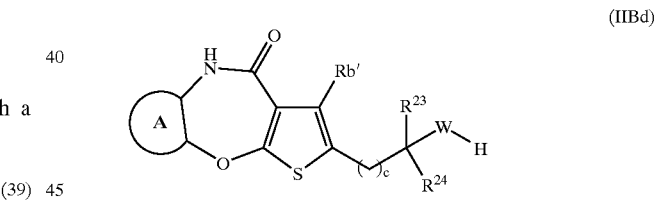

(IIBd)

wherein each symbol is as defined above, which is a compound of formula (IIB) wherein Ra' is hydroxyalkyl, aminoalkyl or monoalkylaminoalkyl A compound of the formula (IIBe) (IIB wherein Ra' is acyloxyalkyl or acylaminoalkyl)

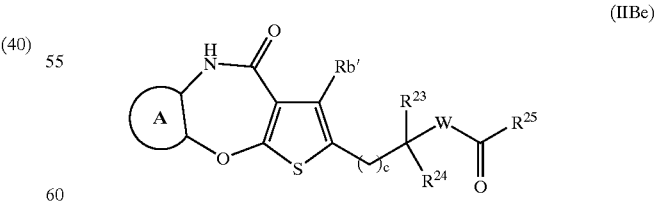

(IIBe)

wherein each symbol is as defined above, synthesized according to the Method 36 to be mentioned later is kept with a base such as sodium hydroxide, potassium hydroxide, ammonia and the like or an acid such as hydrochloric acid, hydrobromic acid, acetic acid, formic acid, sulfuric acid and the like in a suitable solvent such as water and a mixed solvent of water and a suitable solvent (e.g., methanol, ethanol, pyridine, dioxane and the like), at room temperature to 100° C. for 10 min to 24 hr to give a compound of the formula (IIBd).

Method 27: Synthetic Method of Compound of Formula (IIBf):

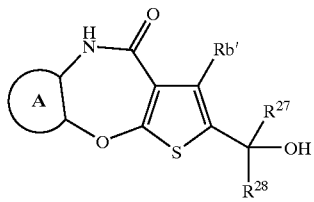

(IIBf)

wherein $R^{27}$ and $R^{28}$ are the same or different and each is alkyl having 1 to 4 carbon atoms and other symbols are as defined above, from among the compounds of formula (IIB) wherein Ra' is hydroxyalkyl For example, a compound of the formula (IIB g)

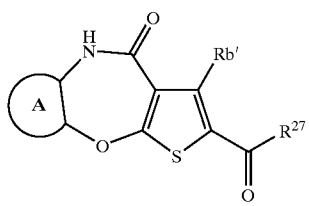

(IIBg)

wherein each symbol is as defined above, is kept with an alkyl metal compound such as a compound of the formula (41)

 (41)

R$^{28}$MgBr wherein $R^{28}$ is alkyl having 1 to 4 carbon atoms, and the like, in a suitable solvent, such as a solvent that does not adversely affect the reaction (e.g., benzene, toluene, xylene, diethyl ether, tetrahydrofuran, chloroform, dichloroethane, an optionally mixed solvent therefrom and the like), at 0° C. to 100° C. for 10 min to 24 hr to give a compound of the formula (IIBf).

Method 28: Synthetic Method of Compound of Formula (IIBh)

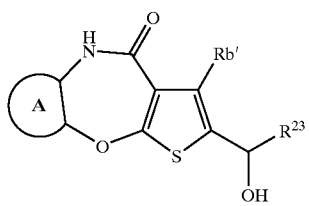

(IIBh)

wherein each symbol is as defined above, from among the compounds of formula (IIB) wherein Ra' is hydroxyalkyl For example, a compound of the formula (IIBi)

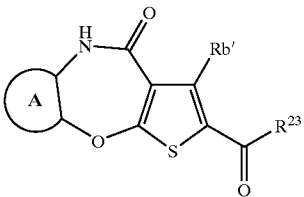

(IIBi)

wherein each symbol is as defined above is kept with sodium boron hydride, lithium aluminium hydride and the like in a suitable solvent, such as a solvent that does not adversely affect the reaction (e.g., methanol, ethanol, benzene, toluene, xylene, diethyl ether, tetrahydrofuran, chloroform, dichloroethane, an optionally mixed solvent therefrom and the like), at 0° C. to 100° C. for 10 min to 24 hr to give a compound of the formula (IIBh).

Method 29: Synthetic Method of Compound of Formula (IIBj)

(IIBj)

wherein each symbol is as defined above, from among the compounds of formula (IIB) wherein Ra' is hydroxyalkyl For example, a compound of the formula (IIBc) is kept with a compound of the formula (41) in a suitable solvent, such as a solvent that does not adversely affect the reaction (e.g., benzene, toluene, xylene, diethyl ether, tetrahydrofuran, chloroform, dichloroethane, an optionally mixed solvent therefrom and the like), at 0° C. to 100° C. for 10 min to 24 hr to give a compound of the formula (IIBj).

Method 30: Synthetic Method of Compound of Formula (IIBk)

(IIBk)

wherein $R^{29}$, $R^{30}$ and $R^{31}$ are the same or different and each is hydrogen or alkyl having 1 to 3 carbon atoms and other symbols are as defined above, from among the compounds of formula (IIB) wherein Ra' is alkenyl Of the compounds of formula (IIB) wherein Ra' is hydroxyalkyl, a compound of the formula (IIBl)

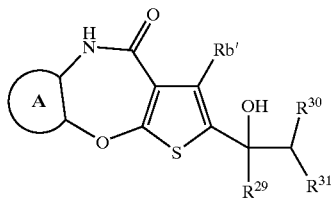

(IIBl)

wherein each symbol is as defined above, is kept in a suitable solvent, such as a solvent that does not adversely affect the reaction (e.g., methanol, ethanol, N,N-dimethylformamide, dimethyl sulfoxide, N-methylpyrolidone, hexamethylphosphorous triamide, benzene, toluene, xylene, chloroform, dichloroethane and the like, an optionally mixed solvent therefrom and the like) in the presence of an acid, such as hydrochloric acid, p-toluenesulfonic acid, methanesulfonic acid, trifluoroacetic acid and the like at room temperature to 190° C. to give a compound of the formula (IIBk).

Method 31: Synthetic Method of Compound of Formula (IIBm)

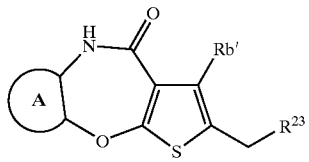

(IIBm)

wherein each symbol is as defined above, from among the compounds of formula (IIB) wherein Ra' is alkyl A compound of the formula (IIBi) is kept with triethylsilane, lithium aluminium hydride and the like in a suitable solvent, such as a solvent that does not adversely affect the reaction (e.g., trifluoroacetic acid, benzene, toluene, xylene, diethyl ether, chloroform, dichloroethane, an optionally mixed solvent therefrom and the like) at 0° C. to 100° C. for 10 min to 24 hr to give a compound of the formula (IIBm).

Method 32: Synthetic Method of Compound of Formula (IIBn)

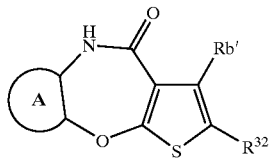

(IIBn)

wherein $R^{32}$ is alkyl having 2 to 5 carbon atoms and other symbols are as defined above, which is a compound of formula (IIB) wherein Ra' is alkyl other than methyl A compound of the formula (IIBo)

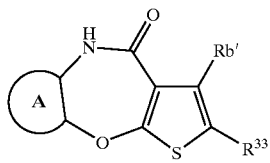

(IIBo)

wherein $R^{33}$ is alkenyl having 2 to 5 carbon atoms and other symbols are as defined above, which is a compound of the formula (IIB) wherein Ra' is alkenyl, is kept with hydrogen in a suitable solvent, such as a solvent that does not adversely affect the reaction (e.g., methanol, ethanol, ethyl acetate, dioxane, benzene, toluene, xylene, diethyl ether, chloroform, 1,2-dichloroethane, an optionally mixed solvent therefrom and the like) using palladium-activated carbon, palladium hydroxide, platinium oxide and the like as a catalyst, at 0° C. to 100° C. from normal pressure to 100 atm for 10 min to 24 hr to give a compound of the formula (IIBn).

Method 33: Synthetic Method of Compound of Formula (IIBp)

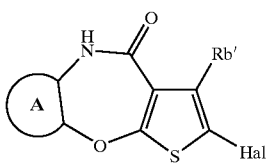

(IIBp)

wherein each symbol is as defined above, which is a compound of formula (IIB) wherein Ra' is halogen A compound of the formula (IIBb) is kept with fluorine, chlorine, bromine, iodine, iodine monochloride, N-bromosuccinimide, N-iodosuccinimide and the like in a suitable solvent, such as a solvent that does not adversely affect the reaction (e.g., acetic acid, methanol, ethanol, ethyl acetate, dioxane, benzene, toluene, xylene, diethyl ether, chloroform, 1,2-dichloroethane, an optionally mixed solvent therefrom and the like), at room temperature to 100° C. for 10 min to 24 hr to give a compound of the formula (IIBp).

Method 34: Synthetic Method of Compound of Formula (IIBq)

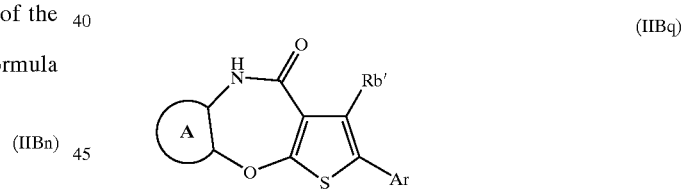

(IIBq)

wherein Ar is aryl or heteroaryl and other symbols are as defined above, which is a compound of the formula (IIB) wherein Ra' is aryl or heteroaryl A compound of the formula (IIBp) is kept with a compound of the formula (42)

Ar-Y            (42)

wherein Y is dihydroxyboryl, diethylboryl, tributylstannyl, trimethylstannyl and the like and Ar is as defined above, and tetrakistriphenylphosphine palladium and the like, in a suitable solvent, such as a solvent that does not adversely affect the reaction (e.g., methanol, ethanol, ethyl acetate, dioxane, benzene, toluene, xylene, diethyl ether, chloroform, 1,2-dichloroethane, an optionally mixed solvent therefrom and the like), at room temperature to 100° C. for 10 min to 24 hr to give a compound of the formula (IIBq).

Method 35: Synthetic Method of Compound of Formula (IIBr)

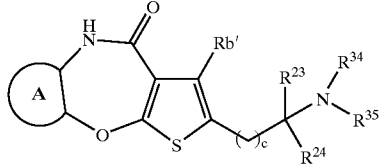
(IIBr)

wherein $R^{34}$ and $R^{35}$ are the same or different and each is hydrogen, or alkyl having 1 to 5 carbon atoms such as methyl, ethyl, propyl, butyl, pentyl and the like and other symbols are as defined above, which is a compound of the formula (IIB) wherein Ra' is aminoalkyl, monoalkylaminoalkyl or dialkylaminoalkyl Of the compounds of the formula (IIB) wherein Ra' is hydroxyalkyl, a compound of the formula (IIBs)

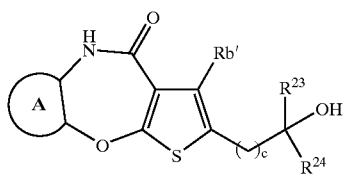
(IIBs)

wherein each symbol is as defined above is kept with a compound of the formula (43)

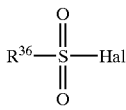
(43)

wherein $R^{36}$ is methyl, ethyl, trifluoromethyl, phenyl, 4-methylphenyl and the like and Hal is as defined above or a compound of the formula (44)

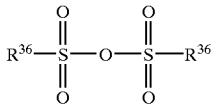
(44)

wherein $R^{36}$ is as defined above, in a suitable solvent, such as a solvent that does not adversely affect the reaction (e.g., benzene, toluene, xylene, chloroform, dichloroethane, pyridine, an optionally mixed solvent therefrom and the like), in the presence of an organic base, such as pyridine, triethylamine and the like, or an inorganic base, such as potassium carbonate, sodium carbonate, sodium hydroxide, potassium hydroxide and the like, at room temperature to 170° C. for 1 to 24 hr to give a compound of the formula (45)

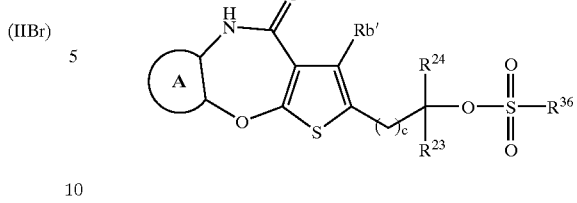
(45)

wherein each symbol is as defined above.

The obtained compound of the formula (45) is kept with a compound of the

(46)

wherein each symbol is as defined above, in a suitable solvent, such as a solvent that does not adversely affect the reaction (e.g., methanol, ethanol, dioxane, benzene, toluene, xylene, diethyl ether, chloroform, dichloroethane, an optionally mixed solvent therefrom and the like), at room temperature to 100° C. for 10 min to 24 hr to give a compound of the formula (IIBr).

Method 36: Synthetic Method of Compound of Formula (IIBe) which is a Compound of Formula (IIB) wherein Ra' is Acyloxyalkyl or Acylaminoalkyl For example, the above-mentioned compound of the formula (IIBd), which is a compound of the formula (IIB) wherein Ra' is aminoalkyl or monoalkylaminoalkyl, is kept with the above-mentioned compound of the formula (39) or (40), or ethyl formate, phenyl formate and the like, in a suitable solvent, such as a solvent that does not adversely affect the reaction (e.g., benzene, toluene, xylene, chloroform, dichloroethane, pyridine, an optionally mixed solvent therefrom and the like), at room temperature to 100° C. for 10 min to 24 hr to give a compound of the formula (IIBe).

Method 37: Synthetic Method of Compound of Formula (IIBe)

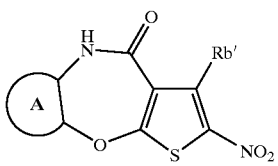
(IIBt)

wherein each symbol is as defined above, which is a compound of formula (IIB) wherein Ra' is nitro For example, a compound of the formula (IIBb) is reacted with a suitable nitrating reagent, such as concentrated nitric acid-concentrated sulfuric acid, acetyl nitrate, nitronium tetrafluoroborate and the like, at 0° C. to 100° C. for 10 min to 24 hr to give a compound of the formula (IIBt).

Method 38: Synthetic Method of Compound of Formula (IIBu)

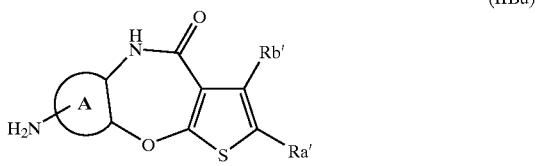

wherein each symbol is as defined above, which is a compound of formula (IIB) wherein substituent on ring A is amino A compound of the formula (IIBv) which is a compound of the formula (IIB) wherein the substituent on ring A is nitro

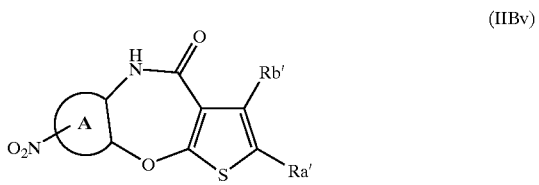

wherein each symbol is as defined above, is kept with hydrogen in a suitable solvent, such as a solvent that does not adversely affect the reaction (e.g., methanol, ethanol, ethyl acetate, dioxane, benzene, toluene, xylene, diethyl ether, chloroform, 1,2-dichloroethane, an optionally mixed solvent therefrom and the like), using palladium-activated carbon, palladium hydroxide, platinium oxide and the like as a catalyst, at 0° C. to 100° C. and normal pressure to 100 atm for 10 min to 24 hr, to give a compound of the formula (IIBu).

Method 39: Synthetic Method of Compound of Formula (IIBw)

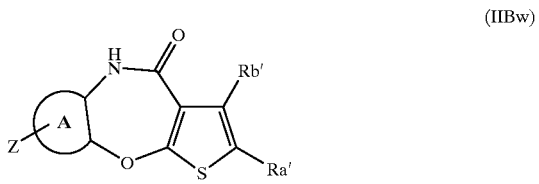

wherein Z is fluorine, chlorine, bromine, iodine or cyano and other symbols are as defined above, which is a compound of formula (IIB) wherein substituent on ring A is cyano or halogen For example, a compound of the formula (IIBu) is diazotized in a suitable solvent, such as a solvent that does not adversely affect the reaction (e.g., water, diluted hydrochloric acid, and the like) using sodium nitrite and the like at −10° C. to room temperature, and kept with fluoroboric acid, hydrogen fluoride-pyridine, sodium chloride, cuprous chloride, sodium bromide, cuprous bromide, sodium iodide, potassium iodide and the like at −10° C. to 100° C. to give a compound of the formula (IIBw).

When the compound obtained according to the above-mentioned method is to be purified as a salt of inorganic acid or organic acid, the following steps are taken. A compound of the formula (IA) or a compound of the formula (IB) is dissolved in a suitable solvent, such as methanol, ethanol, isopropyl alcohol, ethyl acetate, diethyl ether, diisopropyl ether, benzene, toluene, xylene, chloroform, methylene chloride and the like, an optionally mixed solvent therefrom and the like, and inorganic acid such as hydrochloric acid, hydrobromic acid, sulfuric acid, nitric acid, phosphoric acid and the like or organic acid such as acetic acid, propionic acid, succinic acid, glycolic acid, lactic acid, malic acid, methanesulfonic acid, benzenesulfonic acid, p-toluenesulfonic acid, camphorsulfonic acid, ascorbic acid, maleic acid, citric acid, tartaric acid, fumaric acid and the like or a hydrate thereof is added. The resulting crystals were recrystallized from a suitable solvent, such as methanol, ethanol, isopropyl alcohol, ethyl acetate, diethyl ether, dhisopropyl ether, benzene, toluene, xylene, chloroform, methylene chloride, dichloroethane and the like or a mixed solvent thereof to give a salt of an inorganic acid, organic acid, hydrate or solvate of a compound of the formula (IA) or a compound of the formula (IB).

The obtained compound of the present invention can be purified by one or more methods selected from crystallization, chromatography, extraction and filtration. When the resulting purified compound is a racemate, a desired optically active compound can be separated by, for example, preparative recrystallzation from an optically active acid, or by passing the compound through a column packed with optically active carrier. The stereoisomer can be isolated by recrystallization, column chromatography and the like.

The compound of the formula (I), particularly (IA) and (IB), of the present invention obtained in the above-mentioned manner is useful as a novel antipsychotic agent which is effective for both the positive and negative symptoms of schizophrenia, which causes less side effects of extrapyramidal motor disorder and the like and which causes less serious side effects such as agranulocytosis and the like. The present invention compound (I), particularly (IA) and (IB), is useful as a therapeutic agent for Alzheimer's disease and manic-depressive illness. The compounds of the formulas (IIA) and (IIB) are useful as important synthetic intermediates for the compounds of the formulas (IA) and (IB).

When the compound of the formula (I) is used as a pharmaceutical agent, the inventive compound is admixed with a pharmaceutically acceptable carrier (e.g., excipient, binder, disintegrator, corrective, corrigent, emulsifier), diluent, solubilizer and the like to give a pharmaceutical composition by a conventional method, which is formulated into tablet, capsule, granule, powder, syrup, suspension, solution, injection, infusion, deposit agent, suppository and the like and administered orally or parenterally.

When the tablets are used for oral administration, typically used carriers include sucrose, lactose, mannitol, maltitol, dextran, corn starch and the like, typical lubricants such as magnesium stearate, preservatives such as parabens, sorbins and the like, antioxidants such as ascorbic acid, α-tocopherol, cystein and the like, disintegrators, binders and the like. When it is administered orally as capsules, effective diluents include lactose and dry corn starch. A liquid for oral use includes syrup, suspension, solution, emulsion and the like, which may contain typical inert diluent used in this field, such as water. In addition, sweeteners or flavors may be contained.

In the case of parenteral administration such as subcutaneous injection, intravenous injection, intramuscular injection, intraperitoneal injection, infusion and the like, the pH of the active ingredient solution is adequately adjusted, bufferized and sterilized. Examples of usable vehicle or solvent include distilled water, Ringer solution, isotonic brine and the like. For intravenous use, the total concentration of solute is adjusted to make the solution isotonic.

Suppositories can be produced by admixing with a drug and a suitable nonirritative excipient such as those that are solid at normal temperature but become liquid at the temperature in the intestine and melt in rectum to release the drug, such as cocoa butter and polyethylene glycols, and the like.

The dose is determined depending on age, body weight, administration time, administration method, combination of drugs, the level of condition for which a patient is undergoing therapy, and other factors. The compound of the present invention, optical isomers thereof and pharmaceutically acceptable salts thereof are low toxic and can be used safely. While the daily dose varies depending on the conditions and body weight of patients, the kdnd of compound, administration route and the like, in the case of oral use, it is about 0.01–300 mg/person/day, preferably 0.1–100 mg/person/day, in the case of parenteral use, it is desirably about 0.01–50 mg/person/day, preferably 0.01–10 mg/person/day for subcutaneous injection, intravenous injection, intramuscular injection and intrarectal injection.

The present invention is explained in more detail in the following by way of Starting Material Synthesis Examples, Examples and Experimental Examples that do not limit the present invention in any way.

The present invention is explained in more detail in the following by way of Starting Material Synthesis Examples, Examples and Experimental Examples that do not limit the present invention in any way.

STARTING MATERIAL SYNTHESIS EXAMPLE 1

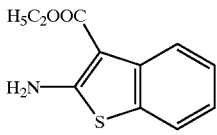

Using cyclohexanone as a starting material and following the method disclosed in a publication [Archiv der Pharmazie (Weinheim), 317, 675 (1984)], ethyl 2-aminobenzo[b]thiophene-3-carboxylate was synthesized. $^1$H-NMR (400 MHz, CDCl$_3$) δ: 8.10(d, J=7.3 Hz, 1H), 7.50(d, J=7.3 Hz, 1H), 7.31(t, J=7.3 Hz, 1H), 7.13(t, J=7.3 Hz, 1H), 6.53(br.s, 2H), 4.42(q, J=7.3 Hz, 2H), 1.46(t, J=7.3 Hz, 3H)

STARTING MATERIAL SYNTHESIS EXAMPLE 2

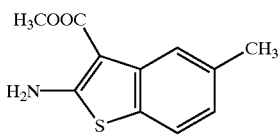

Using 3-methylcyclohexanone as a starting material and following the method disclosed in a publication [Archiv der Pharmazie (Weinheim), 317, 675 (1984)], methyl 2-amino-5-methylbenzo[b]thiophene-3-carboxylate was synthesized.

$^1$H-NMR (400 MHz, CDCl$_3$) δ: 7.89(s, 1H), 7.37(d, J=8.3 Hz, 1H), 6.97(d, J=8.3 Hz, 1H), 6.49(br.s, 2H), 3.95(s, 3H), 2.43(s, 3H)

STARTING MATERIAL SYNTHESIS EXAMPLE 3

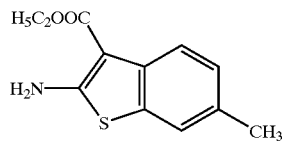

Using 4-methylcyclohexanone as a starting material and following the method disclosed in a publication [Archiv der Pharnmazie (Weinheim), 317, 675 (1984)], ethyl 2-amino-6-methylbenzo[b]thiophene-3-carboxylate was synthesized.

melting point: 126–128° C.

STARTING MATERIAL SYNTHESIS EXAMPLE 4

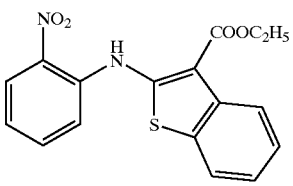

Ethyl 2-aminobenzo[b]thiophene-3-carboxylate (5 g) and 2-fluoro-nitrobenzene (2 ml) were dissolved in N,N-dimethylformamide (150 ml) and heated to 60° C. Thereto was added potassium carbonate (8 g) and the mixture was stirred at 100° C. for 18 hr. After cooling, the reaction mixture was poured into ice water, and the precipitated crystals were collected by filtration. The crystals were washed with water and diisopropyl ether and dried at 60° C. to give ethyl 2-(2-nitroanilino)-benzo[b]thiophene-3-carboxylate (5.7 g).

$^1$H-NMR (400 MHz, CDCl$_3$) δ: 12.2(s, 1H), 8.32(d, J=8.3 Hz, 1H), 8.25(d, J=8.3 Hz, 1H), 8.10(d, J=8.8 Hz, 1H), 7.67–7.62(m, 2H), 7.42(t, J=7.8 Hz, 1H), 7.27(m, 1H), 7.16(t, J=7.8 Hz, 1H), 4.57(q, J=7.3 Hz, 2H), 1.52(t, J=7.3 Hz, 3H)

STARTING MATERIAL SYNTHESIS EXAMPLE 5

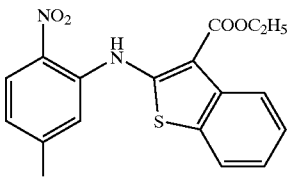

Ethyl 2-aminobenzo[b]thiophene-3-carboxylate (69.3 g) and 2,4-difluoronitrobenzene (50 g) were dissolved in dimethyl sulfoxide (550 Ml) and heated to 50° C. Thereto was added potassium carbonate (63 g) and the mixture was stirred at 100° C. for 70 min. After cooling, the reaction mixture was allowed to cool to 70° C. and poured into water (2.5 L). The reaction mixture was allowed to stand still, and filtered. The filtrated orange crystals were washed with ethyl acetate to give ethyl 2-(5-fluoro-2-nitroanilino)benzo[b]thiophene-3-carboxylate (50.7 g).

melting point 137–140° C.

$^1$H-NMR (400 MHz, CDCl$_3$) δ: 12.40(br.s, 1H), 8.33–8.29(m, 2H), 7.79(dd, J=7.8, 2.9 Hz, 1H), 7.65(d, J=8.3 Hz, 1H), 7.42(dd, J=8.3, 8.2 Hz, 1H), 7.29(dd, J=6.9, 8.3 Hz, 1H), 6.80–6.77(m, 1H), 4.54(q, J=6.8 Hz, 2H), 1.49(t, J=6.8 Hz, 3H).

IR (KBr): 3085, 2993, 1624, 1582, 1553, 1510, 1274, 1206, 1035 cm$^{-1}$. MS: m/e 360.

STARTING MATERIAL SYNTHESIS EXAMPLE 6

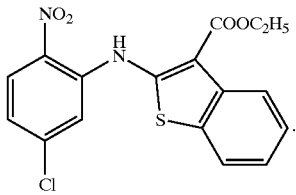

In the same manner as in Starting Material Synthesis Example 4 and using ethyl 2-aminobenzo[b]thiophene-3-carboxylate (4.0 g), 2,4-dichloronitrobenzene (3.8 g) and dimethyl sulfoxide (55 ml), ethyl 2-(5-chloro-2-nitroanilino)benzo[b]thiophene-3-carboxylate (3.2 g) was obtained.

$^1$H-NMR(400 MHz, CDCl$_3$) δ: 12.27(br.s, 1H), 8.31(d, J=8.3 Hz, 1H), 8.19(d, J=8.8 Hz 1H), 8.08(s, 1H), 7.65(d, J=7.3 Hz, 1H), 7.41(dd, J=7.3, 8.3 Hz, 1H), 7.28(dd, j=7.8, 7.3 Hz, 1H), 7.06(d, 8.3 Hz, 1H), 4.54(q, J=7.3 Hz, 2H), 1.49(t, J=7.3 Hz, 3H)

STARTING MATERIAL SYNTHESIS EXAMPLE 7

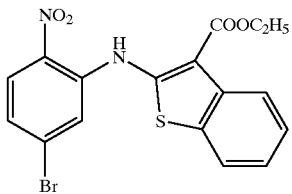

In the same manner as in Starting Material Synthesis Example 4 and using ethyl 2-aminobenzo[b]thiophene-3-carboxylate, 2,4-dibromonitrobenzene and dimethyl sulfoxide, ethyl 2-(5-bromo-2-nitroanilino)benzo[b]thiophene-3-carboxylate is obtained.

STARTING MATERIAL SYNTHESIS EXAMPLE 8

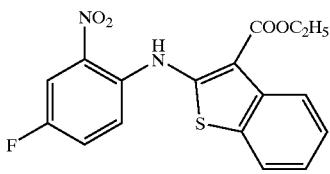

In the same manner as in Starting Material Synthesis Example 4 and using ethyl 2-aminobenzo[b]thiophene-3-carboxylate, 2,5-difluoronitrobenzene and dimethyl sulfoxide, ethyl 2-(4-fluoro-2-nitroanilino)benzo[b]thiophene-3-carboxylate is obtained.

STARTING MATERIAL SYNTHESIS EXAMPLE 9

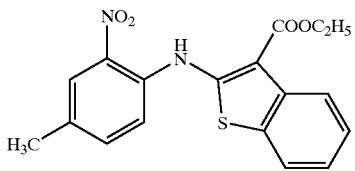

In the same manner as in Starting Material Synthesis Example 4 and using ethyl 2-aminobenzo[b]thiophene-3-carboxylate (4.0 g), 4-fluoro-3-nitrotoluene (3.3 g) and dimethyl sufoxide (55 ml), ethyl 2-( 4-methyl-2-nitroanilino)benzo[b]thiophene-3-carboxylate (6.5 g) was obtained.

$^1$H-NMR (400 MHz, CDCl$_3$) δ: 12.06(br.s, 1H), 8.27(d, J=8.3 Hz, 1H), 8.01(s, 1H), 7.95(d, J=8.8 Hz, 1H), 7.58(d, J=7.3 Hz, 1H), 7.44(d, J=8.3 Hz, 1H), 7.38(dd, J=8.8, 8.3 Hz, 1H), 7.21(d, J=7.3 Hz, 1H), 4.53(q, J=7.3 Hz, 2H), 2.40(s, 3H), 1.49(t, J=7.3 Hz, 3H)

STARTING MATERIAL SYNTHESIS EXAMPLE 10

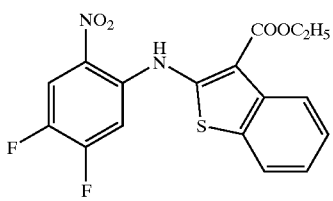

In the same manner as in Starting Material Synthesis Example 4 and using ethyl 2-aminobenzo[b]thiophene-3-carboxylate, 2,4,5-trifluoronitrobenzene and dimethyl sulfoxide, ethyl 2-(4,5-difluoro-2-nitroanilino)benzo[b]thiophene-3-carboxylate is obtained.

STARTING MATERIAL SYNTHESIS EXAMPLE 11

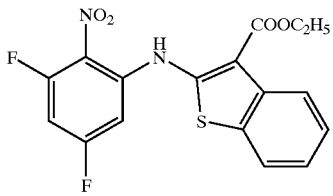

In the same manner as in Starting Material Synthesis Example 4 and using ethyl 2-aminobenzo[b]thiophene-3-carboxylate, 2,4,6-trifluoronitrobenzene and dimethyl sulfoxide, ethyl 2-(3,5-difluoro-2-nitroanilino)benzo[b]thiophene-3-carboxylate is obtained.

STARTING MATERIAL SYNTHESIS EXAMPLE 12

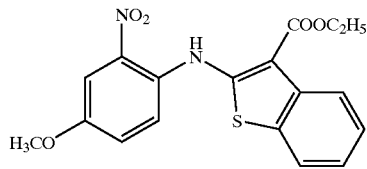

In the same manner as in Starting Material Synthesis Example 4 and using ethyl 2-aminobenzo[b]thiophene-3-carboxylate, 2-fluoro-5-methoxynitrobenzene and dimethyl sulfoxide, ethyl 2-(4-methoxy-2-nitroanilino)benzo[b]thiophene-3-carboxylate is obtained.

STARTING MATERIAL SYNTHESIS EXAMPLE 13

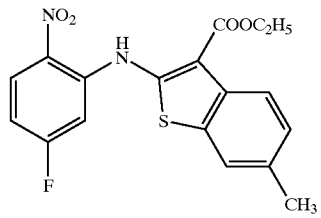

In the same manner as in Starting Material Synthesis Example 4 and using ethyl 2-amino-6-methylbenzo[b]thiophene-3-carboxylate (4.5 g), 2,4-difluoronitrobenzene (3.1 g) and dimethyl sulfoxide, ethyl 2-(5-fluoro-2-nitroanilino)-6-methylbenzo[b]thiophene-3-carboxylate (5.1 g) was obtained.

melting point: 147–149° C.

STARTING MATERIAL SYNTHESIS EXAMPLE 14

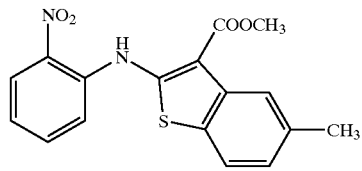

In the same manner as in Starting Material Synthesis Example 4 and using methyl 2-amino-5-methylbenzo[b]thiophene-3-carboxylate, 2-fluoronitrobenzene and dimethyl sulfoxide, methyl 2-(2-nitroanilino)-5-methylbenzo[b]thiophene-3-carboxylate was obtained.

STARTING MATERIAL SYNTHESIS EXAMPLE 15

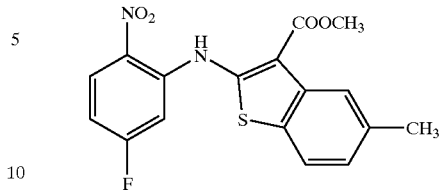

In the same manner as in Starting Material Synthesis Example 4 and using methyl 2-amino-5-methylbenzo[b]thiophene-3-carboxylate (3.11 g), 2,4-difluoronitrobenzene (1.54 ml) and dimethyl sulfoxide (30 ml), methyl 2-(5-fluoro-2-nitroanilino)-5-methylbenzo[b]thiophene-3-carboxylate was obtained.

$^1$H-NMR (400 MHz, CDCl$_3$) δ: 12.44(br.s, 1H), 8.34(dd, J=9.3, 3.4 Hz, 1H), 8.14(s, 1H), 7.82(d, J=8.3 Hz, 1H), 7.55(d, J=7.8 Hz, 1H), 7.14(d, J=8.3 Hz, 1H), 6.83–6.78(m, 1H), 4.09(s, 3H), 2.49(s, 3H)

STARTING MATERIAL SYNTHESIS EXAMPLE 16

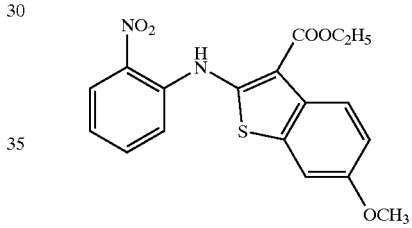

In the same manner as in Starting Material Synthesis Example 4 and using ethyl 2-amino-6-methoxybenzo[b]thiophene-3-carboxylate, 2-fluoronitrobenzene and dimethyl sulfoxide, ethyl 2-6-methoxy-(2-nitroanilino)benzo[b]thiophene-3-carboxylate is obtained.

STARTING MATERIAL SYNTHESIS EXAMPLE 17

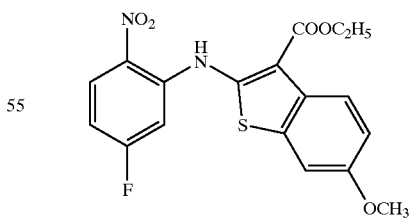

In the same manner as in Starting Material Synthesis Example 4 and using ethyl 2-amino-6-methoxybenzo[b]thiophene-3-carboxylate, 2,4-difluoronitrobenzene and dimethyl sulfoxide, ethyl 2-(5-fluoro-2-nitroanilino)-6-methoxybenzo[b]thiophene-3-carboxylate is obtained.

STARTING MATERIAL SYNTHESIS EXAMPLE 18

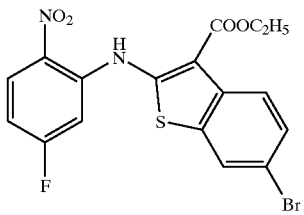

In the same manner as in Starting Material Synthesis Example 4 and using ethyl 6-bromo-2-arminobenzo[b]thiophene-3-carboxylate (8.8 g), 2,4-difluoronitrobenzene (5.6 g) and dimethyl sulfoxide (100 ml), ethyl 6-bromo-2-(5-fluoro-2-nitroanilino)benzo[b]thiophene-3-carboxylate (10 g) was obtained.

$^1$H-NMR (400 MHz, CDCl$_3$) δ: 12.35(s, 1H), 8.31(dd, 1H), 8.17(d, J=8.8 Hz, 1H), 7.76–7.71(m, 2H), 7.50(d, J=8.8 Hz, 1H), 6.82(dd, 1H), 4.53(q, J=7.3 Hz, 2H), 1.48(t, J=7.3 Hz, 3H)

STARTING MATERIAL SYNTHESIS EXAMPLE 19

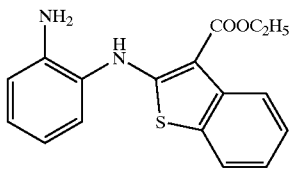

Ethyl 2-(2-nitroanilino)benzo[b]thiophene-3-carboxylate (4.9 g) was dissolved in ethyl acetate (200 ml) and 10% palladium-carbon (0.5 g) was added. The mixture was stirred with hydrogen (60 kg/cm$^2$) at 60° C. for 5 hr. The reaction mixture was cooled and the catalyst was filtered off. The filtrate was evaporated under reduced pressure to give ethyl 2-(2-aminoanilino)benzo[b]thiophene-3-carboxylate (3.5 g).

$^1$H-NMR (400 MHz, CDCl$_3$) δ: 9.61(s, 1H), 8.14(d, J=7.8 Hz, 1H), 7.47(d, J=7.8 Hz, 1H), 7.33–7.35(m, 2H), 7.10–7.12(m, 2H), 6.80–6.86(m, 2H), 4.47(q, J=7.3 Hz, 2H) 3.88(br.s, 2H), 1.50(t, J=7.3 Hz, 3H)

STARTING MATERIAL SYNTHESIS EXAMPLE 20

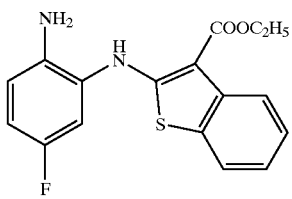

Ethyl 2-(5-fluoro-2-nitroanilino)benzo[b]thiophene-3-carboxylate (50.7 g) was dissolved in ethyl acetate (1000 ml) and 10% palladium-carbon (8.0 g) was added. The mixture was stirred with hydrogen (60 kg/cm$^2$) at 55° C. for 5 hr. The reaction mixture was cooled and the catalyst was filtered off. The filtrate was evaporated under reduced pressure and the residue was purified by silica gel column chromatography (chloroform) to give ethyl 2-(2-amino-5-fluoroanilino)benzo[b]thiophene-3-carboxylate (24.5 g).

melting point 141–142° C.

$^1$H-NMR (400 MHz, CDCl$_3$) δ: 9.87(s, 1H), 8.14(d, J=8.8 Hz, 1H), 7.50(d, J=7.3 Hz, 1H), 7.31–7.35(m, 1H), 7.19–7.11(m, 2H), 6.75–6.85(m, 2H), 3.69(br.s, 2H), 4.45(q, J=7.3 Hz, 2H), 1.48(t, J=7.3 Hz, 3H). IR (KBr): 3417, 3353, 3234, 2994, 1633, 1605, 1551, 1479, 1384, 1235, 1039 cm$^{-1}$. MS: m/e 330

STARTING MATERIAL SYNTHESIS EXAMPLE 21

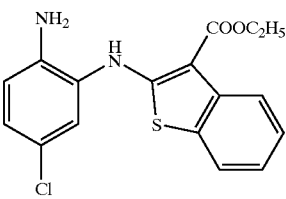

Ethyl 2-(5-chloro-2-nitroanilino)benzo[b]thiophene-3-carboxylate (3.2 g) was suspended in ethanol (40 ml) and a solution obtained by dissolving tin(II) chloride dihydrate (7.7 g) in ethanol (50 ml) and 18% hydrochloric acid (50 ml) was added with stirring the mixture. The mixture was stirred at 60° C. for 2 hr and cooled to 30° C. Potassium carbonate was added until the reaction mixture was basified. After filtering through celite, the filtrate was extracted with ethyl acetate, washed with water and dried over magnesium sulfate. After natural filtration, the solvent was evaporated under reduced pressure to give ethyl 2-(2-amino-5-chloroanilino)benzo[b]thiophene-3-carboxylate (2.6 g).

$^1$H-NMR (400 MHz, CDCl$_3$) δ: 9.71(s, 1H), 8.14(d, J=8.3 Hz, 1H), 7.51(d, J=7.3 Hz, 1H), 7.38(s, 1H), 7.36(t, J=7.3 Hz, 1H), 7.15(dd, J=7.8, 7.3 Hz, 1H), 7.09(d, J=7.8 Hz, 1H), 6.77(d, J=8.3 Hz, 1H), 4.47(q, J=7.3 Hz, 2H), 3.88(br.s, 2H), 1.50(t, J=7.3 Hz, 3H)

STARTING MATERIAL SYNTHESIS EXAMPLE 22

In the same manner as in Starting Material Synthesis Example 19 and using ethyl 2-(5-chloro-2-nitroanilino)benzo[b]thiophene-3-carboxylate, ethyl acetate, 10% palladium-carbon and hydrogen (60 atm kg/cm$^2$), ethyl 2-(2-amino-5-chloroanilino)benzo[b]thiophene-3-carboxylate is obtained.

STARTING MATERIAL SYNTHESIS EXAMPLE 23

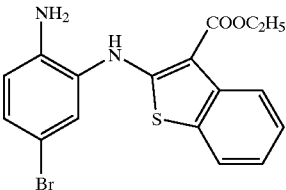

In the same manner as in Starting Material Synthesis Example 19 and using ethyl 2-(5-bromo-2-nitroanilino)benzo[b]thiophene-3-carboxylate, ethyl acetate, 10% palladium-carbon and hydrogen (60 atm kg/cm$^2$), ethyl 2-(2-amino-5-bromoanilino)benzo[b]thiophene-3-carboxylate is obtained.

STARTING MATERIAL SYNTHESIS EXAMPLE 24

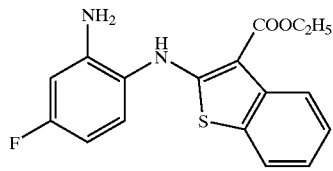

In the same manner as in Starting Material Synthesis Example 19 and using ethyl 2-(4-fluoro-2-nitroanilino)benzo[b]thiophene-3-carboxylate, ethyl acetate, 10% palladium-carbon and hydrogen (60 atm kg/cm$^2$), ethyl 2-(2-amino-4-fluoroanilino)benzo[b]thiophene-3-carboxylate is obtained.

STARTING MATERIAL SYNTHESIS EXAMPLE 25

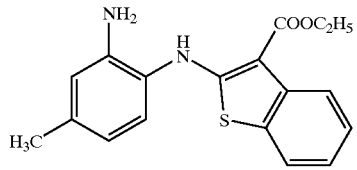

In the same manner as in Starting Material Synthesis Example 19 and using ethyl 2-(4-methyl-2-nitroanilino)benzo[b]thiophene-3-carboxylate (6.5 g), ethyl acetate (140 ml), 10% palladium-carbon and hydrogen (500 mg, 60 atm kg/cm$^2$), ethyl 2-(2-amino-4-methylanilino)benzo[b]thiophene-3-carboxylate (3.7 g) was obtained.

$^1$H-NMR (400 MHz, CDCl$_3$) δ: 9.46(br.s, 1H), 8.12(d, J=8.3 Hz, 1H), 7.45(d, J=7.3 Hz, 1H), 7.33(dd, J=7.3, 7, 8 Hz, 1H), 7.18(d, J=8.3 Hz, 1H), 7.10(dd, J=7.8, 8.3 Hz, 1H), 6.67(s, 1H), 6.63(d, J=7.8 Hz, 1H), 4.46(q, J=7.3 Hz, 2H), 3.83(br.s, 2H), 1.56(s, 3H), 1.26(t, J=7.3 Hz, 3H)

STARTING MATERIAL SYNTHESIS EXAMPLE 26

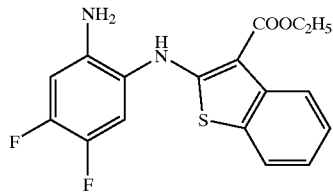

In the same manner as in Starting Material Synthesis Example 19 and using ethyl 2-(4,5-difluoro-2-nitroanilino)benzo[b]thiophene-3-carboxylate, ethyl acetate, 10% palladium-carbon and hydrogen (60 atm kg/cm$^2$), ethyl 2-(2-amino-4,5-difluoroanilino)benzo[b]thiophene-3-carboxylate is obtained.

STARTING MATERIAL SYNTHESIS EXAMPLE 27

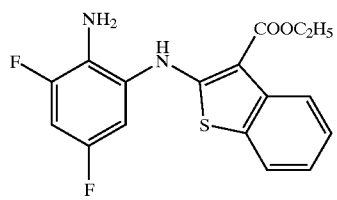

In the same manner as in Starting Material Synthesis Example 19 and using ethyl 2-(3,5-difluoro-2-nitroanilino)benzo[b]thiophene-3-carboxylate, ethyl acetate, 10% palladium-carbon and hydrogen (60 atm kg/cm$^2$), ethyl 2-(2-amino-3,5-difluoroanilino)benzo[b]thiophene-3-carboxylate is obtained.

STARTING MATERIAL SYNTHESIS EXAMPLE 28

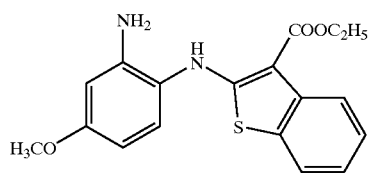

In the same manner as in Starting Material Synthesis Example 19 and using ethyl 2-(4-methoxy-2-nitroanilino)benzo[b]thiophene-3-carboxylate, ethyl acetate, 10% palladium-carbon and hydrogen (60 atm kg/cm$^2$), ethyl 2-(2-amino-4-methoxyanilino)benzo[b]thiophene-3-carboxylate is obtained.

STARTING MATERIAL SYNTHESIS EXAMPLE 29

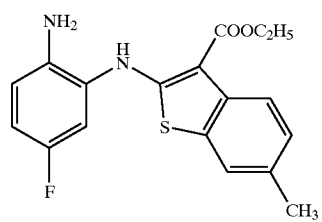

In the same manner as in Starting Material Synthesis Example 19 and using ethyl 2-(5-fluoro-2-nitroanilino)-6-methylbenzo[b]thiophene-3-carboxylate (1.9 g), ethyl acetate (200 ml), 10% palladium-carbon (0.4 g) and hydrogen (60 atm kg/cm$^2$), ethyl 2-(2-amino-5-fluoroanilino)-6-methylbenzo[b]thiophene-3-carboxylate (1.54 g) was obtained.

melting point: 174–175° C.

STARTING MATERIAL SYNTHESIS EXAMPLE 30

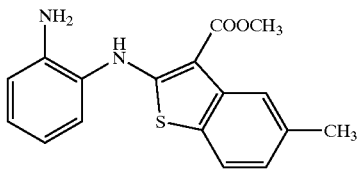

In the same manner as in Starting Material Synthesis Example 19 and using methyl 2-(2-nitroanilino)-5-methylbenzo[b]thiophene-3-carboxylate, ethyl acetate, 10%/opalladium-carbon and hydrogen (60 atm kg/cm$^2$), methyl 2-(2-aminoanilino)-5-methylbenzo[b]thiophene-3-carboxylate is obtained.

STARTING MATERIAL SYNTHESIS EXAMPLE 31

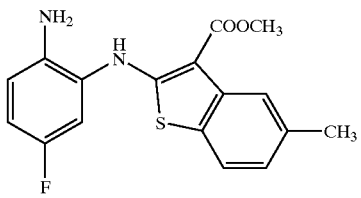

In the same manner as in Starting Material Synthesis Example 19 and using methyl 2-(5-fluoro-2-nitroanilino)-5-methylbenzo[b]thiophene-3-carboxylate (4.42 g), ethyl acetate (400 ml), 10% palladium-carbon and hydrogen (400 mg, 60 atm kg/cm$^2$), methyl 2-(2-amino-5-fluoroanilino)-5-methylbenzo[b]thiophene-3-carboxylate (1.82 g) was obtained.

$^1$H-NMR (400 MHz, CDCl$_3$) δ: 9.84(s, 1H), 7.94(s, 1H), 7.40(d, J=7.8 Hz, 1H), 7.19(d, J=9.3 Hz, 1H), 6.98(d, J=8.3 Hz, 1H), 6.86–6.77(m, 2H), 4.01(s, 3H), 3.69(br.s, 2H), 2.45(s, 3H)

STARTING MATERIAL SYNTHESIS EXAMPLE 32

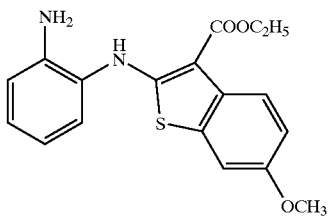

In the same manner as in Starting Material Synthesis Example 19 and using ethyl 2-6-methoxy-(2-nitroanilino)benzo[b]thiophene-3-carboxylate, ethyl acetate, 10% palladium-carbon and hydrogen (60 atm kg/cm$^2$), ethyl 2-(2-aminoanilino)-6-methoxybenzo[b]thiophene-3-carboxylate is obtained.

STARTING MATERIAL SYNTHESIS EXAMPLE 33

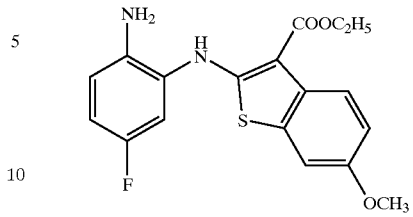

In the same manner as in Starting Material Synthesis Example 19 and using ethyl 2-(5-fluoro-2-nitroanilino)-6-methoxybenzo[b]thiophene-3-carboxylate, ethyl acetate, 10% palladium-carbon and hydrogen (60 atm kg/cm$^2$), ethyl 2-(2-amino-5-fluoroanilino)-6-methoxybenzo[b]thiophene-3-carboxylate is obtained.

STARTING MATERIAL SYNTHESIS EXAMPLE 34

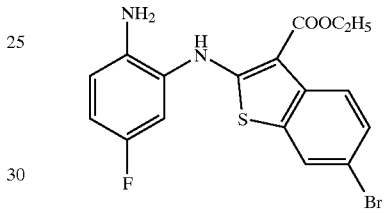

In the same manner as in Starting Material Synthesis Example 21 and using ethyl 6-bromo-2-(5-fluoro-2-nitroanilino)benzo[b]thiophene-3-carboxylate (10 g), ethanol (80 ml), 18% hydrochloric acid (80 ml) and tin(II) chloride dihydrate (20.6 g), ethyl 6-bromo-2-(2-amino-5-fluoroanilino)benzo[b]thiophene-3-carboxylate (3.8 g) was obtained.

$^1$H-NMR(400 MHz, CDCl$_3$) δ: 9.81(s, 1H), 7.98(d, J=8.8 Hz, 1H), 7.60(s, 1H), 7.41(d, J=8.8 Hz, 1H), 7.13(d, J=9.3 Hz, 1H), 6.84–6.76(m, 2H), 4.44(q, J=7.3Hz, 2H), 3.75(br.s, 2H), 1.47(t, J=7.3 Hz, 3H)

STARTING MATERIAL SYNTHESIS EXAMPLE 35

In addition, in the same manner as in Starting Material Synthesis Example 19 and using ethyl 6-bromo-2-(5-fluoro-2-nitroanilino)benzo[b]thiophene-3-carboxylate, ethyl acetate, 10% palladium-carbon and hydrogen (60 atm kg/cm$^2$), ethyl 6-bromo-2-(2-amino-5-fluoroanilino)benzo[b]thiophene-3-carboxylate is obtained.

STARTING MATERIAL SYNTHESIS EXAMPLE 36

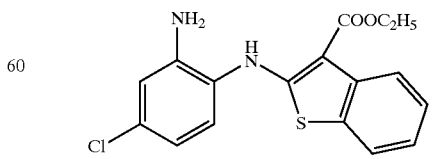

In the same manner as in Starting Material Synthesis Example 4 and using ethyl 2-aminobenzo[b]thiophene-3- carboxylate (6.0 g), 2,5-dichloronitrobenzene (5.8 g) and dimethyl sulfoxide (70 ml), crude crystals (9.5 g) of ethyl 2-(4-chloro-2-nitroanilino)benzo[b]thiophene-3-carboxylate were obtained. Without purification, in the same manner as in Starting Material Synthesis Example 21 and using ethanol (100 ml), 18% hydrochloric acid (100 ml) and tin(II) chloride dihydrate (22.5 g), ethyl 2-(2-amino-4-chloroanilino)benzo[b]thiophene-3-carboxylate (3.0 g) was obtained.

$^1$H-NMR (400 MHz, CDCl$_3$) δ: 9.51(s, 1H), 8.11(d, J=8.3 Hz, 1H), 7.46(d, J=7.8 Hz, 1H), 7.29(dd, J=7.3, 8.3 Hz, 1H), 7.23(d, J=8.3 Hz, 1H), 7.11(dd, J=7.3, 3.8 Hz, 1H), 6.81(s, 1H), 6.75(d, J=8.3 Hz, 1H), 4.45(q, J=7.3 Hz, 2H), 3.95(br.s, 2H), 1.48(t, J=7.3 Hz, 3H)

STARTING MATERIAL SYNTHESIS EXAMPLE 37

In the same manner as in Starting Material Synthesis Example 19 and using ethyl 2-(4-chloro-2-nitroanilino)benzo[b]thiophene-3-carboxylate, ethyl acetate, 10% palladium-carbon and hydrogen (60 atm kg/cm$^2$), ethyl 2-(2-amino-4-chloroanilino)benzo[b]thiophene-3-carboxylate is obtained.

STARTING MATERIAL SYNTHESIS EXAMPLE 38

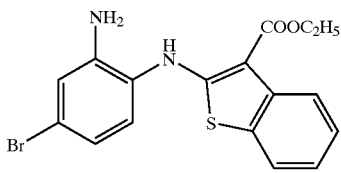

In the same manner as in Starting Material Synthesis Example 4 and using ethyl 2-aminobenzo[b]thiophene-3-carboxylate (6.0 g), 2,5-dibromonitrobenzene (8.5 g) and dimethyl sufoxide (70 ml), crude crystals (7.3 g) of ethyl 2-(4-bromo-2-nitroanilino)benzo[b]thiophene-3-carboxylate were obtained. Without purification, in the same manner as in Starting Material Synthesis Example 21 and using ethanol (70 ml), 18% hydrochloric acid (70 ml) and tin(II) chloride-dihydrate (15.7 g), ethyl 2-(2-amino-4-bromoanilino)benzo[b]thiophene-3-carboxylate (3.3 g) was obtained.

$^1$H-NMR (400 MHz, CDCl$_3$) δ: 9.52(s, 1H), 8.11(d, 1H), 7.46(d, J=8.3 Hz, 1H), 7.31(dd, 1H), 7.18(d, J=8.3 Hz, 1H), 7.11(dd, 1H), 6.99(s, 1H), 6.90(d, 1H), 4.44(q, J=7.3 Hz, 2H), 3.94(br.s, 2H), 1.48(t, J=7.3 Hz, 3H)

STARTING MATERIAL SYNTHESIS EXAMPLE 39

In the same manner as in Starting Material Synthesis Example 19 and using ethyl 2-(4-bromo-2-nitroanilino)benzo[b]thiophene-3-carboxylate, ethyl acetate, 10% palladium-carbon and hydrogen (60 atm kg/cm$^2$), ethyl 2-(2-amino-4-bromoanilino)benzo[b]thiophene-3-carboxylate is obtained.

STARTING MATERIAL SYNTHESIS EXAMPLE 40

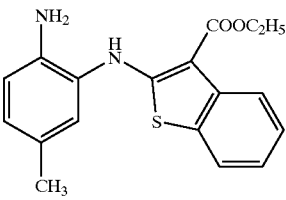

In the same manner as in Starting Material Synthesis Example 4 and using ethyl 2-aminobenzo[b]thiophene-3-carboxylate (3 g), 3-fluoro-4-nitrotoluene (2.1 g) and dimethyl sulfoxide (25 ml), ethyl 2-(5-methyl-2-nitroanilino)benzo[b]thiophene-3-carboxylate (5.4 g) was obtained. Without purification, in the same manner as in Starting Material Synthesis Example 19 and using 10% palladium-carbon (1.5 g), ethyl 2-(2-amino-5-methylanilino)benzo[b]thiophene-3-carboxylate (1.6 g) was obtained.

$^1$H-NMR(400 MHz, CDCl$_3$) δ: 9.61(s, 1H), 8.14(d, J=7.8 Hz, 1H), 7.47(d, J=7.8 Hz, 1H), 7.32(dd, J=7.8, 7.8 Hz, 1H), 7.13(s, 1H), 7.10(dd, J=7.8, 7.8 Hz, 1H), 6.95(d, J=7.8 Hz, 1H), 6.76(d, J=7.8 Hz, 1H), 4.46(q, J=7.3 Hz, 2H), 3.73(br.s, 2H), 2.28(s, 3H), 1.50(t, J=7.3 Hz, 3H)

STARTING MATERIAL SYNTHESIS EXAMPLE 41

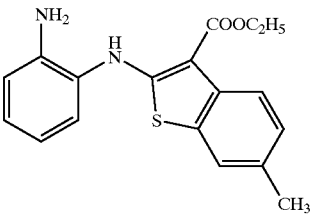

In the same manner as in Starting Material Synthesis Example 4 and using ethyl 2-amino-6-methylbenzo[b]thiophene-3-carboxylate (4.18 g), 2-fluoronitrobenzene (2.5 g) and dimethyl sulfoxide (50 ml), crude crystals (7.5 g) of ethyl 6-methyl-2-(2-nitroanilino)benzo[b]thiophene-3-carboxylate were obtained. Without purification, in the same manner as in Starting Material Synthesis Example 21 and using ethanol (50 ml), 18% hydrochloric acid (70 ml) and tin(II) chloride-dihydrate (16 g), ethyl 2-(2-aminoanilino)-6-methylbenzo[b]thiophene-3-carboxylate (3.7 g) was obtained.

$^1$H-NMR(400 MHz, CDCl$_3$) δ: 9.53(br.s, 1H), 7.99(d, J=8.3 Hz, 1H), 7.32(d, J=7.8 Hz, 1H), 7.25(s, 1H), 7.13(m, 2H), 6.83–6.80(m, 2H), 4.44(q, J=7.3 Hz, 2H), 3.86(br.s, 2H), 2.37(s, 3H), 1.47(t, J=7.3Hz, 3H)

STARTING MATERIAL SYNTHESIS EXAMPLE 42

In the same manner as in Starting Material Synthesis Example 19 and using ethyl 6-methyl-2-(2-nitroanilino)benzo[b]thiophene-3-carboxylate, ethyl acetate, 10% palladium-carbon and hydrogen (60 atm kg/cm$^2$), ethyl 2-(2-aminoanilino)-6-methylbenzo[b]thiophene-3-carboxylate is obtained.

STARTING MATERIAL SYNTHESIS EXAMPLE 43

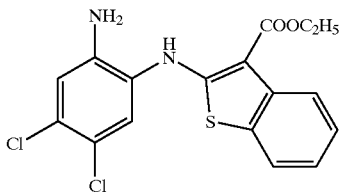

In the same manner as in Starting Material Synthesis Example 4 and using ethyl 2-aminobenzo[b]thiophene-3-carboxylate (6.0 g), 2,4,5-trichloronitrobenzene (6.8 g) and dimethyl sulfoxide (70 ml), crude crystals (10.3 g) of ethyl 2-(4,5-dichloro-2-nitroanilino)benzo[b]thiophene-3-carboxylate were obtained. Without purification, in the same manner as in Starting Material Synthesis Example 21 and using ethanol (100 ml), 18%hydrochloric acid (100 ml) and tin(II) chloride-dihydrate (22.8 g), ethyl 2-(2-amino-4,5-dichloroanilino)benzo[b]thiophene-3-carboxylate (5.3 g) was obtained.

$^1$H-NMR(400 MHz, CDCl$_3$) δ: 9.33(s, 1H), 8.15(d, J=7.3 Hz, 1H), 7.44(d, J=7.8 Hz, 1H), 7.32(dd, J=7.8, 7.3 Hz, 1H), 7.25(d, J=8.8 Hz, 1H), 7.12(dd, J=7.8, 7.3 Hz, 1H), 6.69(d, J=8.8 Hz, 1H), 4.47(q, J=7.3 Hz, 2H), 4.10(br.s, 2H), 1.49(t, J=7.3 Hz, 3H)

STARTING MATERIAL SYNTHESIS EXAMPLE 44

In the same manner as in Starting Material Synthesis Example 19 and using ethyl 2-(4,5-dichloro-2-nitroanilino)benzo[b]thiophene-3-carboxylate, ethyl acetate, 10% palladium-carbon and hydrogen (60 atm kg/cm$^2$), ethyl 2-(2-amino-4,5-dichloroanilino)benzo[b]thiophene-3-carboxylate is obtained.

STARTING MATERIAL SYNTHESIS EXAMPLE 45

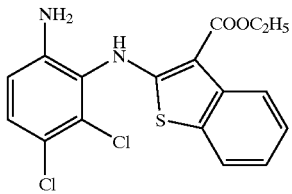

In the same manner as in Starting Material Synthesis Example 4 and using ethyl 2-aminobenzo[b]thiophene-3-carboxylate (6.6 g), 2,3,4-trichloronitrobenzene (7.0 g) and dimethyl sulfoxide (70 ml), crude crystals (12 g) of ethyl 2-(2,3-dichloro-6-nitroanilino)benzo[b]thiophene-3-carboxylate were obtained. Without purification, in the same manner as in Starting Material Synthesis Example 21 and using ethanol (40 ml), 18% hydrochloric acid (60 ml) and tin(II) chloride-dihydrate (24.6 g), ethyl 2-(6-amino-2,3-dichloroanilino)benzo[b]thiophene-3-carboxylate (4.2 g) was obtained.

STARTING MATERIAL SYNTHESIS EXAMPLE 46

In the same manner as in Starting Material Synthesis Example 19 and using ethyl 2-(2,3-dichloro-6-nitroanilino)benzo[b]thiophene-3-carboxylate, ethyl acetate, 10% palladium-carbon and hydrogen (60 atm kg/cm$^2$), ethyl 2-(6-amino-2,3-dichloroanilino)benzo[b]thiophene-3-carboxylate is obtained.

STARTING MATERIAL SYNTHESIS EXAMPLE 47

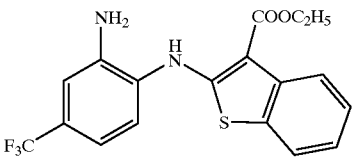

In the same manner as in Starting Material Synthesis Example 4 and using ethyl 2-aminobenzo[b]thiophene-3-carboxylate (5.0 g), 4-fluoro-3-nitrobenzotrifluoride (5.1 g) and dimethyl sulfoxide (65 ml), ethyl 2-(2-nitro-4-trifluoromethylanilino)benzo[b]thiophene-3-carboxylate (12 g) was obtained. Without purification, in the same manner as in Starting Material Synthesis Example 21 and using ethanol (50 ml), 18% hydrochloric acid (50 ml) and tin(II) chloride-dihydrate (10.9 g), ethyl 2-(2-amino-4-trifluoromethylanilino)benzo[b]thiophene-3-carboxylate (2.8 g) was obtained.

$^1$H-NMR(400 MHz, CDCl$_3$) δ: 9.93(br.s, 1H), 8.16(d, J=8.3 Hz, 1H), 7.52(m, 2H), 7.36(dd, J=7.3, 8.3 Hz, 1H), 7.17(dd, J=7.3, 6.9 Hz, 1H), 7.08(m, 2H), 4.48(q, J=7.3 Hz, 2H), 4.08(br.s, 2H), 1.51(t, J=7.3 Hz, 3H)

STARTING MATERIAL SYNTHESIS EXAMPLE 48

In the same manner as in Starting Material Synthesis Example 19 and using ethyl 2-(2-amino-4-trifluoromethylanilino)benzo[b]thiophene-3-carboxylate, ethyl acetate, 10% palladium-carbon and hydrogen (60 atm kg/cm$^2$), ethyl 2-(2-amino-4-trifluoromethylanilino)benzo[b]thiophene-3-carboxylate is obtained.

STARTING MATERIAL SYNTHESIS EXAMPLE 49

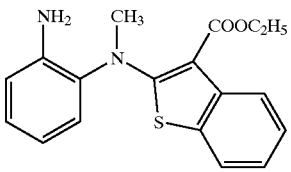

Ethyl 2-(2-nitroanilino)benzo[b]thiophene-3-carboxylate (6.0 g) was dissolved in N,N-dimethylformamide (120 ml) and the mixture was stirred at 0° C., during which potassium tert-butoxide (3.0 g) was added portionwise. Methyl iodide (12.4 g) was added dropwise under ice-cooling and the mixture was stirred at 0° C. for 5 min and heated to room temperature. The reaction mixture was extracted with ethyl acetate, washed with saturated brine and dried over anhydrous magnesium sulfate. After natural filtration, the solvent was evaporated under reduced pressure, and the residue was separated by silica gel column chromatography (hexane:ethyl acetate=4:1) to give crude crystals (2.8 g) of ethyl 2-(N-methyl-2-nitroanilino)benzo[b]thiophene-3-carboxylate. Without purification, the crystals were treated in the same manner as in Starting Material Synthesis Example 21 using ethanol (50 ml), 18% hydrochloric acid (50 ml) and tin(II) chloride-dihydrate (12.6 g) to give ethyl 2-(2-amino-N-methylanilino)benzo[b]thiophene-3-carboxylate (3.2 g).

$^1$H-NMR(400 MHz, CDCl$_3$) δ: 8.07(d, 1H), 7.49(d, 1H), 7.30–7.24(m, 2H), 7.13–7.08(m, 2H), 6.79–6.74(m, 2H), 4.26(q, J=7.3 Hz, 2H), 4.10(br.s, 2H), 3.36(s, 3H), 1.33(t, J=7.3 Hz, 3H)

Example 1

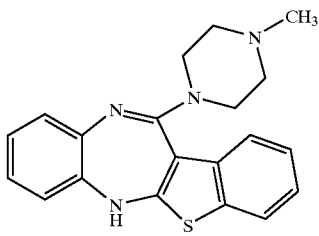

Ethyl 2-(2-aminoanilino)benzo[b]thiophene-3-carboxylate (3.5 g) and 1-methylpiperazine (20 ml) were dissolved in anisole (50 ml), titanium tetrachloride (3.1 ml) was added dropwise while stirring the mixture at room temperature. After the completion of dropwise addition, the mixture was stirred at 140° C. for 20 hours. The reaction mixture was cooled to 80° C. and poured into ice water. The resultant precipitate was filtrated. The filtrate was extracted with ethyl acetate (900 ml), washed with saturated brine, and dried over MgSO$_4$. The solvent was evaporated under reduced pressure. The residue was purified by silica gel column chromatography (ethyl acetate/methanol) and the obtained oily substance was dissolved in ethyl acetate (50 ml), to which was added a solution (10 ml) of maleic acid (580 mg) in ethyl acetate. The precipitated crystals were collected by filtration and recrystallized from ethyl acetate/methanol to give 12-(4-methylpiperazin-1-yl)-6H-[1]benzothieno[2,3-b][1,5]benzodiazepine.2 maleate (1.14 g).

melting point 248–249° C. (decomposition)

Example 2

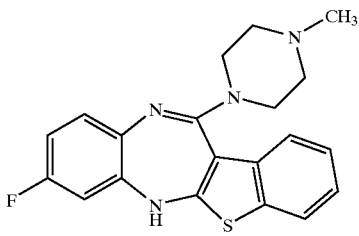

Ethyl 2-(2-amino-5-fluoroanilino)benzo[b]thiophene-3-carboxylate (24.5 g) and 1-methylpiperazine (135 ml) were dissolved in anisole (400 ml), and titanium tetrachloride (21 ml) was added dropwise while stirring the mixture at room temperature. After the completion of the dropwise addition, the mixture was stirred at 140° C. for 17 hours. The reaction mixture was cooled to 80° C. and poured into ice water. The resultant precipitate was filtrated and the filtrate was extracted with ethyl acetate, washed with saturated brine, and dried over magnesium sulfate. The solvent was evaporated under reduced pressure. The residue was purified by silica gel column chromatography (ethyl acetate/methanol)

and the obtained oily substance (17 g) was dissolved in ethyl acetate (400 ml). Thereto was added a solution of maleic acid (5.9 g) in ethyl acetate (100 ml) and ethanol (20 ml). The precipitated crystals were collected by filtration and recrystallized from ethanol to give 8-fluoro-12-(4-methylpiperazin-1-yl)-6H-[I]benzothieno[2,3-b][1,5]benzodiazepine.1 maleate (10.2 g).

melting point 225–227° C. (decomposition).

$^1$H-NMR (400 MHz, DMSO-d$_6$) δ: 8.35(s, 1H), 7.82(d, J=7.8 Hz, 1H), 7.74(br, 1H), 7.37(dd, J=8.3, 6.8 Hz, 1H), 7.25(dd, J=8.3, 6.8 Hz, 1H), 6.89(dd, 1H), 6.78(dd, 1H), 6.63(dd, 1H), 6.03(s, 2H) 2.5–4.5(br.s, 8H), 2.82(s, 3H).

IR (KBr):3435, 3283, 3060, 2837, 2614, 1616, 1580, 1463, 1387, 1353, 1152, 966, 865 cm$^{-1}$. MS:m/e 366. Anal. Calcd. for C$_{20}$H$_{19}$FN$_4$S.C$_4$H$_4$O$_4$:C, 59.74; H, 4.80; N, 11.61%. Found:C, 59.71; H, 4.82; N, 11.46%.

Example 3

Alternatively, using 2 equivalents of maleic acid, 8-fluoro-12-(4-methylpiperazin-1-yl)-6H-[1]benzothieno[2,3-b][1,5]benzodiazepine dimaleate monohydrate was obtained.

melting point 123–125° C. (decomposition)

Example 4

Alternatively, using fumaric acid instead of maleic acid, 8-fluoro-12-(4-methylpiperazin-1-yl)-6H-[1]benzothieno[2,3-b][1,5]benzodiazepine 1/2 fumarate (494 mg) was obtained.

melting point 193–195° C. (decomposition)

Example 5

Alternatively, using 2 equivalents of hydrochloric acid instead of maleic acid, 8-fluoro-12-(4-methylpiperazin-1-yl)-6H-[1]benzothieno[2,3-b][1,5]benzodiazepine.2 hydrochloride3 hydrate was obtained.

melting point 268–270° C. (decomposition)

Example 6

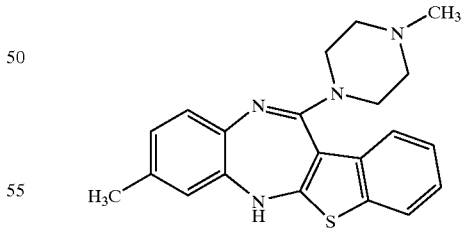

In the same manner as in Example 1 and using ethyl 2-(2-amino-5-methylanilino)benzo[b]thiophene-3-carboxylate (1.6 g), 1-methylpiperazine (8 ml), anisole (25 ml), titanium tetrachloride (1.3 ml) and maleic acid (100 mg), 8-methyl-12-(4-methylpiperazin-1-yl)-6H-[1]benzothieno[2,3-b][1,5]benzodiazepine. 3/2 maleate (166 mg) was obtained.

melting point 198–201° C. (decomposition)

Example 7

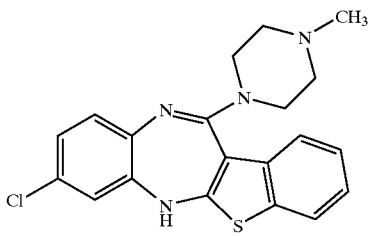

In the same manner as in Example 1 and using ethyl 2-(2-amino-5-chloroanilino)benzo[b]thiophene-3-carboxylate (2.6 g), 1-methylpiperazine (15 ml), anisole (50 ml) and titanium tetrachloride (2.3 ml), 8-chloro-12-(4-methylpiperazin-1-yl)-6H-[1]benzothieno[2,3-b][1,5]benzodiazepine (363 mg) was obtained.

melting point 87–90° C. (decomposition)

Example 8

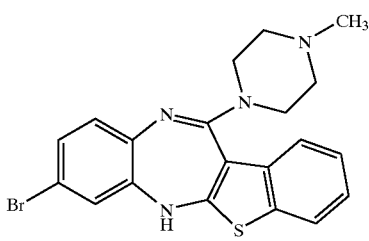

In the same manner as in Example 1 and using ethyl 2-(2-amino-5-bromoanilino)benzo[b]thiophene-3-carboxylate, 1-methylpiperazine, anisole and titanium tetrachloride, 8-bromo-12-(4-methylpiperazin-1-yl)-6H-[1]benzothieno[2,3-b][1,5]benzodiazepine is obtained.

Example 9

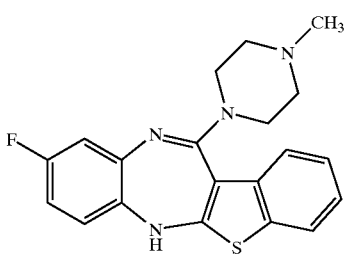

In the same manner as in Example 1 and using ethyl 2-(2-amino-4-fluoroanilino)benzo[b]thiophene-3-carboxylate, 1-methylpiperazine, anisole and titanium tetrachloride, 9-fluoro-12-(4-methylpiperazin-1-yl)-6H-[1]benzothieno[2,3-b][1,5]benzodiazepine is obtained.

Example 10

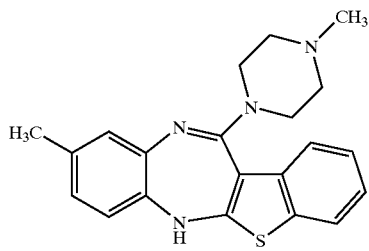

In the same manner as in Example 1 and using ethyl 2-(2-amino-4-methylanilino)benzo[b]thiophene-3-carboxylate (3.7 g), 1-methylpiperazine (19 ml), anisole (60 ml) and titanium tetrachloride (3.0 ml), 9-methyl-12-(4-methylpiperazin-1-yl)-6H-[1]benzothieno[2,3-b][1,5]benzodiazepine (1.18 g) was obtained.

melting point 184–186° C.: Anal. Calcd. for $C_{21}H_{22}N_4S$: C, 69.58; H, 6.12; N, 15.46%. Found: C, 69.45; H, 6.20; N, 15.11%.

Example 11

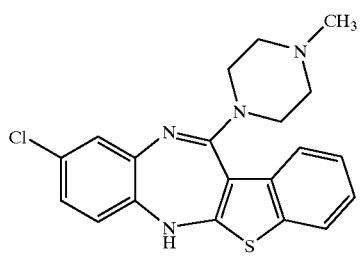

In the same manner as in Example 1 and using ethyl 2-(2-amino-4-chloroanilino)benzo[b]thiophene-3-carboxylate (3.0 g), 1-methylpiperazine (17 ml), anisole (75 ml), titanium tetrachloride (2.9 ml) and maleic acid, 9-chloro-12-(4-methylpiperazin-1-yl)-6H-[1]benzothieno[2,3-b][1,5]benzodiazepine.2 maleate. 1/2 hydrate (1.37 g) was obtained.

melting point 105–107° C. (decomposition): Anal. Calcd. for $C_{20}H_{19}N_4S \cdot 2C_4H_4O_4 \cdot 1/2H_2O$: C, 53.89; H, 4.52; N, 8.98%. Found: C, 53.94; H, 4.45; N, 9.00%.

Example 12

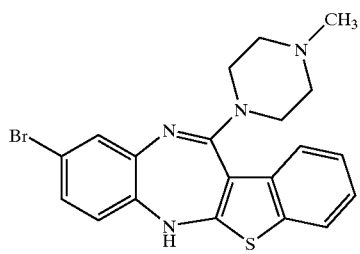

In the same manner as in Example 1 and using ethyl 2-(2-amino-4-bromoanilino)benzo[b]thiophene-3-carboxylate (3.3 g), 1-methylpiperazine (17 ml), anisole (75 ml), titanium tetrachloride (3.0 ml) and maleic acid, 9-bromo-12-(4-15 methylpiperazin-1-yl)-6H-[1]benzothieno [2,3-b][1,5]benzodiazepine.2 maleate was obtained.

melting point 113–114° C. (decomposition) Anal. Calcd. for $C_{20}H_{19}BrN_4S \cdot 2C_4H_4O_4$ : C, 50.99; H, 4.13; N, 8.50%. Found: C, 50.73; H, 4.15; N, 8.60%.

Example 13

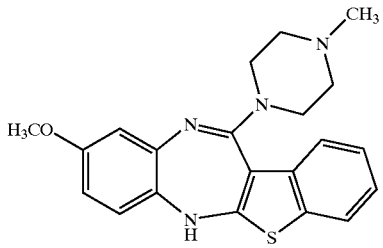

In the same manner as in Example 1 and using ethyl 2-(2-amino-4-methoxy-anilino)benzo[b]thiophene-3-carboxylate, 1-methylpiperazine, anisole and titanium tetrachloride, 9-methoxy-12-(4-methylpiperazin-1-yl)-6H-[1]benzothieno[2,3-b][1,5]benzodiazepine is obtained.

Example 14

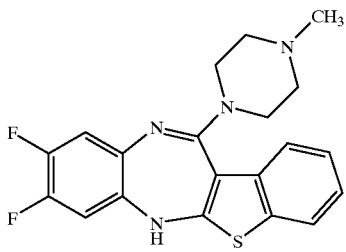

In the same manner as in Example 1 and using ethyl 2-(2-amino-4,5-difluoroanilino)benzo[b]thiophene-3-carboxylate, 1-methylpiperazine, anisole and titanium tetrachloride, 8,9-difluoro-12-(4-methylpiperazin-1-yl)-6H-[1]benzothieno[2,3-b][1,5]benzodiazepine is obtained.

Example 15

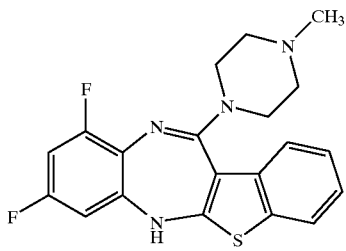

In the same manner as in Example 1 and using ethyl 2-(2-amino-3,5-difluoroanilino)benzo[b]thiophene-3-carboxylate, 1-methylpiperazine, anisole and titanium tetrachloride, 8,10-difluoro-12-(4-methylpiperazin-1-yl)-6H-[1]benzothieno[2,3-b][1,5]benzodiazepine is obtained.

Example 16

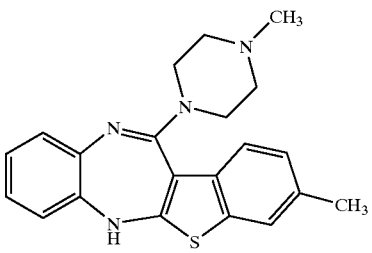

In the same manner as in Example 1 and using ethyl 2-(2-aminoanilino)-6-methylbenzo[b]thiophene-3-carboxylate (3.7 g), 1-methylpiperazine (80 ml), anisole (16 ml) and titanium tetrachloride (3 ml), 3-methyl-12-(4-methylpiperazin-1-yl)-6H-[1]benzothieno[2,3-b][1,5]benzodiazepine (1.4 g) was obtained.

$^1$H-NMR (400 MHz, CDCl$_3$) δ: 7.65(d, J=8.3 Hz, 1H), 7.38(s, 1H), 7.12(d, J=8.3 Hz, 1H), 7.03(t, J=7.8 Hz, 1H), 6.97(dd, J=7.3, 7.8 Hz, 1H), 6.86(dd, J=7.3, 5.9 Hz, 1H), 6.64(d, J=7.8 Hz, 1H), 5.10(br.s, 1H), 4.20–1.75(m, 8H), 2.38(s, 3H), 2.33(s, 3H).

Example 17

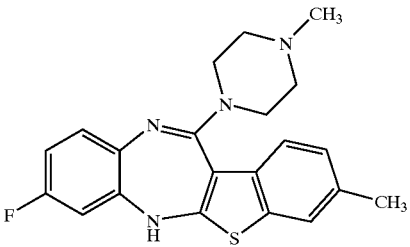

In the same manner as in Example 1 and using ethyl 2-(2-amino-5-fluoroanilino)-6-methylbenzo[b]thiophene-3-carboxylate, 1-methylpiperazine, anisole, titanium tetrachloride and hydrochloric acid, 8-fluoro-3-methyl-12-(4-methylpiperazin-1-yl)-6H-[1]benzothieno[2,3-b][1,5]benzodiazepine.2 hydrochloride.3/2 hydrate was obtained.

melting point 273–275° C. (decomposition)

Example 18

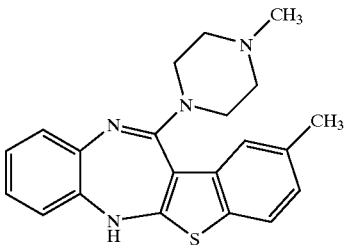

In the same manner as in Example 1 and using methyl 2-(2-aminoanilino)-5-methylbenzo[b]thiophene-3-carboxylate, 1-methylpiperazine, anisole and titanium tetrachloride, 2-methyl-12-(4-methylpiperazin-1-yl)-6H-[1]benzothieno[2,3-b][1,5]benzodiazepine is obtained.

Example 19

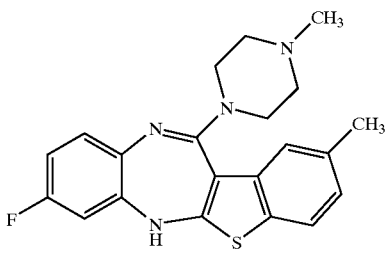

In the same manner as in Example 1 and using methyl 2-(2-amino-5-fluoroanilino)-5-methylbenzo[b]thiophene-3-carboxylate (1.82 g), 1-methylpiperazine (9.7 ml), anisole (30 ml), titanium tetrachloride (1.51 ml) and maleic acid, 8-fluoro-2-methyl-12-(4-methylpiperazin-1-yl)-6H-[1]benzothieno[2,3-b][1,5]benzodiazepine.1 maleic acid.1/2H$_2$O (928 mg) was obtained.

melting point:199–201° C. (decomposition). Anal. Calcd. for $C_{21}H_{21}FN_4S.C_4H_4O_4.1/2H_2O$: C, 59.39; H, 5.18; N, 11.08%. Found: C, 59.49; H, 4.98; N, 11.04%.

Example 20

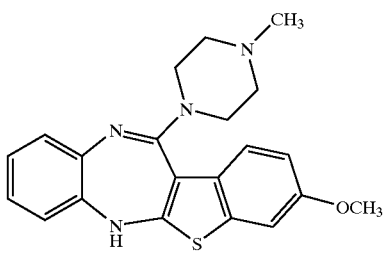

In the same manner as in Example 1 and using ethyl 2-(2-aminoanilino)-6-methoxybenzo[b]thiophene-3-carboxylate, 1-methylpiperazine, anisole and titanium tetrachloride, 3-methoxy-12-(4-methylpiperazin-1-yl)-6H-[1]benzothieno[2,3-b][1,5]benzodiazepine is obtained.

Example 21

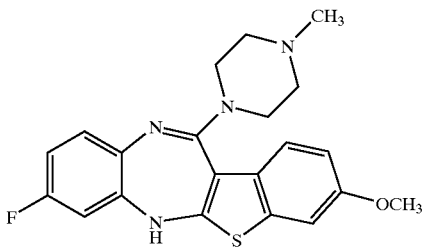

In the same manner as in Example 1 and using ethyl 2-(2-amino-5-fluoroanilino)-6-methoxybenzo[b]thiophene-3-carboxylate, 1-methylpiperazine, anisole and titanium tetrachloride, 8-fluoro-3-methoxy-12-(4-methylpiperazin-1-yl)-6H-[1]benzothieno[2,3-b][1,5]benzodiazepine is obtained.

Example 22

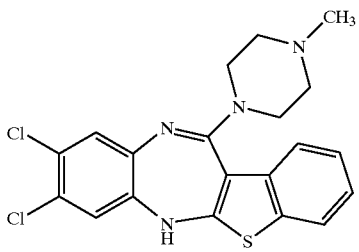

In the same manner as in Example 1 and using ethyl 2-(2-amino-4,5-dichloroanilino)benzo[b]thiophene-3-carboxylate (5.3 g), 1-methylpiperazine (27 ml), anisole (120 ml), titanium tetrachloride (4.8 ml) and fumaric acid, 8,9-dichloro-12-(4-methylpiperazin-1-yl)-6H-[1]benzothieno[2,3-b][1,5]benzodiazepine 1 fumarate (571 mg) was obtained.

melting point 243–245° C. (decomposition): Anal. Calcd. for $C_{20}H_{18}Cl_2N_4S.C_4H_4O_4$: C, 54.04; H, 4.16; N, 10.50%. Found:C, 54.00; H, 4.10; N, 10.41%.

Example 23

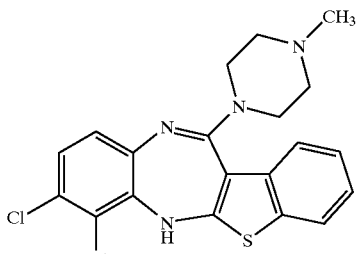

In the same manner as in Example 1 and using ethyl 2-(6-amino-2,3-dichloroanilino)benzo[b]thiophene-3-carboxylate (4.2 g), 1-methylpiperazine (22 ml), anisole (100 ml), titanium tetrachloride (3.9 ml) and fumaric acid, 7,8-dichloro-12-(4-methylpiperazin-1-yl)-6H-[1]benzothieno[2,3-b][1,5]benzodiazepine 1 fumarate (660 mg) was obtained.

melting point 235–236° C. (decomposition). Anal. Calcd. for $C_{20}H_{18}Cl_2N_4S.C_4H_4O_4$: C, 54.04; H, 4.16; N, 10.50%. Found: C, 53.69; H, 4.19; N, 10.33%.

Example 24

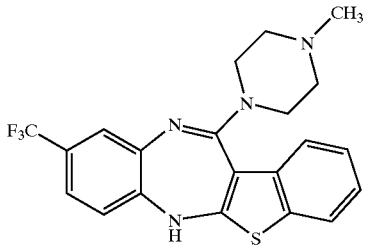

In the same manner as in Example 1 and using ethyl 2-(2-amino-4-trifluoromethylanilino)benzo[b]thiophene-3-carboxylate (2.8 g), 1-methylpiperazine (15 ml), anisole (60 ml), titanium tetrachloride (2.5 ml) and maleic acid, 12-(4-methylpiperazin-1-yl)-9-trifluoromethyl-6H-[1]benzothieno[2,3-b][1,5]benzodiazepine2 maleate (363 mg) was obtained.

melting point 128–129° C.: Anal. Calcd. for C$_{21}$, H$_{19}$F$_3$N$_4$S.2C$_4$H$_4$O$_4$: C, 53.70; H, 4.20; N, 8.64%. Found: C, 53.56; H, 4.26; N, 8.56%.

Example 25

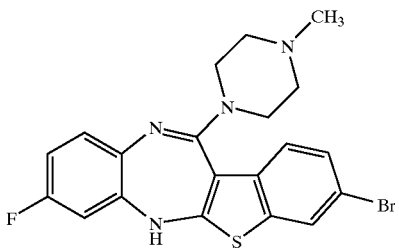

In the same manner as in Example 1 and using ethyl 6-bromo-2-(2-amino-5-fluoroanilino)benzo[b]thiophene-3-carboxylate (3.8 g), 1-methylpiperazine (16 ml), anisole (85 ml) and titanium tetrachloride (3.0 ml), 3-bromo-8-fluoro-12-(4-methylpiperazin-1-yl)-6H-[1]benzothieno[2,3-b][1,5]benzodiazepine (1.16 g) was obtained.

melting point 219–221° C.: Anal. Calcd. for C$_{20}$H$_{18}$BrFN$_4$S: C, 53.94; H, 4.07; N, 12.58%. Found: C, 53.72; H, 3.88; N, 12.41%.

Example 26

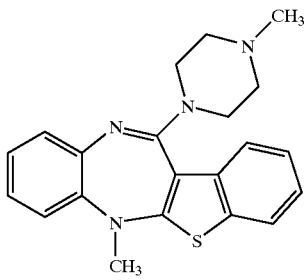

In the same manner as in Example 1 and using ethyl 2-(N-methyl-2-nitroanilino)benzo[b]thiophene-3-carboxylate (3.2 g), 1-methylpiperazine, anisole (80 ml) and titanium tetrachloride (3.5 ml), 6-methyl-12-(4-methylpiperazin-1-yl)[1]benzothieno[2,3-b][1,5]benzodiazepine (166 mg) was obtained.

melting point 88–90° C.

STARTING MATERIAL SYNTHESIS EXAMPLE 50

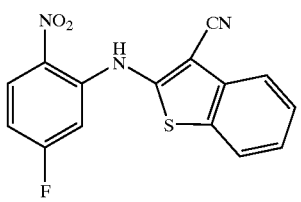

To a solution of 2-aminobenzo[b]thiophene-3-carbonitrile (116 g), dimethylformamide (370 ml) and 2,4-difluoronitrobenzene (73 ml) was added pulverized potassium carbonate (276 g), and the mixture was stirred at 55° C. for 5.5 hours. The reaction mixture was stirred under ice-cooling for 30 minutes and water (1.9 L) was added. The mixture was further stirred for 30 minutes. The precipitated crystals were filtered by suction and washed with water (1.9 L) and dried in a drying box overnight to give crude crystals (198 g). The obtained crude crystals were suspended in ethyl acetate (700 ml) and the mixture was stirred under reflux with heating while removing water for 2 hours. The reaction mixture was cooled and stirred at 20° C. for 1 hour. The precipitated crystals were filtered by suction, washed with ethyl acetate (150 ml) and dried to give 2-(5-fluoro-2-nitroanilino)benzo[1]thiophene-3-carbonitrile (123 g) as red crystalline powder.

melting point 161–163° C.

STARTING MATERIAL SYNTHESIS EXAMPLE 51

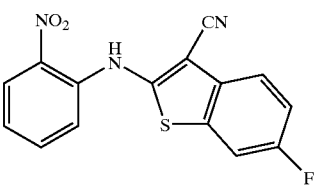

To a solution of 2-amino-6-fluorobenzo[b]thiophene-3-carbonitrile (15 g), tetrahydrofuran (140 ml) and 2-fluoronitrobenzene (11.3 g) was added portionwise 60% sodium hydride (3.5 g) under ice-cooling and the mixture was stood still at 5° C. for 30 minutes. The precipitated crystals were filtered by suction, washed with isopropyl ether (120 ml) and dried to give 6-fluoro-2-(2-nitroanilino)benzo[b]thiophene-3-carbonitrile (8.0 g).

$^1$H-NMR(400 MHz, CDCl$_3$) δ: 10.13(br.s, 1H), 8.28(d, J=8.3 Hz, 1H), 7.75(m, 1H) 7.61–7.57(m, 2H), 7.43(m, 1H), 7.25(m, 1H), 7.10(m, 1H)

STARTING SYNTHESIS MATERIAL EXAMPLE 52

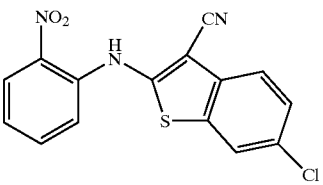

In the same manner as in Starting Material Synthesis Example 51 and using 2-amino-6-chlorobenzo[b]thiophene-3-carbonitrile and 2-fluoronitrobenzene, 6-chloro-2-(2-nitroanilino)benzo[b]thiophene-3-carbonitrile is obtained.

STARTING MATERIAL SYNTHESIS EXAMPLE 53

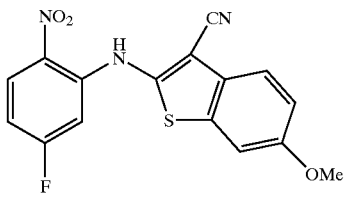

In the same manner as in Starting Material Synthesis Example 51 and using 2-amino-6-methoxybenzo[b]thiophene-3-carbonitrile (5.2 g) and 2,4-difluoro-nitrobenzene (4.0 g), 6-methoxy-2-(5-fluoro-2-nitroanilino)benzo[b]thiophene-3-carbonitrile (2.5 g) was obtained.

$^1$H-NMR(400 MHz, CDCl$_3$) δ: 10.04(br.s, 1H), 8.33(m, 1H), 7.74(d, J=8.8 Hz, 1H), 7.23(s, 1H), 7.13(d, J=8.8 Hz, 1H), 7.04(d, J=10.3 Hz, 1H), 6.70(m, 1H), 3.88(s, 3H)

STARTING MATERIAL SYNTHESIS EXAMPLE 54

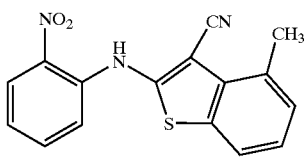

In the same manner as in Starting Material Synthesis Example 51 and using 2-amino-4-methylbenzo[b]thiophene-3-carbonitrile (3.8 g), 2-chloronitrobenzene(3.5 g) and dimethyl sulfoxide (45 ml), 4-methyl-2-(2-nitroanilino)benzo[b]thiophene-3-carbonitrile (5.8 g) was obtained.

$^1$H-NMR (400 MHz, CDCl$_3$) δ: 10.31 (br.s, 1H), 8.28(d, J=8.3 Hz, 1H), 7.66–7.52(m, 3H), 7.27–7.11(m, 2H), 7.08(d, J=7.4 Hz, 1H), 2.81(s, 3H)

STARTING MATERIAL SYNTHESIS EXAMPLE 55

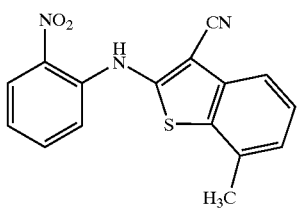

In the same manner as in Starting Material Synthesis Example 51 and using 2-amino-7-methylbenzo[b]thiophene-3-carbonitrile and 2-fluoronitrobenzene, 7-methyl-2-(2-nitroanilino)benzo[b]thiophene-3-carbonitrile is obtained.

STARTING MATERIAL SYNTHESIS EXAMPLE 56

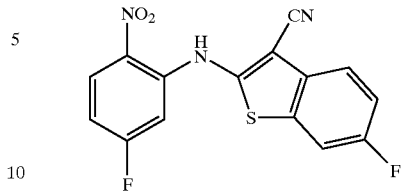

In the same manner as in Starting Material Synthesis Example 51 and using 2-amino-6-fluorobenzo[b]thiophene-3-carbonitrile (4.9 g) and 2,4-difluoro-nitrobenzene (4.1 g), 6-fluoro-2-(5-fluoro-2-nitroanilino)benzo[b]thiophene-3-carbonitrile (7.8 g) was obtained.

$^1$H-NMR(400 MHz, CDCl$_3$) δ: 10.23(br.s, 1H), 8.35(dd, J=9.3, 5.1 Hz, 1H), 7.81(dd, J=8.8, 4.9 Hz, 1H), 7.48(d, J=8.3 Hz, 1H), 7.31–7.28(m, 1H), 7.14(d, J=9.3 Hz, 1H), 6.76(m, 1H)

STARTING MATERIAL SYNTHESIS EXAMPLE 57

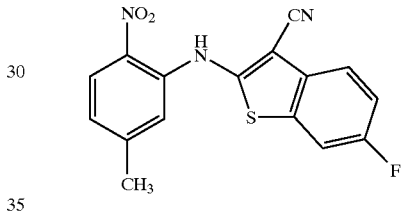

In the same manner as in Starting Material Synthesis Example 51 and using 2-amino-6-fluorobenzo[b]thiophene-3-carbonitrile (5.0 g), 3-fluoro-4-nitrotoluene (4.7 g) and dimethyl sulfoxide (55 ml), 6-fluoro-2-(5-methyl-2-nitroanilino)benzo[b]thiophene-3-carbonitrile (7.5 g) was obtained.

$^1$H-NMR (400 MHz, CDCl$_3$) δ: 10.19(br.s, 1H), 8.17(d, J=8.8 Hz, 1H), 7.75(m, 1H), 7.44(d, J=8.3 Hz, 1H), 7.24–7.22(m, 2H), 6.89(d, J=8.8 Hz, 1H), 2.41(s, 3H)

STARTING MATERIAL SYNTHESIS EXAMPLE 58

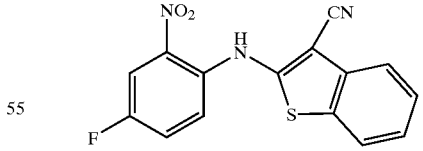

In the same manner as in Starting Material Synthesis Example 51 and using 2-aminobenzo[b]thiophene-3-carbonitrile (4.0 g) and 2,5-difluoronitrobenzene (3.7 g), 2-(4-fluoro-2-nitroanilino)benzo[b]thiophene-3-carbonitrile (6.7 g) was obtained.

$^1$H-NMR (400 MHz, CDCl$_3$) δ: 9.94(br.s, 1H), 8.01(m, 1H), 7.79(d, J=7.9 Hz, 1H), 7.71(d, J=8.3 Hz, 1H), 7.62(m, 1H), 7.50(dd, J=7.3, 8.3 Hz, 1H), 7.42–7.35(m, 2H)

STARTING MATERIAL SYNTHESIS EXAMPLE 59

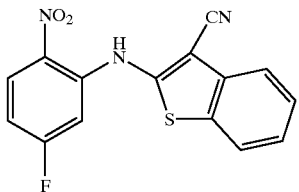

Sodium hydrosulfite (86%, 233 g) was suspended in dimethylformamide (240 ml) and the suspension was heated to 110° C. To this suspension was added dropwise at 110° C. a solution of 2-(5-fluoro-2-nitroanilino)benzo[b]thiophene-3-carbonitrile (120 g), dimethylformamide (720 ml) and water (27.5 ml), which solution had been heated to 65–70° C. The reaction mixture was stirred at 110° C. for 1 hour and cooled to 20° C. Water (3.3 L) was added in 6 portions over 1 hour and the mixture was stirred at 20° C. for 1.5 hours. The precipitated crystals were filtered by suction and washed with water (2 L) to give 2-(2-amino-5-fluoroanilino) benzo[b]thiophene-3-carbonitrile (158 g, (wet weight)) as ocher crystals.

melting point 178–180° C. (decomposition)

Example 27

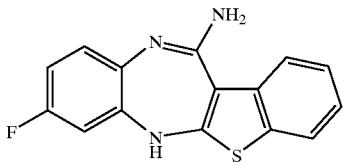

2-(2-Amino-5-fluoroanilino)benzo[b]thiophene-3-carbonitrile (155 g) was suspended in a mixture of methanol (250 ml) and water (200 ml) and 35% aqueous hydrochloric acid (42 ml) was added. The mixture was stirred under reflux with heating for 5.5 hours. The reaction mixture was cooled and stirred at 20° C. for 1 hour. The precipitated crystals were filtered by suction, washed successsively with water (500 ml) and isopropyl alcohol (200 ml) and dried in a drying box overnight to give 12-amino-8-fluoro-6H-[1] benzothieno[2,3-b][1,5]benzodiazepine.1 hydrochloride (104 g) as yellow crystals.

melting point 213–216° C. (decomposition)

Example 28

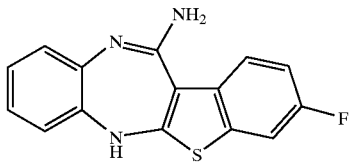

Tin(II) chloride (50 g) was dissolved in a 18% hydrochloric acid (250 ml) solution heated to 50° C., and a suspension of 6-fluoro-2-(2-nitroanilino)benzo[b] thiophene-3-carbonitrile (20 g) in ethanol (280 ml) was added. The mixture was refluxed under heating for 4 hours. Then, the reaction mixture was cooled to 40° C. and poured into water (1 L) and the mixture was stood still for 30 minutes. The precipitated crystals were filtered by suction and washed with water (500 ml) to give 12-amino-3-fluoro-6H-[1]benzothieno[2,3-b][1,5]benzodiazepine 1 hydrochloride (15 g).

$^1$H-NMR(400 MHz, DMSO-d$_6$) δ: 11.46(s, 1H), 9.92(s, 1H), 9.02(s, 1H), 9.00(s, 1H), 7.84(d, J=6.3 Hz, 1H), 7.69 (m, 1H), 7.31(m, 1H), 7.20–6.98(m, 4H)

Example 29

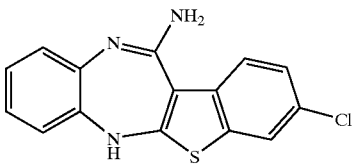

In the same manner as in Example 28 and using 6-chloro-2-(2-nitroanilino)benzo[b]thiophene-3-carbonitrile, 12-amino-3-chloro-6H-[1]benzothieno[2,3-b][1,5] benzodiazepine 1 hydrochloride is obtained.

Example 30

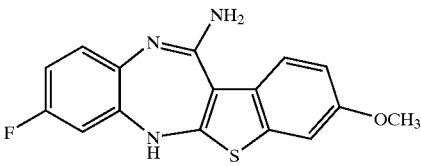

In the same manner as in Example 28 and using 6-methoxy-2-(5-fluoro-2-nitroanilino)benzo[b]thiophene-3-carbonitrile (2.5 g), 12-amino-8-fluoro-3-methoxy-6H-[1] benzothieno[2,3-b][1,5]benzodiazepine 1 hydrochloride (2.1 g) was obtained.

$^1$H-NMR(400 MHz, DMSO-d$_6$) δ: 11.68(br.s, 1H), 10.02 (br.s, 1H), 9.09(br.s, 1H), 9.01(br.s, 1H), 7.58(d, J=8.8 Hz, 1H), 7.53(s, 1H), 7.10–6.95(m, 3H), 6.86(d, J=9.3 Hz, 1H), 3.78(s, 3H)

Example 31

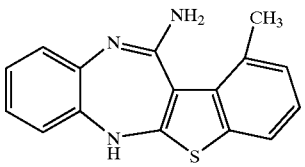

In the same manner as in Example 28 and using 4-methyl-2-(2-nitroanilino)benzo[b]thiophene-3-carbonitrile (2.5 g), 12-amino-1-methyl-6H-[1]benzothieno[2,3-b][1,5] benzodiazepine.1 hydrochloride was obtained.

$^1$H-NMR(400MHz, DMSO-d$_6$) δ: 11.32(s, 1H), 10.02(s, 1H), 9.08(s, 1H), 8.64(s, 1H), 7.71(d, J=7.3 Hz, 1H), 7.27–7.15(m, 5H), 7.02(d, 7.3 Hz, 1H), 2.36(s, 3H)

Example 32

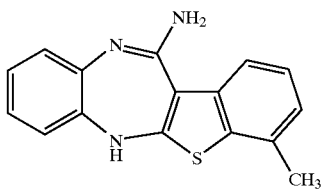

In the same manner as in Example 28 and using 7-methyl-2-(2-nitroanilino)benzo[b]thiophene-3-carbonitrile, 12-amino-4-methyl-6H-[1]benzothieno[2,3-b][1,5]benzodiazepine 1 hydrochloride is obtained.

Example 33

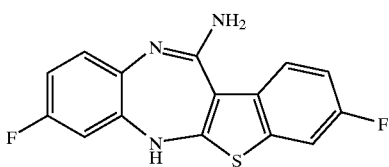

In the same manner as in Example 28 and using 6-fluoro-2-(5-fluoro-2-nitroanilino)benzo[b]thiophene-3-carbonitrile (7.8 g), 12-amino-3,8-difluoro-6H-[1]benzothieno[2,3-b][1,5]benzodiazepine 1 hydrochloride (4.8 g) was obtained.

$^1$H-NMR(400 MHz, DMSO-d$_6$) δ: 11.51(s, 1H), 10.08(s, 1H), 9.05(s, 2H), 7.86(d, J=8.7 Hz, 1H), 7.70(m, 1H), 7.32(m, 1H), 7.11(m, 1H), 7.00(m, 1H), 6.86(d, J=9.3 Hz, 1H)

Example 34

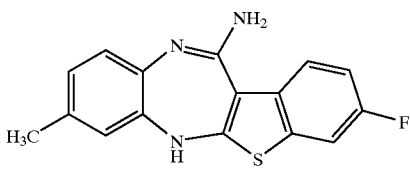

In the same manner as in Example 28 and using 6-fluoro-2-(5-methyl-2-nitroanilino)benzo[b]thiophene-3-carbonitrile (7.4 g), 12-amino-3-fluoro-8-methyl-6H-[1]benzothieno[2,3-b][1,5]benzodiazepine. 1 hydrochloride (8.5 g) is obtained.

$^1$H-NMR(400 MHz, DMSO-d$_6$) δ: 11.53(br.s, 1H), 9.92 (br.s, 1H), 9.02(br.s, 1H), 8.95(br.s, 1H), 7.84(d, J=8.8 Hz, 1H), 7.68(d, J=8.7 Hz, 1H), 7.30(dd, J=8.8, 9.3 Hz, 1H), 6.96–6.91(m, 2H), 6.79(s, 1H), 2.22(s, 3H)

Example 35

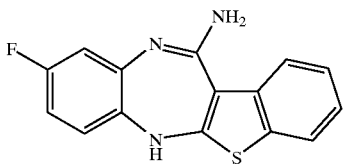

In the same manner as in Example 28 and using 2-(4-fluoro-2-nitroanilino)benzo[b]thiophene-3-carbonitrile (6.7 g), 12-amino-9-fluoro-6H-[1]benzothieno[2,3-b][1,5]benzodiazepine. 1 hydrochloride (4.8 g) was obtained.

$^1$H-NMR(400 MHz, DMSO-d$_6$) δ: 11.73(s, 1H), 10.06(s, 1H), 9.14(s, 1H), 9.11(s, 1H), 7.87(d, J=7.8 Hz, 1H), 7.68(d, J=7.8 Hz, 1H), 7.42(dd, J=8.3, 7.3 Hz, 1H), 7.28(dd, J=7.8, 7.3 Hz, 1H), 7.10–7.04(m, 2H), 6.93(dd, J=9.3, 2.4 Hz, 1H)

Example 36

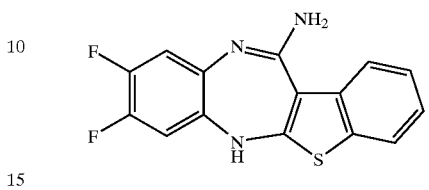

In the same manner as in Starting Material Synthesis Example 51 and using 2-aminobenzo[b]thiophene-3-carbonitrile (5.0 g) and 2,4,5-trifluoronitrobenzene (5.1 g), crude crystals (8.7 g) of 2-(4,5-difluoro-2-nitroanilino)benzo[b]thiophene-3-carbonitrile were obtained. Without purification, in the same manner as in Example 28 and using tin(II) chloride dihydrate (95 g), 18% hydrochloric acid (65 ml) and ethanol (120 ml), 12-amino-8, 9-difluoro-6H-[1]benzothieno[2,3-b][1,5]benzodiazepine.1 hydrochloride (7.7 g) was obtained.

$^1$H-NMR(400 MHz, DMSO-d$_6$) δ: 11.36(br.s, 1H), 9.97 (s, 1H), 9.16(br.s, 1H), 9.09(br.s, 1H), 7.90(d, J=7.8 Hz, 1H), 7.69(d, J=8.3 Hz, 1H), 7.44(t, J=7.8 Hz, 1H), 7.32(dd, J=7.8, 7.3 Hz, 1H), 7.21(dd, J=7.9, 8.7 Hz, 1H), 7.05(t, J=7.8 Hz, 1H)

Example 37

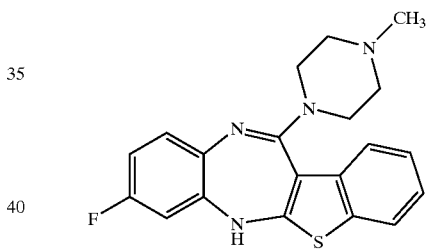

To 12-(4-methylpiperazin-1-yl)-8-fluoro-6H-[1]benzothieno[2,3-b][1,5]benzodiazepine (63.5 g) was added ethanol (320 ml) and the mixture was heated for dissolution. Active charcoal (1.9 g) was added for natural filtration and the mixture was washed with ethanol (220 ml). The solution was heated to 35° C. and a solution of maleic acid (20.1 g) in an aqueous organo solution (95 ml, upon natural filtration after dissolution) was added dropwise with stirring. The solution was stirred at 35° C. for 1 hour, cooled and stirred at 20° C. for 2 hours. The precipitated crystals were collected by filtration, washed with ethanol (130 ml) and dried at 50° C. to give 12-(4-methylpiperazin-1-yl)-8-fluoro-6H-[1]benzothieno[2,3-b][1,5]benzodiazepine 1 maleate (50.5 g) as pale-yellow crystals.

melting point 225–227° C. (decomposition)

Using a suitable organic acid or inorganic acid instead of maleic acid used in the above-mentioned Examples, the following salt compounds can be synthesized.

Example 38

12-(4-methylpiperazin-1-yl)-8-fluoro-6H-[1]benzothieno[2,3-b][1,5]benzodiazepine.1 methanesulfonate.

melting point 303.5° C. (decomposition).

$^1$H-NMR(400 MHz, DMSO-d$_6$) δ: 9.64(br.s, 1H), 8.36(s, 1H), 7.82(d, 1H), 7.38(dd, 1H), 7.25(dd, 1H), 6.89(dd, 1H), 6.79(dd, 1H), 6.62(d, 1H), 3.10–3.60(m, 8H), 2.85(s, 3H), 2.30(s, 3H).

IR (KBr): 3246, 1618, 1518, 1385 cm$^{-1}$. MS: m/e 366. Anal. Calcd. for $C_{20}H_{19}FN_4S \cdot CH_4O_3S$: C, 54.53; H, 5.01; N, 12.11%. Found: C, 54.35; H, 5.04; N, 11.94%.

Example 39

12-(4-methylpiperazin-1-yl)-8-fluoro-6H-[1]benzothieno[2,3-b][1,5]benzodiazepine.2 nitrate melting point 170° C. (decomposition).

$^1$H-NMR (400 MHz, DMSO-d$_6$) δ: 9.78(br.s, 1H), 7.92(d, 1H), 7.58–7.77(m, 1H), 7.45(dd, 1H), 7.33(dd, 1H), 6.77–6.98(m, 3H), 3.20–3.90(m, 8H), 2.84(s, 3H).

IR (KBr): 3462, 3043, 1599, 1508 cm$^{-1}$. MS:m/e 366. Anal. Calcd. for $C_{20}H_{19}FN_4S \cdot 2HNO_3 \cdot 0.5H_2O$: C, 47.90; H, 4.42; N, 16.76%. Found: C, 47.89; H, 4.44; N, 16.75%.

Example 40

12-(4-methylpiperazin-1-yl)-8-fluoro-6H-[1]benzothieno[2,3-b][1,5]benzodiazepine. 1.5 sulfate melting point 236–239° C.

$^1$H-NMR(400 MHz, DMSO-d$_6$) δ: 9.69(br, 1H), 7.87(d, 1H), 7.80–7.86(m, 1H), 7.42(dd, 1H), 7.30(dd, 1H), 6.60–7.10(m, 3H), 3.80–4.40(m, 8H). 2.89(s, 3H).

IR (KBr): 3406, 2986, 1597, 1510 cm$^{-1}$. MS:m/e 366. Anal. Calcd. for $C_{20}H_{19}FN_4S \cdot 1.5H_2SO_4 \cdot 1.5H_2O$: C, 44.43; H, 4.66; N, 10.36%. Found: C, 44.45; H, 4.65; N, 10.31%

Example 41

12-(4-methylpiperazin-1-yl)-8-fluoro-6H-[1]benzothieno([2,3-b][1,5]benzodiazepine.2 phosphate melting point 189–192° C.

$^1$H-NMR(400 MHz, DMSO-d$_6$) δ: 8.29(s, 1H), 7.81(d, 1H), 7.71(d, 1H), 7.35(dd, 1H), 7.23(dd, 1H), 6.87(dd, 3H), 6.70(d, 1H) 6.56(d, 1H), 2.40–3.90(m, 8H), 2.44(s, 3H).

IR(KBr):3429, 2922, 1597, 1510 cm$^{-1}$. MS:m/e 366. Anal. Calcd. for $C_{20}H_{19}FN_4S \cdot 2H_3PO_4 \cdot 1H_2O$: C, 41.38; H, 4.69; N, 9.65%. Found: C, 41.54; H, 5.11; N, 9.66%.

Example 42

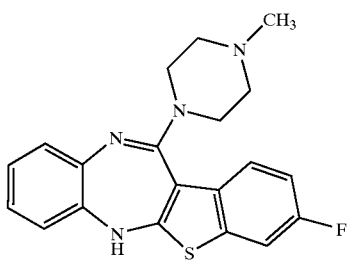

12-Amino-3-fluoro-6H-[1]benzothieno[2,3-b][1,5]benzodiazepine.1 hydrochloride (12 g) was dissolved in N-methylpiperazine (140 ml) and the mixture was stirred under reflux with heating for 3 hours. The reaction mixture is cooled to 40° C., extracted with ethyl acetate (250 ml) and washed with saturated brine (100 ml). The ethyl acetate layer is dried over magnesium sulfate. The solution was naturally filtrated and the solvent was evaporated under reduced pressure. The residue was purified by silica gel column chromatography (ethyl acetate:methanol) to give crude crystals of 3-fluoro-12-(4-methylpiperazin-1-yl)-6H-[1]benzothieno[2,3-b][1,5]benzodiazepine. The obtained crude crystals were dissolved in ethyl acetate (30 ml) and a solution of maleic acid (1.83 g) in ethanol (20 ml) was added. The precipitated crystals were collected by filtration and recrystallized from aqueous ethanol to give 3-fluoro-12-(4-methylpiperazin-1-yl)-6H-[1]benzothieno[2,3-b][1,5]benzodiazepine.1 maleate (2.82 g).

melting point 209° C. Anal. Calcd. for $C_{20}H_{19}FN_4S \cdot C_4H_4O_4$: C, 59.74; H, 4.80; N, 11.61%. Found: C, 59.66; H, 4.69; N, 11.56%.

Example 43

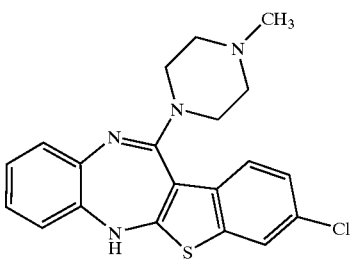

In the same manner as in Example 42 and using 12-amino-3-chloro-6H-[1]benzothieno[2,3-b][1,5]benzodiazepine.1 hydrochloride and N-methylpiperazine, 3-chloro-12-(4-methylpiperazin-1-yl)-6H-[1]benzothieno[2,3-b][1,5]benzodiazepine is obtained.

Example 44

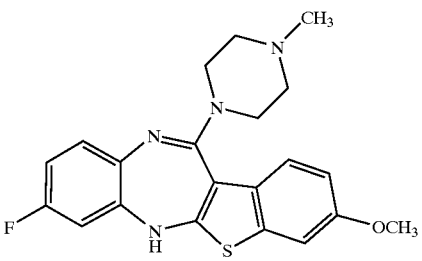

In the same manner as in Example 42 and using 12-amino-8-fluoro-3-methoxy-6H-[1]benzothieno[2,3-b][1,5]benzodiazepine.1 hydrochloride (1.6 g), N-methylpiperazine (50 ml) and citric acid, crude crystals (1.0 g) of 8-fluoro-3-methoxy-12-(4-methylpiperazin-1-yl)-6H-[1]benzothieno[2,3-b][1,5]benzodiazepine was obtained. The crystals were dissolved in ethanol (10 ml) and a solution of citric acid (552 mg) in ethanol (10 ml) was added. The precipitated salt was recrystallized from a a mixed solvent of ethyl acetate and ethanol to give 8-fluoro-3-methoxy-12-(4-methylpiperazin-1-yl)-6H-[1]benzothieno[2,3-b][1,5]benzodiazepine.1 citrate.dihydrate (204 mg).

melting point 118–120° C. Anal. Calcd. for $C_{21}H_{21}FN_4OS \cdot C_6H_8O_7 \cdot 2H_2O$: C, 51.92; H, 5.33; N, 8.97%. Found: C, 52.18; H, 5.19; N, 8.63%.

Example 45

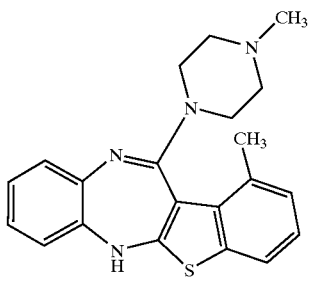

In the same manner as in Example 42 and using 12-amino-1-methyl-6H-[1]benzothieno[2,3-b][1,5]benzodiazepine.1 hydrochloride and N-methylpiperazine, 1-methyl-12-(4-methylpiperazin-1-yl)-6H-[1]benzothieno[2,3-b][1,5]benzodiazepine is obtained.

Example 46

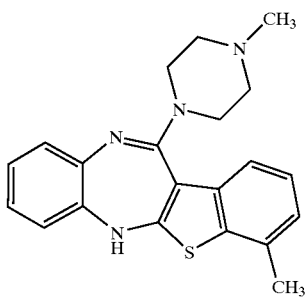

In the same manner as in Example 42 and using 12-amino-4-methyl-6H-[1]benzothieno[2,3-b][1,5]benzodiazepine.1 hydrochloride and N-methylpiperazine, 4-methyl-12-(4-methylpiperazin-1-yl)-6H-[1]benzothieno[2,3-b][1,5]benzodiazepine is obtained.

Example 47

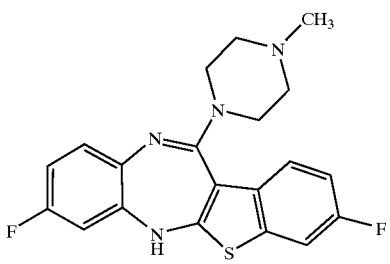

In the same manner as in Example 42 and using 12-amino-3,8-difluoro-6H-[1]benzothieno[2,3-b][1,5]benzodiazepine.1 hydrochloride (8.0 g), N-methylpiperazine (100 ml) and maleic acid, 3,8-difluoro-12-(4-methylpiperazin-1-yl)-6H-[1]benzothieno[2,3-b][1,5]benzodiazepine.1 maleate (3.4 g) was obtained.

melting point 211–213° C. Anal. Calcd. for $C_{20}H_{18}FN_4S.C_4H_4O_4$: C, 57.59; H, 4.43; N, 11.19%. Found: C, 57.58; H, 4.37; N, 11.10%.

Example 48

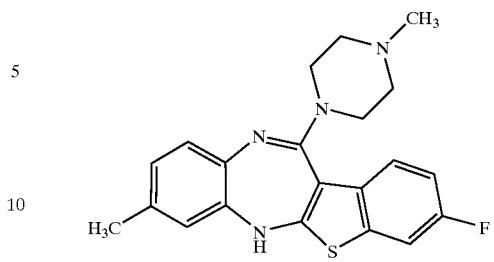

In the same manner as in Example 42 and using 12-amino-3-fluoro-8-methyl-6H-[1]benzothieno[2,3-b][1,5]benzodiazepine.1 hydrochloride (8.5 g), N-methylpiperazine (100 ml) and hydrochloric acid, 3-fluoro-8-methyl-12-(4-methylpiperazin-1-yl)-6H-[1]benzothieno[2,3-b][1,5]benzodiazepine.2 hydrochloride was obtained.

melting point 240–242° C. (decomposition).
$^1$H-NMR(400 MHz, DMSO-d$_6$) δ: 11.82(br.s, 2H), 11.09 (br.s, 1H), 7.89–7.54(m, 2H), 7.33–7.26(m, 2H), 6.98–6.96 (m, 2H), 4.79–2.87(m, 11H), 2.24(s, 3H)

Example 49

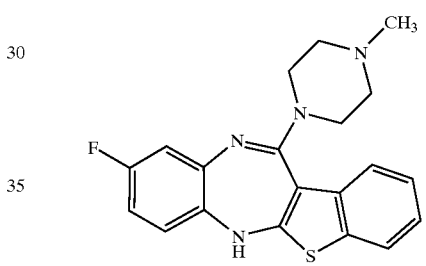

In the same manner as in Example 42 and using 12-amino-9-fluoro-6H-[1]benzothieno[2,3-b][1,5]benzodiazepine.1 hydrochloride (2.0 g), N-methylpiperazine (40 ml) and maleic acid, 9-fluoro-12-(4-methylpiperazin-1-yl)-6H-[1]benzothieno[2,3-b][1,5]benzodiazepine.2 maleate (1.2 g) was obtained.

melting point 136–137° C. Anal. Calcd. for $C_{20}H_{19}FN_4S.2C_4H_4O_4$: C, 56.18; H, 4.55; N, 9.36%. Found: C, 56.14; H, 4.58; N, 9.32%.

Example 50

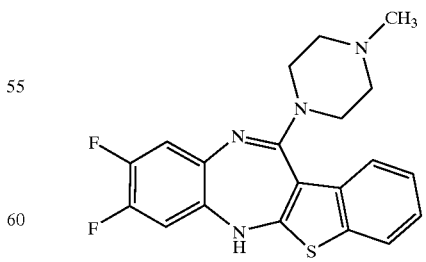

In the same manner as in Example 42 and using 12-amino-8,9-difluoro-6H-[1]benzothieno[2,3-b][1,5]benzodiazepine.1 hydrochloride (4.0 g), N-methylpiperazine (40 ml) and maleic acid, 8,9-difluoro- 12-(4-methylpiperazin-1-yl)-6H-[1]benzothieno[2,3-b][1,5]benzodiazepine.1 maleate (924 mg) was obtained.

melting point 144–146° C. (decomposition). Anal. Calcd. for $C_{20}H_{18}F_2N_4S \cdot C_4H_4O_4$: C, 57.59; H, 4.43; N, 11.19%. Found:C, 57.39; H, 4.44; N, 11.10%.

Example 51

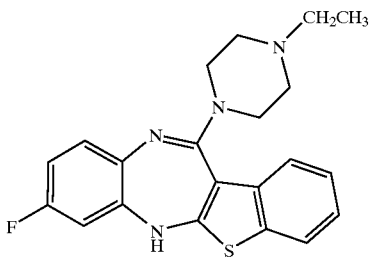

In the same manner as in Example 42 and using 12-amino-8-fluoro-6H-[1]benzothieno[2,3-b][1,5]benzodiazepine.1 hydrochloride (1.3 g), N-ethylpiperazine (25 ml) and maleic acid, 12-(4-ethylpiperazin-1-yl)-8-fluoro-6H-[1]benzothieno[2,3-b][1,5]benzodiazepine.1 maleate (731 mg) was obtained.

melting point 211–212° C. Anal. Calcd. for $C_{21}H_{21}FN_4S \cdot C_4H_4O_4$: C, 60.47; H, 5.07; N, 11.28%. Found:C, 60.30; H, 5.03; N, 11.18%.

Example 52

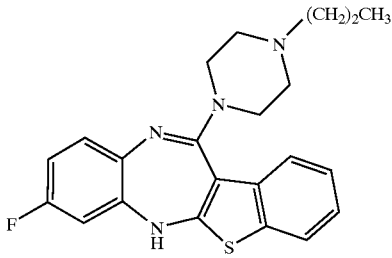

In the same manner as in Example 42 and using 12-amino-8-fluoro-6H-[1]benzothieno[2,3-b][1,5]benzodiazepine.1 hydrochloride (1.5 g), N-n-propylpiperazine (17 g), dimethyl sulfoxide (10 ml) and hydrochloric acid, crude crystals (850 mg) of 8-fluoro-12-(4-propylpiperazin-1-yl)-6H-[1]benzothieno[2,3-b][1,5]benzodiazepine were obtained. The crude crystals were dissolved in ethyl acetate (12 ml) and a solution of 5.5 mol/l hydrochloric acid in ether was added to give 8-fluoro-12-(4-propylpiperazin-1-yl)-6H-[1]benzothieno[2,3-b][1,5]benzodiazepine.2 hydrochloride.1.5 hydrate (757 mg).

melting point 215–217° C. (decomposition). Anal. Calcd. for $C_{22}H_{23}FN_4S \cdot 2HCl \cdot 3/2H_2O$: C, 53.44; H, 5.71; N, 11.33%. Found:C, 53.33; H, 5.78; N, 11.14%.

Example 53

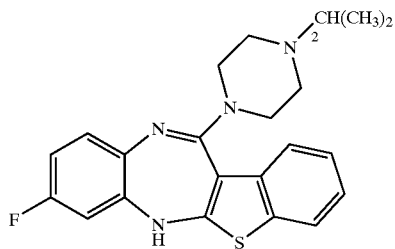

In the same manner as in Example 42 and using 12-amino-8-fluoro-6H-[1]benzothieno[2,3-b][1,5]benzodiazepine.1 hydrochloride (1.5 g), N-isopropylpiperazine (17 g), dimethyl sulfoxide (10 ml) and maleic acid, 8-fluoro-12-(4-isopropylpiperazin-1-yl)-6H-[1]benzothieno[2,3-b][1,5]benzodiazepine.1 maleate (521 mg) was obtained.

melting point 217° C. Anal. Calcd. for $C_{22}H_{23}FN_4S \cdot C_4H_4O_4$: C, 61.16; H, 5.33; N, 10.97%. Found:C, 61.03; H, 5.30; N, 10.91%.

Example 54

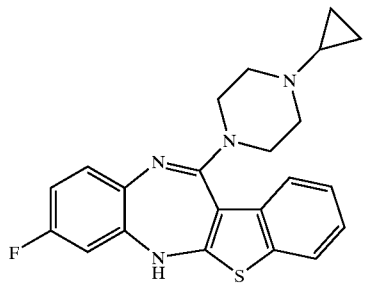

In the same manner as in Example 42 and using 12-amino-8-fluoro-6H-[1]benzothieno[2,3-b][1,5]benzodiazepine.1 hydrochloride (1.7 g), N-cyclopropylpiperazine (8.0 g), dimethyl sulfoxide (10 ml) and maleic acid, 12-(4-cyclopropylpiperazin-1-yl)-8-fluoro-6H-[1]benzothieno[2,3-b][1,5]benzodiazepine.1 maleate (877 mg) was obtained.

melting point 182–183° C. Anal. Calcd. for $C_{22}H_{21}FN_4S \cdot C_4H_4O_4$: C, 61.40; H, 4.95; N, 11.02%. Found:C, 61.28; H, 4.88; N, 10.82%.

Example 55

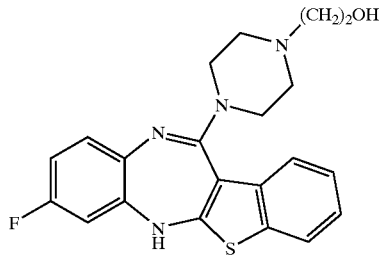

In the same manner as in Example 42 and using 12-amino-8-fluoro-6H-[1]benzothieno[2,3-b][1,5]benzodiazepine.1 hydrochloride (1.3 g), N-(2-hydroxyethyl)

piperazine (12.5 ml), dimethyl sulfoxide (5 ml) and maleic acid, 8-fluoro-12-[4-(2-hydroxyethyl)piperazin-1-yl]-6H-[1]benzothieno[2,3-b][1,5]benzodiazepine.2 maleate.1 hydrate (1.18 g) was obtained.

melting point 75–77° C. Anal. Calcd. for $C_{21}H_{21}FN_4OS.2C_4H_4O_4.H_2O$: C, 53.86; H, 4.83; N, 8.66%. Found:C, 53.80; H, 4.94; N, 8.67%.

Example 56

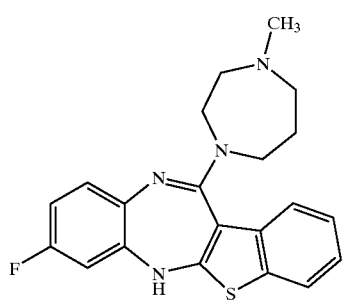

In the same manner as in Example 42 and using 12-amino-8-fluoro-6H-[1]benzothieno[2,3-b][1,5]benzodiazepine.1 hydrochloride (1.4 g), N-methylhomopiperazine (5.4 g), dimethyl sulfoxide (25 ml) and citric acid, 8-fluoro-12-(4-methylhomopiperazin-1-yl)-6H-[1]benzothieno[2,3-b][1,5]benzodiazepine.1 citrate.0.5 hydrate (455 mg) was obtained.

melting point 98–100° C. (decomposition). Anal. Calcd. for $C_{21}H_{21}FN_4S.C_6H_8O_7.1/2H_2O$: C, 55.76; H, 5.20; N, 9.63%. Found:C, 55.48; H, 5.60; N, 9.64%.

Example 57

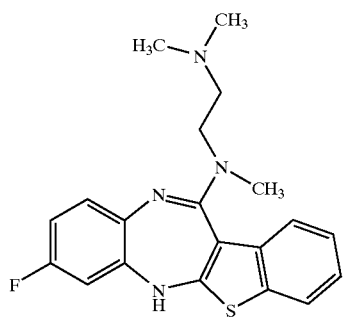

In the same manner as in Example 42 and using 12-amino-8-fluoro-6H-[1]benzothieno[2,3-b][1,5]benzodiazepine.1 hydrochloride (1.3 g), N, N, N'-trimethylethylenediamine (13 g), dimethyl sulfoxide (5 ml) and citric acid, 8-fluoro-12-[N-(2-dimethylaminoethyl)-N-methylamino-]-6H-[1]benzothieno[2,3-b][1,5]benzodiazepine.1 citrate.1 hydrate (289 mg) was obtained.

melting point 72–74° C. (decomposition). Anal. Calcd. for $C_{20}H_{21}FN_4S.C_6H_8O_7.H_2O$: C, 53.97; H, 5.40; N, 9.68%. Found:C, 53.60; H, 5.27; N, 9.02%.

Example 58

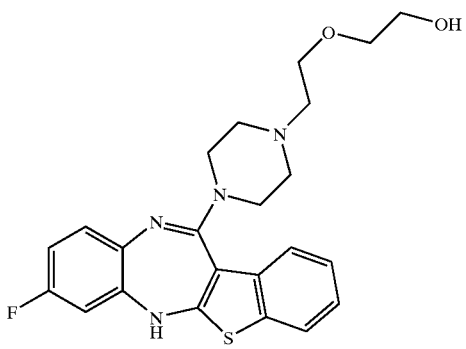

In the same manner as in Example 42 and using 12-amino-8-fluoro-6H-[1]benzothieno[2,3-b][1,5]benzodiazepine.1 hydrochloride (1.6 g), 1-[2-(2-hydroxyethoxy)ethyl]piperazine (13 g) and dimethyl sulfoxide (5 ml), 8-fluoro-12-{4-[2-(2-hydroxyethoxy)ethyl]-1-piperazinyl}-6H-[1]benzothieno[2,3-b][1,5]benzodiazepine (422 mg) was obtained.

melting point 198° C. Anal. Calcd. for $C_{23}H_{25}FN_4O_2S$: C, 62.71; H, 5.72; N, 12.72%. Found:C, 62.63; H, 5.59; N, 12.57%.

Example 59

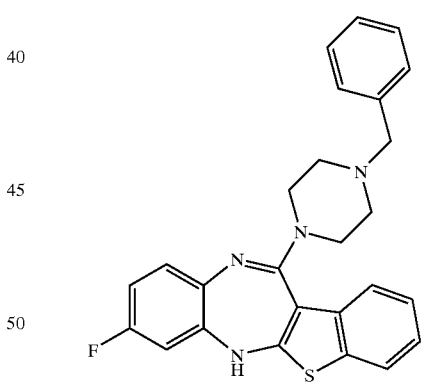

In the same manner as in Example 42 and using 12-amino-8-fluoro-6H-[1]benzothieno[2,3-b][1,5]benzodiazepine.1 hydrochloride (2.1 g), N-benzylpiperazine (25 g), dimethyl sulfoxide (10 ml) and hydrochloric acid, 8-fluoro-12-(4-benzylpiperazin-1-yl)-6H-[1]benzothieno[2,3-b][1,5]benzodiazepine.2 hydrochloride.1/4 hydrate (360 mg) was obtained.

melting point 260–262° C.

Example 60

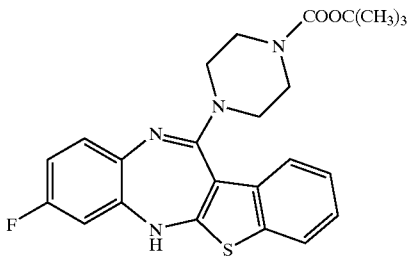

In the same manner as in Example 42 and using 12-amino-8-fluoro-6H-[1]benzothieno[2,3-b][1,5]benzodiazepine.1 hydrochloride (2.0 g), tert-butyl-1-piperazinecarboxylate (5.0 g) and dimethyl sulfoxide (15 ml), 8-fluoro-12-(4-tert-butoxycarbonylpiperazin-1-yl)-6H-[1]benzothieno[2,3-b][1,5]benzodiazepine (1.6 g) was obtained.

$^1$H-NMR(400 MHz, CDCl$_3$) δ: 7.76(d, J=7.8 Hz, 1H), 7.60(d, J=7.8 Hz, 1H), 7.32(dd, J=7.4,7.1 Hz, 1H), 7.22(dd, J=9.2,8.3 Hz, 1H), 6.97(dd, J=8.8,2.9 Hz, 1H), 6.70(dd, J=8.3, 2.8 Hz, 1H), 6.42(dd, J=8.8, 2.9 Hz, 1H), 5.18(br.s, 1H), 4.20–0.70(m, 9H), 1.44(s, 9H).

Example 61

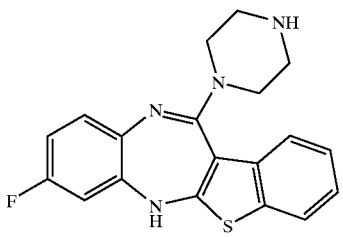

8-Fluoro-12-(4-tert-butoxycarbonylpiperazin-1-yl)-6H-[1]benzothieno[2,3-b][1,5]benzodiazepine (1.6 g) was dissolved in trifluoroacetic acid (8 ml) and the mixture was stirred at room temperature for 3 hours. Trifluoroacetic acid was evaporated under reduced pressure. The residue was dissolved in ethyl acetate and saturated aqueous sodium hydrogencarbonate solution was added. The mixture was stirred at room temperature for 2 hours and the ethyl acetate layer was dried over magnesium sulfate. After natural filtration, the solvent was evaporated and the residue was separated and purified by silica gel column chromatography (chloroform:methanol=4:1) to give 8-fluoro-12-(piperazin-1-yl)-6H-[1]benzothieno[2,3-b][1,5]benzodiazepine (1.7 g), which was treated with maleic acid to give 8-fluoro-12-(piperazin-1-yl)-6H-[1]benzothieno[2,3-b][1,5]benzodiazepine.3/2 maleate.1/2 hydrate (347 mg).

melting point 141–143° C. (decomposition). Anal. Calcd. for C$_{19}$H$_{17}$FN$_4$S.3/2C$_4$H$_4$O$_4$.1/2H$_2$O: C, 56.17; H, 4.34; N, 10.48%. Found:C, 56.30; H, 4.58; N, 10.08%.

Example 62

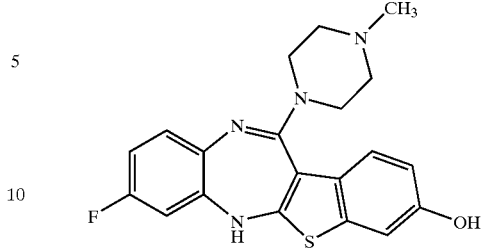

8-Fluoro-3-methoxy-12-(4-methylpiperazin-1-yl)-6H-[1]benzothieno[2,3-b][1,5]benzodiazepine (500 mg) was dissolved in dichloromethane (15 ml) and ethanedithiol (2.10 ml) and aluminium chloride (2.51 g) were added. The mixture was stirred at room temperature for 2 hours. Water (50 ml) was added to the reaction mixture and 10% aqueous sodium hydroxide solution was added until it assumed alkaline. The mixture was extracted with chloroform, washed with water, washed with saturated aqeuous sodium chloride solution and dried over sodium sulfate. The solvent was evaporated under reduced pressure, and the residue was separated by silica gel column chromatography (chloroform:methanol=5:1) and recrystallized from ethyl acetate to give 8-fluoro-3-hydroxy-12-(4-methylpiperazin-1-yl)-6H-[1]benzothieno[2,3-b][1,5]benzodiazepine (251 mg).

$^1$H-NMR(400 MHz, CDCl$_3$) δ: 7.59(d, 1H), 7.01(d, 1H), 6.96(dd, 1H), 6.83(dd, 1H), 6.68(m, 1H), 6.41(dd, 1H), 5.09(br.s, 1H), 4.00–2.00(m, 8H), 2.34(s, 3H).

Example 63

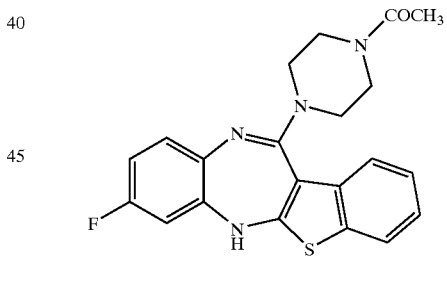

8-Fluoro-12-(piperazin-1-yl)-6H-[1]benzothieno[2,3-b][1,5]benzodiazepine (260 mg) was dissolved in toluene (5 ml) and anhydrous acetic acid (230 mg) and triethylamine (375 mg) were added. The mixture was stirred at 80° C. for 30 minutes. The reaction mixture was allowed to cool to room temperature, and extracted with chloroform, washed with water and dried over anhydrous magnesium sulfate. After natural filtration, the solvent was evaporated under reduced pressure and the residue was recrystallized from methanol to give 8-fluoro-12-(4-acetylpiperazin-1-yl)-6H-[1]benzothieno[2,3-b][1,5]benzodiazepine.1/4 hydrate (97 mg).

melting point >290° C. Anal. Calcd. for C$_{21}$H$_{19}$FN$_4$OS.1/4H$_2$O: C, 63.22; H, 4.93; N, 14.04%. Found:C, 62.97; H, 4.67; N, 13.75%.

Example 64

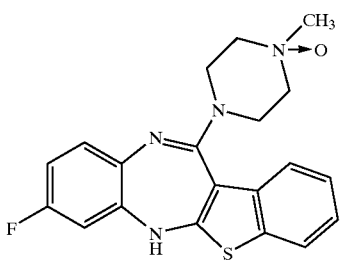

To a solution of 8-fluoro-12-(4-methylpiperazin-1-yl)-6H-[1]benzothieno[2,3-b][1,5]benzodiazepine (100 mg) in ethanol (2 ml) was added 30% aqueous hydrogen peroxide solution (0.1 ml) and the mixture was stirred at room temperature for 3 hours and then left standing for one day. The obtained suspension was filtered and the solvent was evaporated under reduced pressure. The obtained residue was purified by silica gel column chromatography (chloroform:methanol=5:1) to give 8-fluoro-12-(4-methylpiperazine-4-oxide-1-yl)-6H-[1]benzothieno[2,3-b][1,5]benzodiazepine (50 mg) as a yellow oily substance.

$^1$H-NMR(400 MHz, CDCl$_3$) δ: 3.00–3.80(8H, m, CH$_2$× 4), 3.25(3H, s, CH$_3$), 6.46(1H, dd, J=2.9, 8.8 Hz, ArH), 6.74(1H, ddd, J=2.4, 2.9, 8.3 Hz, ArH), 6.97(1H, dd, J=2.9, 8.8 Hz, ArH), 7.24(1H, d, J=7.4 Hz, ArH), 7.37(1H, dd, J=7.3, 7.8 Hz, ArH), 7.63(1H, d, J=8.3 Hz, ArH), 7.72(1H, d, J=8.3 Hz, ArH). MS: m/e 383(M+1).

Example 65

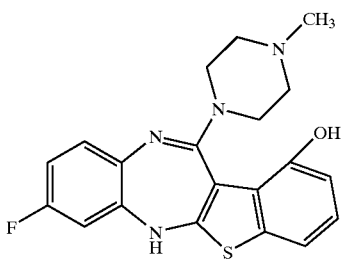

In the same manner as in Example 62 and using 8-fluoro-1-methoxy-12-(4-methylpiperazin-1-yl)-6H-[1]benzothieno[2,3-b][1,5]benzodiazepine, dichloromethane, ethanedithiol and aluminium chloride, 8-fluoro-1-hydroxy-12-(4-methylpiperazin-1-yl)-6H-[1]benzothieno[2,3-b][1,5]benzodiazepine is obtained.

Example 66

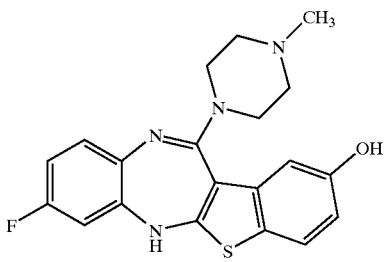

In the same manner as in Example 62 and using 8-fluoro-2-methoxy-12-(4-methylpiperazin-1-yl)-6H-[1]benzothieno[2,3-b][1,5]benzodiazepine, dichloromethane, ethanedithiol and aluminium chloride, 8-fluoro-2-hydroxy-12-(4-methylpiperazin-1-yl)-6H-[1]benzothieno[2,3-b][1,5]benzodiazepine is obtained.

Example 67

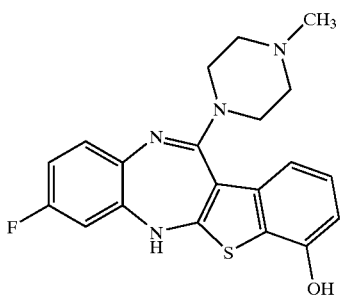

In the same manner as in Example 62 and using 8-fluoro-4-methoxy-12-(4-methylpiperazin-1-yl)-6H-[1]benzothieno[2,3-b][1,5]benzodiazepine, dichloromethane, ethanedithiol and aluminium chloride, 8-fluoro-4-hydroxy-12-(4-methylpiperazin-1-yl)-6H-[1]benzothieno[2,3-b][1,5]benzodiazepine is obtained.

Example 68

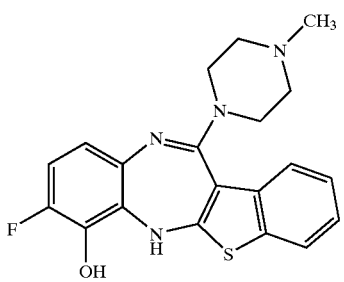

In the same manner as in Example 62 and using 8-fluoro-7-methoxy-12-(4-methylpiperazin-1-yl)-6H-[1]benzothieno[2,3-b][1,5]benzodiazepine, dichloromethane, ethanedithiol and aluminium chloride, 8-fluoro-7-hydroxy-12-(4-methylpiperazin-1-yl)-6H-[1]benzothieno[2,3-b][1,5]benzodiazepine is obtained.

Example 69

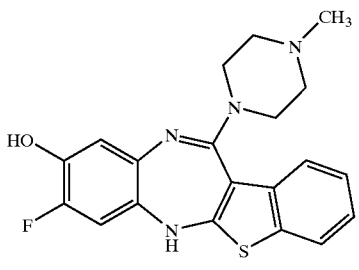

In the same manner as in Example 62 and using 8-fluoro-9-methoxy-12-(4-methylpiperazin-1-yl)-6H-[1]benzothieno[2,3-b][1,5]benzodiazepine, dichloromethane, ethanedithiol and aluminium chloride, 8-fluoro-9-hydroxy-12-(4-methylpiperazin-1-yl)-6H-[1]benzothieno[2,3-b][1,5]benzodiazepine is obtained.

Example 70

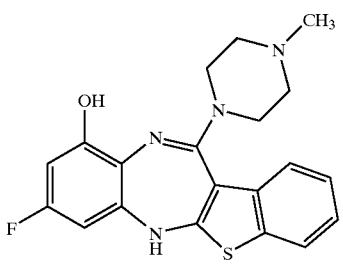

In the same manner as in Example 62 and using 8-fluoro-10-methoxy-12-(4-methylpiperazin-1-yl)-6H-[1]benzothieno[2,3-b][1,5]benzodiazepine, dichloromethane, ethanedithiol and aluminium chloride, 8-fluoro-10-hydroxy-12-(4-methylpiperazin-1-yl)-6H-[1]benzothieno[2,3-b][1,5]benzodiazepine is obtained.

Example 71

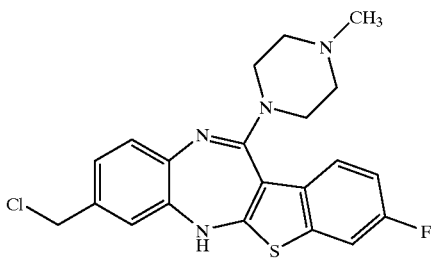

3-Fluoro-8-methyl-12-(4-methylpiperazin-1-yl)-6H-[1]benzothieno[2,3-b][1,5]benzodiazepine is dissolved in carbon tetrachloride and reacted with 2,2'-azobis(isobutylonitrile) in the presence of N-chlorosuccinimide to give 8-chloromethyl- 3-fluoro-12-(4-methylpiperazin-1-yl)-6H-[1]benzothieno[2,3-b][1,5]benzodiazepine.

Example 72

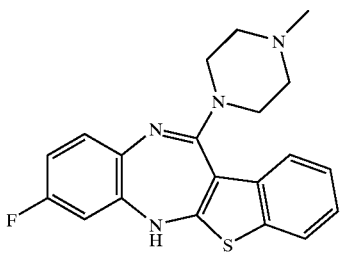

12-Amino-8-fluoro-6H-[1]benzothieno[2,3-b][1,5]benzodiazepine hydrochloride (102 g) was suspended in toluene (600 ml), and the mixture was stirred under reflux with heating for 3 hours to remove water. The mixture was cooled to 70° C. under a nitrogen atmosphere, and N-methylpiperazine (300 ml) was added. The mixture was stirred with heating under a nitrogen atmosphere until the inside temperature reached 120° C. while removing toluene for 1.5 hours. The mixture was heated under a nitrogen atmosphere at 120° C. for 2.5 hours and cooled to 25° C. under a nitrogen atmosphere. Ethyl acetate (600 ml) and water (450 ml) were added to the reaction mixture for extraction and the obtained ethyl acetate layer was washed three times with water (300 ml). After confirming pH 7–8 of washing water, the solvent was concentrated under reduced pressure. Acetonitrile (100 ml) was added and the mixture was azeotropically concentrated to dryness under reduced pressure. To the residue was added acetonitrile (300 ml) and the mixture was heated for dissolution. The solution was cooled and stirred at −10° C.—−5° C. for 2.5 hours to allow precipitation of crystals. The precipitated crystals were filtered by suction and washed with acetonitrile (100 ml), followed by drying to give 8-fluoro-12-(4-methylpiperazin-1-yl)-6H-[1]benzothieno[2,3-b][1,5]benzodiazepine (65.5 g).

melting point 167–169° C.

Example 73

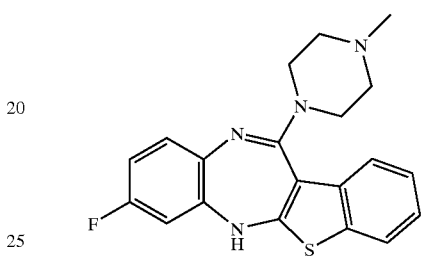

Using an equivalent amount of hydrochloric acid instead of maleic acid in Example 2,8-fluoro-12-(4-methylpiperazin-1-yl)-6H-[1]benzothieno[2,3-b][1,5]benzodiazepine.1 hydrochloride was obtained.

melting point 310.3° C. MS:m/e 366, Anal. Calcd. for $C_{20}H_{19}FN_4$ S.HCl: C, 59.62; H, 5.00; N, 13.91%. Found:C, 59.43; H, 5.02; N, 13.88%.

STARTING MATERIAL SYNTHESIS EXAMPLE 60

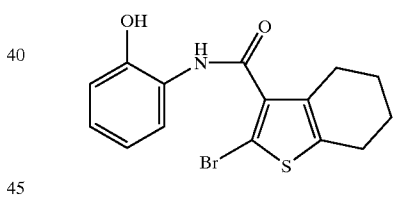

2-Bromo-4,5,6,7-tetrahydrobenzo[b]thiophene-3-carboxylic acid (6 g) was suspended in thionyl chloride (30 ml) and the mixture was stirred under reflux with heating for 75 minutes. Thionyl chloride was evaporated under reduced pressure and the residue was dissolved in toluene (50 ml). This toluene solution was added dropwise to a solution of 2-aminophenol (2.5 g) in pyridine (50 ml) under ice-cooling. The mixture was stirred at room temperature for 2 hours and completion of the reaction was confirmed by thin layer chromatography. The solvent was evaporated under reduced pressure and the residue was dissolved in ethyl acetate. The mixture was washed with diluted hydrochloric acid and saturated aqueous sodium hydrogencarbonate solution and dried over magnesium sulfate. The solvent was evaporated under reduced pressure. To the residue was added diisopropyl ether and the mixture was filtrated to give 2-bromo-4,5,6,7-tetrahydro-N-(2-hydroxyphenyl)-benzo[b]thiophene-3-carboxamide (5.3 g).

$^1$H-NMR(400 MHz, CDCl$_3$) δ: 8.65(br, 1H), 7.94(br, 1H), 7.15–7.19(m, 2H), 7.06(d, J=8.3 Hz, 1H), 6.91(m, 1H), 2.75–2.78(m, 2H), 2.67–2.70(m, 2H), 1.77–1.86(m, 4H)

STARTING MATERIAL SYNTHESIS EXAMPLE 61

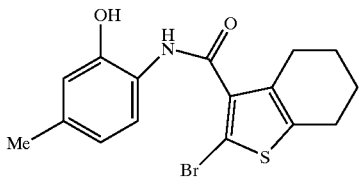

In the same manner as in Starting Material Synthesis Example 60 and using 2-bromo-4,5,6,7-tetrahydrobenzo[b]thiophene-3-carboxylic acid (6 g), thionyl chloride (30 ml), 2-amino-5-methylphenol (3.14 g), 2-bromo-4,5,6,7-tetrahydro-N-(2-hydroxy-4-methylphenyl)-benzo[b]thiophene-3-carboxamide (5.8 g) was obtained.

$^1$H-NMR(400 MHz, DMSO-d$_6$) δ: 9.66(s, 1H), 9.33(br, 1H), 7.62(d, J=8.3 Hz, 1H), 6.71(s, 1H), 6.62(d, J=8.3 Hz, 1H), 2.66–2.50(m, 4H), 2.22(s, 3H), 1.76–1.72(m, 4H)

STARTING MATERIAL SYNTHESIS EXAMPLE 62

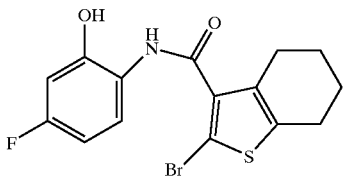

In the same manner as in Starting Material Synthesis Example 60 and using 2-bromo-4,5,6,7-tetrahydrobenzo[b]thiophene-3-carboxylic acid, thionyl chloride and 2-amino-5-fluorophenol, 2-bromo-4,5,6,7-tetrahydro-N-(4-fluoro-2-hydroxyphenyl)-benzo[b]thiophene-3-carboxamide is obtained.

STARTING MATERIAL SYNTHESIS EXAMPLE 63

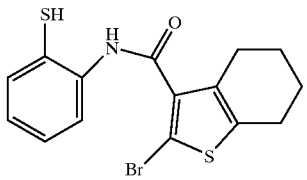

In the same manner as in Starting Material Synthesis Example 60 and using 2-bromo-4,5,6,7-tetrahydrobenzo[b]thiophene-3-carboxylic acid, thionyl chloride, 2-aminothiophenol, 2-bromo-4,5,6,7-tetrahydro-N-(2-mercaptophenyl)-benzo[b]thiophene-3-carboxamide is obtained.

STARTING MATERIAL SYNTHESIS EXAMPLE 64

In the same manner as in Starting Material Synthesis Example 60 and using 2-bromo-4,5,6,7-tetrahydrobenzo[b]thiophene-3-carboxylic acid, thionyl chloride and 2-amino-5-methylthiophenol, 2-bromo-4,5,6,7-tetrahydro-N-(2-mercapto-4-methylphenyl)-benzo[b]thiophene-3-carboxamide is obtained.

STARTING MATERIAL SYNTHESIS EXAMPLE 65

In the same manner as in Starting Material Synthesis Example 60 and using 2-bromo-4,5,6,7-tetrahydrobenzo[b]thiophene-3-carboxylic acid, thionyl chloride, 2-amino-5-fluorothiophenol, 2-bromo-4,5,6,7-tetrahydro-N-(4-fluoro-2-mercaptophenyl)-benzo[b]thiophene-3-carboxamide

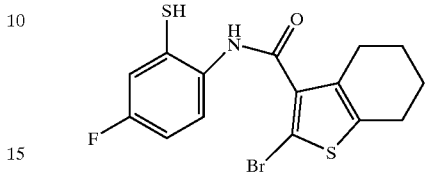

is obtained.

Example 74

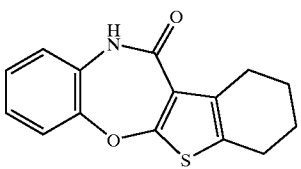

To a solution of 2-bromo-4,5,6,7-tetrahydro-N-(2-hydroxyphenyl)-benzo[b]thiophene-3-carboxamide (5.3 g) in dimethyl sulfoxide (50 ml) was added potassium carbonate (4.2 g) and the mixture was stirred at 140° C. for 4 hours. The completion of the reaction was confirmed by thin layer chromatography. The mixture was cooled to room temperature and the reaction mixture was poured into water (300 ml). After neutraition with hydrochloric acid, the mixture was extracted twice with chloroform and washed with saturated brine. The organic layer was dried over magnesium sulfate and the solvent was evaporated under reduced pressure. The residue was purified by silica gel column chromatography (chloroform) to give 1,2,3,4-tetrahydro-[1]benzothieno[2,3-b][1,5]benzoxazepin-12(11H)-one (2.1 g).

$^1$H-NMR(400 MHz, DMSO-d$_6$) δ: 7.81(br, 1H), 7.10–7.17(m, 3H), 6.98(d, J=8.3 Hz, 1H), 2.75–2.78(m, 2H), 2.58–2.61(m, 2H), 1.73–1.83(m, 4H).

Example 75

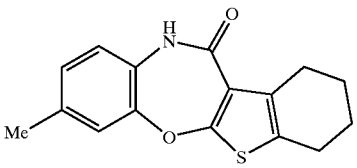

In the same manner as in Example 18 and using 2-bromo-4,5,6,7-tetrahydro-N-(2-hydroxy4-methylphenyl)-benzo[b]thiophene-3-carboxamide (5.8 g), dimethyl sufoxide (80 ml) and potassium carbonate (4.7 g), 1,2,3,4-tetrahydro-8-methyl[1]benzothieno[2,3-b][1,5]benzoxazepin-12(11H)-one (1.87 g) was obtained.

$^1$H-NMR(400 MHz, DMSO-d$_6$) δ: 10.03(s, 1H), 7.03–6.99(m, 3H), 2.62–2.56(m, 4H), 2.25(s, 3H), 1.73–1.67(m, 4H)

Example 76

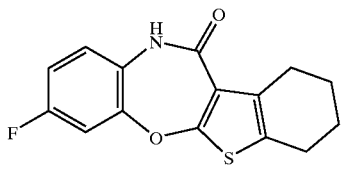

In the same manner as in Example 74 and using 2-bromo-4,5,6,7-tetrahydro-N-(4-fluoro-2-hydroxyphenyl)-benzo[b]thiophene-3-carboxamide, dimethyl sulfoxide and potassium carbonate, 8-fluoro-1,2,3,4-tetrahydro-[1]benzothieno[2,3-b][1,5]benzoxazepin-12(11H)-one is obtained.

Example 77

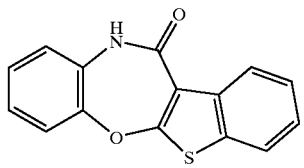

1,2,3,4-Tetrahydro-[1]benzothieno[2,3-b][1,5]benzoxazepin-12(11H)-one (1.5 g) and dichlorodicyano-p-benzoquinone (2.6 g) was dissolved in benzene (45 ml) and the mixture was stirred under reflux with heating for 12 hours. The reaction mixture was evaporated under reduced pressure to remove the solvent, and the residue was added to a mixture of chloroform/water. The organic layer was washed with water and dried over magnesium sulfate. The solvent was evaporated under reduced pressure and the residue was purified by silica gel column chromatography (chloroform) to give [1]benzothieno[2,3-b][1,5]benzoxazepin-12(11H)-one (1.25 g).

melting point 240–242° C.

Example 78

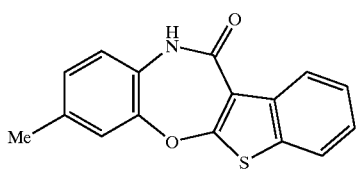

In the same manner as in Example 77 and using 1,2,3,4-tetrahydro-8-methyl-[1]benzothieno[2,3-b][1,5]benzoxazepin-12(11H)-one (1.87 g), dichlorodicyano-p-benzoquinone (3.1 g) and benzene (55 ml), 8-methyl-[1]benzothieno[2,3-b][1,5]benzoxazepin-12(11H)-one (1.5 g) was obtained.

$^1$H-NMR(400 MHz, DMSO-$d_6$) δ: 10.26(s, 1H), 8.25(d, J=8.3 Hz, 1H), 7.89(d, J=7.8 Hz, 1H), 7.43–7.38(m, 2H), 7.14–7.06(m, 2H), 7.10(s, 1H), 2.09(s, 3H)

Example 79

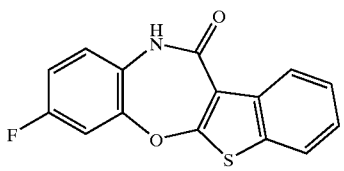

In the same manner as in Example 77 and using 8-fluoro-1,2,3,4-tetrahydro-[1]benzothieno[2,3-b][1,5]benzoxazepin-12(11H)-one, dichlorodicyano-p-benzoquinone and benzene, 8-fluoro-[1]benzothieno[2,3-b][1,5]benzoxazepin-12(11H)-one is obtained.

Example 80

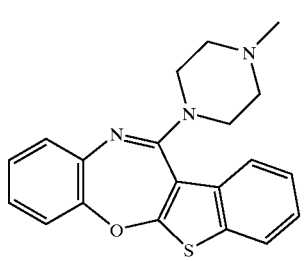

[1]Benzothieno[2,3-b][1,5]benzoxazepin-12(11H)-one (0.7 g) was suspended in phosphorus oxychloride (5 ml) and N,N-dimethylaniline (0.17 ml) was added. The mixture was stirred under reflux with heating for 1 hour. The solvent was evaporated azeotropically with toluene under reduced pressure, and to the residue was added 1-methylpiperazine (10 ml) under ice-cooling, and the mixture was stirred under reflux with heating for 40 minutes. The reaction mixture was cooled to room temperature and the solvent was evaporated under reduced pressure. To the residue was added chloroform and the mixture was washed with water and saturated brine and dried over magnesium sulfate. The solvent was evaporated under reduced pressure and the residue was purified by silica gel column chromatography (chloroform:methanol=100:1). The obtained oily substance was dissolved in ethyl acetate, and a solution of fumaric acid (135 mg) in ethanol was added. The obtained crystals were recrystallized from ethyl acetate/ethanol to give 12-(4-methylpiperazin-1-yl)-[1]benzothieno[2,3-b][1,5]benzoxazepin-1/2 fumarate (264 mg).

melting point 240–242° C.

Example 81

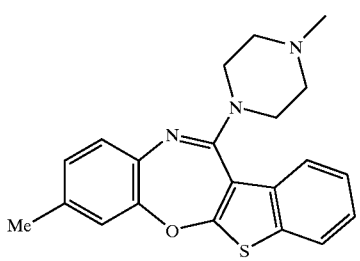

In the same manner as in Example 80 and using 8-methyl-[1]benzothieno[2,3-b][1,5]benzoxazepin-12(11H)-one (1.5 g), phosphorus oxychloride (15.3 ml), N,N-dimethylaniline (380 mg), 1-methylpiperazine (25 ml) and fumaric acid (176 mg), 8-methyl-12-(4-methylpiperazin-1-yl)-[1]benzothieno[2,3-b][1,5]benzoxazepin-1/2 fumarate 1/4 hydrate (221 mg) was obtained.

melting point 140–141° C. (ethanol/water).

Example 82

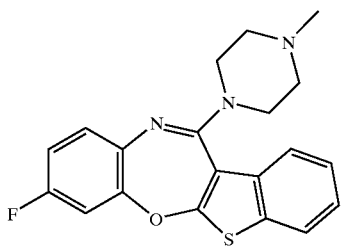

In the same manner as in Example 80 and using 8-fluoro-[1]benzothieno[2,3-b][1,5]benzoxazepin-12(11H)-one, phosphorus oxychloride, N,N-dimethylaniline and 1-methylpiperazine, 8-fluoro-12-(4-methylpiperazin-1-yl)-[1]benzothieno[2,3-b][1,5]benzoxazepine is obtained.

Example 83

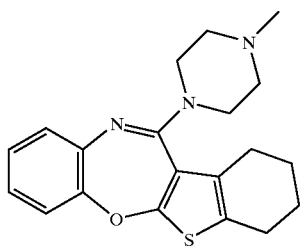

In the same manner as in Example 80 and using 1,2,3,4-tetrahydro-[1]benzothieno[2,3-b][1,5]benzoxazepin-12(11H)-one (0.6 g), phosphorus oxychloride (5 ml), N,N-dimethylaniline (0.14 ml), 1-methylpiperazine (10 ml) and fumaric acid (260 mg), 1,2,3,4-tetrahydro-12-(4-methylpiperazin-1-yl)-[1]benzothieno[2,3-b][1,5]benzoxazepine.fumarate (575 mg) was obtained.

melting point 247–249° C. (ethanol/water).

Example 84

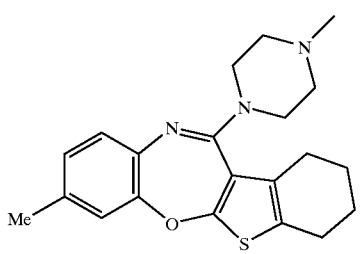

In the same manner as in Example 80 and using 1,2,3,4-tetrahydro-8-methyl-[1]benzothieno[2,3-b][1,5]benzoxazepin-12(11H)-one, phosphorus oxychloride, N,N-dimethylaniline and 1-methylpiperazine, 1,2,3,4-tetrahydro-8-methyl-12-(4-methylpiperazin-1-yl)-[1]benzothieno[2,3-b][1,5]benzoxazepine is obtained.

Example 85

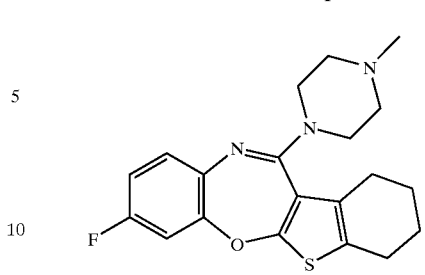

In the same manner as in Example 80 and using 8-fluoro-1,2,3,4-tetrahydro-[1]benzothieno[2,3-b][1,5]benzoxazepin-12(11H)-one, phosphorus oxychloride, N,N-dimethylaniline and 1-methylpiperazine, 8-fluoro-1,2,3,4-tetrahydro-12-(4-methylpiperazin-1-yl)-[1]benzothieno[2,3-b][1,5]benzoxazepine is obtained.

STARTING MATERIAL SYNTHESIS EXAMPLE 66

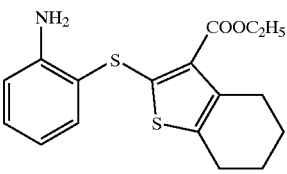

2-Aminobenzenethiol (1.1 g) was dissolved in N,N-dimethylformamide (25 ml) and 60% sodium hydride (360 mg) was added. The mixture was stirred at room temperature for 20 minutes. To the mixture was added ethyl 2-bromo-4,5,6,7-tetrahydrobenzo[b]thiophene-3-carboxylate (2.6 g), and the mixture was stirred at 140° C. for 1.5 hours and allowed to cool to room temperature. The reaction mixture was extracted with ethyl acetate (300 ml), washed with water (200 ml) and dried over anhydrous sodium sulfate. The solvent was evaporated under reduced pressure and the obtained crude crystals were washed with isopropyl ether and filtrated to give ethyl 2-(2-aminobenzenethio)-4,5,6,7-tetrahydrobenzo[b]thiophene-3-carboxylate (1.4 g).

$^1$H-NMR(400 MHz, CDCl$_3$) δ: 7.50(d, J=7.4 Hz, 1H), 7.28(m, 1H), 6.80(m, 2H), 4.43(br.s, 2H), 4.38(q, J=7.3 Hz, 2H), 2.78(m, 2H), 2.52(m, 2H), 1.73–1.60(m, 4H), 1.41(t, 3H)

Example 86

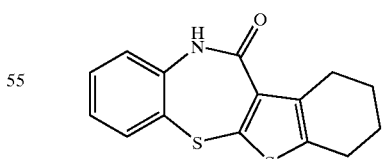

Ethyl 2-(2-aminobenzenethio)-4,5,6,7-tetrahydrobenzo[b]thiophene-3-carboxylate (1.4 g) was dissolved in N,N-dimethylformamide (20 ml) and 60% sodium hydride (170 mg) was added. The mixture was stirred at 80° C. for 1.5 hours and 110° C. for 45 minutes. The reaction mixture was allowed to cool and poured into water (300 ml), followed by acidification with 35% hydrochloric acid. Filtration of precipitated crystals gave 1,2,3,4-tetrahydro[1]benzothieno[2,3-b][1,5]benzothiazepin-12(11H)-one (1.3 g).

¹H-NMR(400 MHz, CDCl₃) δ: 8.54(br.s, 1H), 7.79(d, 1H), 7.64–7.45(m, 3H), 3.27–2.82(m, 4H), 2.36–1.57(m, 4H)

Alternatively, in the same manner as in Example 18 and using 2-bromo-4,5,6,7-tetrahydro-N-(2-mercaptophenyl)-benzo[b]thiophene-3-carboxamide, dimethyl sulfoxide and potassium carbonate, 1,2,3,4-tetrahydro[1]benzothieno[2,3-b][1,5]benzothiazepin-12(11H)-one is obtained.

Example 87

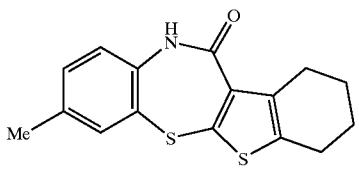

In the same manner as in Example 18 and using 2-bromo-4,5,6,7-tetrahydro-N-(2-mercapto-4-methylphenyl)-benzo[b]thiophene-3-carboxamide, dimethyl sulfoxide and potassium carbonate, 1,2,3,4-tetrahydro-8-methyl-[1]benzothieno[2,3-b][1,5]benzothiazepin-12(11H)-one (1.87 g) is obtained.

Example 88

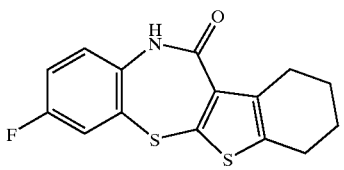

In the same manner as in Example 74 and using 2-bromo-4,5,6,7-tetrahydro-N-(4-fluoro-2-mercaptophenyl)-benzo[b]thiophene-3-carboxamide, dimethyl sufoxide and potassium carbonate, 8-fluoro-1,2,3,4-tetrahydro-[1]benzothieno[2,3-b][1,5]benzothiazepin-12(11H)-one is obtained.

Example 89

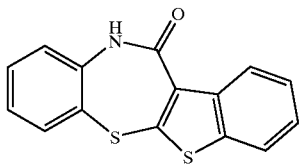

In the same manner as in Example 77 and using 1,2,3,4-tetrahydro[1]benzothieno[2,3-b][1,5]benzothiazepin-12(11H)-one (1.2 g), dichlorodicyano-p-benzoquinone (2.1 g) and toluene (20 ml), [1]benzothieno[2,3-b][1,5]benzothiazepin-12(11H)-one (500 mg) was obtained.

¹H-NMR(400 MHz, DMSO-d₆) δ: 10.77(br.s, 1H), 8.10 (d, J=8.3 Hz, 1H), 7.96(d, J=6.4 Hz, 1H), 7.56(d, J=8.4 Hz, 1H), 7.42(m, 3H), 7.31(d, J=8.4 Hz, 1H), 7.19(dd, J=7.4, 7.8 Hz, 1H)

Example 90

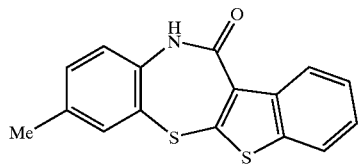

In the same manner as in Example 77 and using 1,2,3,4-tetrahydro-8-methyl-[1]benzothieno[2,3-b][1,5]benzothiazepin-12(11H)-one, dichlorodicyano-p-benzoquinone and benzene, 8-methyl-[1]benzothieno[2,3-b][1,5]benzothiazepin-12(11H)-one is obtained.

Example 91

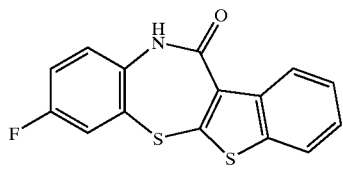

In the same manner as in Example 77 and using 8-fluoro-1,2,3,4-tetrahydro-[1]benzothieno[2,3-b][1,5]benzothiazepin-12(11H)-one, dichlorodicyano-p-benzoquinone and benzene, 8-fluoro-[1]benzothieno[2,3-b][1,5]benzothiazepin-12(11H)-one is obtained.

Example 92

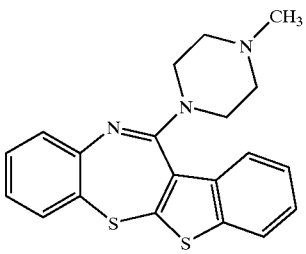

In the same manner as in Example 80 and using [1]benzothieno[2,3-b][1,5]benzothiazepin-12(11H)-one (500 mg), phosphorus oxychloride (6.3 g), N,N-dimethylaniline (109 mg) and 1-methylpiperazine (5 ml), 12-(4-methylpiperazin-1-yl)-[1]benzothieno[2,3-b][1,5]benzothiazepine (278 mg) was obtained.

¹H-NMR(400 MHz, CDCl₃) δ: 7.87(d, J=7.8 Hz, 1H), 7.70(d, J=7.8 Hz, 1H), 7.38–7.29(m, 3H), 7.20(dd, J=7.3, 7.8 Hz, 1H), 7.07(d, J=8.3 Hz, 1H), 6.91(dd, J=8.3, 8.5 Hz, 1H), 4.11–3.84(m, 2H), 3.24–3.06(m, 2H), 2.76(m, 1H), 2.50–2.30(m, 3H), 2.33(s, 3H).

Example 93

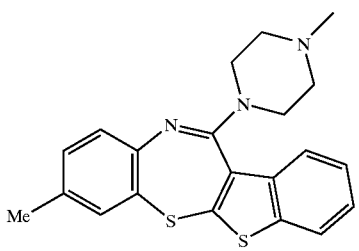

In the same manner as in Example 80 and using 8-methyl-[1]benzothieno[2,3-b][1,5]benzothiazepin-12(11H)-one, phosphorus oxychloride, N,N-dimethylanilne, 1-methylpiperazine, 8-methyl-12-(4-methylpiperazin-1-yl)-[1]benzothieno[2,3-b][1,5]benzothiazepine is obtained.

Example 94

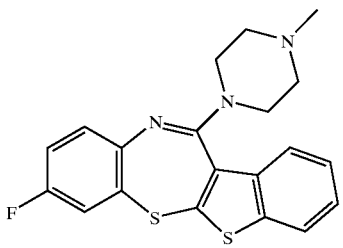

In the same manner as in Example 80 and using 8-fluoro-[1]benzothieno[2,3-b][1,5]benzothiazepin-12(11H)-one, phosphorus oxychloride, N,N-dimethylaniline and 1-methylpiperazine, 8-fluoro-12-(4-methylpiperazin-1-yl)-[1]benzothieno[2,3-b][1,5]benzothiazepine is obtained.

Example 95

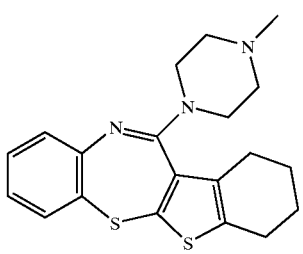

In the same manner as in Example 80 and using 1,2,3,4-tetrahydro-[1]benzothieno[2,3-b][1,5]benzothiazepin-12(11H)-one, phosphorus oxychloride, N,N-dimethylaniline and 1-methylpiperazine, 1,2,3,4-tetrahydro-12-(4-methylpiperazin-1-yl)-[1]benzothieno[2,3-b][1,5]benzothiazepine is obtained.

Example 96

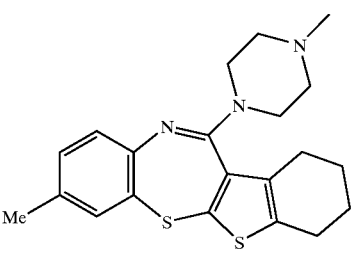

In the same manner as in Example 80 and using 1,2,3,4-tetrahydro-8-methyl-[1]benzothieno[2,3-b][1,5]benzothiazepin-12(11H)-one, phosphorus oxychloride, N,N-dimethylaniline and 1-methylpiperazine, 1,2,3,4-tetrahydro-8-methyl-12-(4-methylpiperazin-1-yl)-[1]benzothieno[2,3-b][1,5]benzothiazepine is obtained.

Example 97

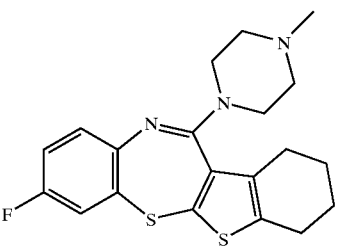

In the same manner as in Example 80 and using 8-fluoro-1,2,3,4-tetrahydro-[1]benzothieno[2,3-b][1,5]benzothiazepin-12(11H)-one, phosphorus oxychloride, N,N-dimethylaniline and 1-methylpiperazine, 8-fluoro-1,2,3,4-tetrahydro-12-(4-methylpiperazin-1-yl)-[1]benzothieno[2,3-b][1,5]benzothiazepine is obtained.

STARTING MATERIAL SYNTHESIS EXAMPLE 67

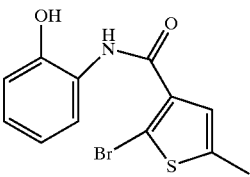

2-Bromo-5-methyl-3-thiophenecarboxylic acid (5 g) was suspended in thionyl chloride (20 ml) and the mixture was stirred under reflux with heating for 75 minutes. Thionyl chloride was evaporated under reduced pressure and the residue was dissolved in toluene (5 ml). This toluene solution was added dropwise to a solution of 2-aminophenol (3.7 g) in pyridine (30 ml) at 0° C. The mixture was stirred at room temperature for 6 hours and the solvent was evaporated under reduced pressure. The residue was dissolved in ethyl acetate. This solution was washed with diluted hydrochloric acid and saturated aqueous sodium hydrogencarbonate solution and dried over sodium sulfate. The solvent was evaporated under reduced pressure and to the residue was added diisopropyl ether. The precipitated crystals were collected by filtration and washed with hexane to give N-(2- hydroxyphenyl)-2-bromo-5-methyl-3-thiophenecarboxamide (5.5 g).

¹H-NMR(400 MHz, CDCl₃) δ: 2.45(3H, s, CH₃), 6.92 (1H, t, ArH), 7.06(1H, d, ArH), 7.16(3H, m, ArH, H of thiophene ring), 8.53, 8.63(1H, 1H, br, br, NH, OH)

STARTING MATERIAL SYNTHESIS EXAMPLE 68

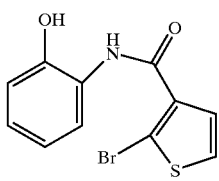

2-Bromo-3-thiophenecarboxylic acid (30 g) was suspended in thionyl chloride (35 ml) and the mixture was stirred under reflux with heating for 1 hour. Thionyl chloride was evaporated under reduced pressure and the residue was dissolved in toluene (10 ml). This toluene solution was added dropwise to a solution of 2-aminophenol (19 g) in pyridine (100 ml) at 0° C. The mixture was stirred at room temperature for 20 minutes and the solvent was evaporated under reduced pressure. The residue was dissolved in ethyl acetate. This solution was washed with diluted hydrochloric acid and saturated aqueous sodium hydrogencarbonate solution, and the precipitated crystals were collected by filtration to give N-(2-hydroxyphenyl)-5-bromo-3-thiophenecarboxamide (21 g). The filtrate was concentrated and the precipitated crystals were collected by filtration to give N-(2-hydroxyphenyl)-2-bromo-3-thiophenecarboxamide (10 g).

¹H-NMR(400 MHz, DMSO-d₆) δ6.82(1H, t, J=7.8 Hz, ArH), 6.91(1H, d, J=8.3 Hz, ArH), 7.00(1H, t, J=7.8 Hz, ArH), 7.40(1H, d, J=5.3 Hz, H of thiophene ring), 7.68(1H, d, J=5.9 Hz, H of thiophene ring), 7.81(1H, d, J=7.8 Hz, ArH), 9.30(1H, br, NH or OH), 9.87(1H, br, NH or OH)

STARTING MATERIAL SYNTHESIS EXAMPLE 69

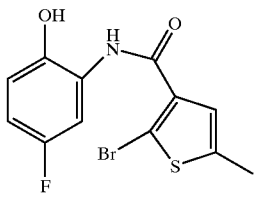

2-Bromo-5-methyl-3-thiophenecarboxylic acid (3 g) was suspended in thionyl chloride (15 ml) and the mixture was stirred under reflux with heating for 40 minutes. Thionyl chloride was evaporated under reduced pressure and the residue was dissolved in toluene (5 ml). This toluene solution was added dropwise to a solution of 2-amino-4-fluorophenol (1.7 g) in pyridine (20 ml) at 0° C. The mixture was stirred at room temperature for 1.5 hours and the solvent was evaporated under reduced pressure. To the residue was added water-ethyl acetate. The precipitated crystals were collected by filtration to give N-(3-fluoro-6-hydroxyphenyl)-2-bromo-5-methyl-3-thiophenecarboxamide (2.1 g). The filtrate was extracted three times with ethyl acetate and the obtained organic layer was washed with water. The organic layer was dried over sodium sulfate and the solvent was evaporated under reduced pressure. To the residue was added ethyl acetate and the precipitated crystals were collected by filtration to give N-(3-fluoro-6-hydroxyphenyl)-2-bromo-5-methyl-3-thiophenecarboxamide (1.3 g). melting point 210–212° C.

STARTING MATERIAL SYNTHESIS EXAMPLE 70

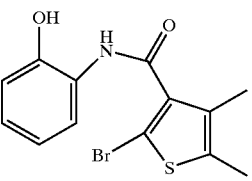

2-Bromo-4,5-dimethyl-3-thiophenecarboxylic acid (2.9 g) was suspended in thionyl chloride (15 ml) and the mixture was stirred under reflux with heating for 65 minutes. Thionyl chloride was evaporated under reduced pressure and the residue was dissolved in toluene (25 ml). This toluene solution was added dropwise to a solution of 2-aminophenol (1.5 g) in pyridine (30 ml) at 0° C. The mixture was stirred at room temperature for 1.5 hours and the solvent was evaporated under reduced pressure. To the residue was added ethyl acetate and the mixture was washed with diluted hydrochloric acid, and water and saturated brine. The organic layer was dried over magnesium sulfate and the solvent was evaporated under reduced pressure. To the residue was added diisopropyl ether and the precipitated crystals were collected by filtration to give N-(2-hydroxyphenyl)-2-bromo-4,5-dimethyl-3-thiophenecarboxamide (3.3 g).

¹H-NMR(400 MHz, CD₃OD) δ2.20(3H, s, CH₃), 2.33 (3H, s, CH₃), 6.90(2H, m, ArH), 7.03(1H, m, ArH), 7.87(1H, m, ArH)

STARTING MATERIAL SYNTHESIS EXAMPLE 71

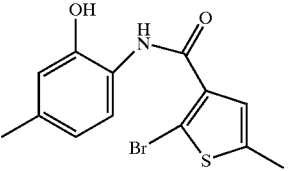

2-Bromo-5-methyl-3-thiophenecarboxylic acid (3 g) was suspended in thionyl chloride (15 ml) and the mixture was stirred under reflux with heating for 70 minutes. Thionyl chloride was evaporated under reduced pressure and the residue was dissolved in toluene (20 ml). This toluene solution was added dropwise to a solution of 2-amino-5-methylphenol (1.7 g) in pyridine (20 ml) at 0° C. The mixture was stirred at room temperature for 2 hours and the solvent was evaporated under reduced pressure. Thereto was added diluted hydrochloric acid-ethyl acetate. The precipitated crystals were collected by filtration to give N-(2-hydroxy-4-methylphenyl)-2-bromo-5-methyl-3-thiophenecarboxamide (3.3 g).

melting point 210–212° C.

STARTING MATERIAL SYNTHESIS EXAMPLE 72

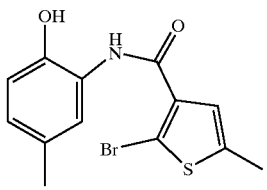

2-Bromo-5-methyl-3-thiophenecarboxylic acid (2 g) was suspended in thionyl chloride (10 ml) and the mixture was stirred under reflux with heating for 50 minutes. Thionyl chloride was evaporated under reduced pressure and the residue was dissolved in toluene (20 ml). This toluene solution was added dropwise to a solution of 2-amino-4-methylphenol (1.1 g) in pyridine (20 ml) at 0° C. The mixture was stirred at room temperature for 2.5 hours and the solvent was evaporated under reduced pressure. Thereto was added ethyl acetate-diisopropyl ether. The precipitated crystals were collected by filtration to give N-(2-hydroxy-5-methylphenyl)-2-bromo-5-methyl-3-thiophenecarboxamide (2.6 g).

melting point 173–175° C.

STARTING MATERIAL SYNTHESIS EXAMPLE 73

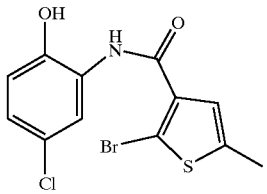

2-Bromo-5-methyl-3-thiophenecarboxylic acid (3.5 g) was suspended in thionyl chloride (17 ml) and the mixture was stirred under reflux with heating for 1 hour. Thionyl chloride was evaporated under reduced pressure and the residue was dissolved in toluene (20 ml). This toluene solution was added dropwise to a solution of 2-amino-4-chlorophenol (2.3 g) in pyridine (35 ml) at 0° C. The mixture was stirred at room temperature for 1.5 hours and the solvent was evaporated under reduced pressure. To the residue was added ethyl acetate-diisopropyl ether and the precipitated crystals were collected by filtration and washed with diluted hydrochloric acid and then diisopropyl ether to give N-(3-chloro-6-hydroxyphenyl)-2-bromo-5-methyl-3-thiophenecarboxamide (4.1 g).

melting point 232–235° C.

STARTING MATERIAL SYNTHESIS EXAMPLE 74

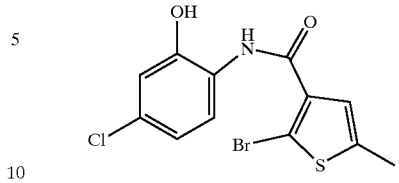

2-Bromo-5-methyl-3-thiophenecarboxylic acid (4.6 g) was suspended in thionyl chloride (15 ml) and the mixture was stirred under reflux with heating for 35 minutes. Thionyl chloride was evaporated under reduced pressure and the residue was dissolved in toluene (20 ml). This toluene solution was added dropwise to a solution of 2-amino-5-chlorophenol (3.0 g) in pyridine (15 ml) at 0° C. The mixture was stirred at room temperature for 1 hour and poured into diluted hydrochloric acid-ethyl acetate. The precipitated crystals were collected by filtration to give N-(4-chloro-2-hydroxyphenyl)-2-bromo-5-methyl-3-thiophenecarboxamide (3.4 g).

$^1$H-NMR(400 MHz, CD$_3$OD) δ2.42(3H, s, CH$_3$), 6.87 (1H, d, J=8.8 Hz, ArH), 6.90(1H, s, H of thiophene ring), 7.12(1H, s, ArH), 7.84(1H, d, J=8.8 Hz, ArH), 9.23(1H, br, NH or OH), 10.48(1H, br, NH or OH)

STARTING MATERIAL SYNTHESIS EXAMPLE 75

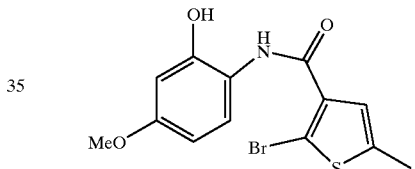

2-Bromo-5-methyl-3-thiophenecarbonyl chloride (2.6 g), prepared in the same manner as above from 2-bromo-5-methyl-3-thiophenecarboxylic acid and thionyl chloride, was suspended in toluene (20 ml). This toluene solution was added dropwise to a solution of 2-amino-5-methoxyphenol (2.0 g) in pyridine (50 ml) at 0° C. The mixture was stirred at room temperature for 2.5 hours and the solvent was evaporated under reduced pressure. The precipitated crystals were collected by filtration, and washed with diluted hydrochloric acid and diisopropyl ether to give N-(2-hydroxy-4-methoxyphenyl)-2-bromo-5-methyl-3-thiophenecarboxamide (2.1 g).

melting point 183–184° C.

STARTING MATERIAL SYNTHESIS EXAMPLE 76

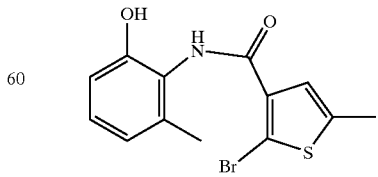

2-Bromo-5-methyl-3-thiophenecarbonyl chloride (2.6 g), prepared in the same manner as above from 2-bromo-5- methyl-3-thiophenecarboxylic acid and thionyl chloride, was suspended in toluene (20 ml). This toluene solution was added dropwise to a solution of 2-amino-3-methylphenol (1.4 g) in pyridine (30 ml) at 0° C. The mixture was stirred at room temperature for 3 hours and diisopropyl ether-ethyl acetate was added. The solvent was evaporated under reduced pressure. The precipitated crystals were collected by filtration, and washed with diluted hydrochloric acid and diisopropyl ether to give N-(2-hydroxy-6-methylphenyl)-2-bromo-5-methyl-3-thiophenecarboxamide (3.0 g).

melting point 164–167° C.

STARTING MATERIAL SYNTHESIS EXAMPLE 77

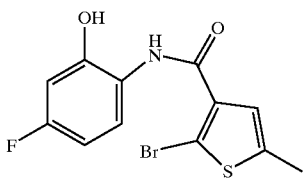

In the same manner as in Starting Material Synthesis Example 67 and using 2-bromo-5-methyl-3-thiophenecarboxylic acid, thionyl chloride and 2-amino-5-fluorophenol, N-(4-fluoro-2-hydroxyphenyl)-2-bromo-5-methyl-3-thiophenecarboxamide is obtained.

STARTING MATERIAL SYNTHESIS EXAMPLE 78

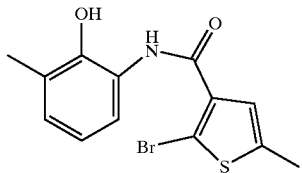

In the same manner as in Starting Material Synthesis Example 67 and using 2-bromo-5-methyl-3-thiophenecarboxylic acid, thionyl chloride and 2-amino-6-methylphenol, N-(2-hydroxy-3-methylphenyl)-2-bromo-5-methyl-3-thiophenecarboxamide is obtained.

STARTING MATERIAL SYNTHESIS EXAMPLE 79

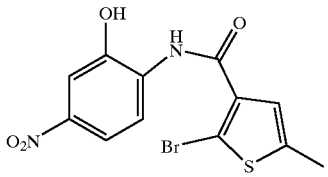

In the same manner as in Starting Material Synthesis Example 67 and using 2-bromo-5-methyl-3-thiophenecarboxylic acid, thionyl chloride and 2-amino-5-nitrophenol, N-(2-hydroxy-4-nitrophenyl)-2-bromo-5-methyl-3-thiophenecarboxamide is obtained.

STARTING MATERIAL SYNTHESIS EXAMPLE 80

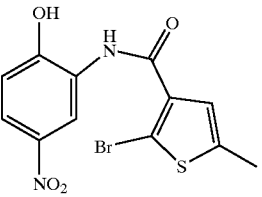

In the same manner as in Starting Material Synthesis Example 67 and using 2-bromo-5-methyl-3-thiophenecarboxylic acid, thionyl chloride and 2-amino-4-nitrophenol, N-(2-hydroxy-5-nitrophenyl)-2-bromo-5-methyl-3-thiophenecarboxamide is obtained.

STARTING MATERIAL SYNTHESIS EXAMPLE 81

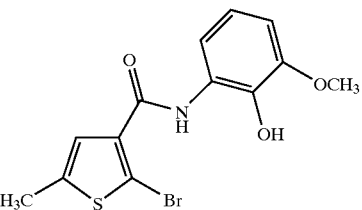

2-Bromo-5-methyl-3-thiophenecarboxylic acid (2.52 g) was suspended in thionyl chloride (12 ml), the mixture was stirred at 60° C. for 70 minutes. Thionyl chloride was evaporated under reduced pressure and the residue was dissolved in toluene (20 ml). This toluene solution was added dropwise to a solution of 2-amino-6-methoxyphenol hydrochloride (2.0 g) in pyridine (42 ml) at 0° C. The mixture was stirred at room temperature for 2 hours and the solvent was evaporated under reduced pressure. To the residue was added ethyl acetate-diisopropyl ether. The precipitated crystals were collected by filtration, and washed with 0.5N hydrochloric acid, diisopropyl ether and hexane to give N-(2-hydroxy-3-methoxyphenyl)-2-bromo-5-methyl-3-thiophenecarboxamide (3.46 g).

melting point 169–172° C.

$^1$H-NMR(400 MHz, CDCl$_3$) δ2.41(3H, s, CH$_3$), 3.89(3H, s, CH$_3$), 6.27(1H, s, OH), 6.68(1H, d, J=8.3 Hz, ArH), 6.86(1H, dd, J=8.3 Hz, ArH), 7.09(1H, s, H of thiophene ring), 8.62(1H, br.s, NH).

MS: m/e 342.

Example 98

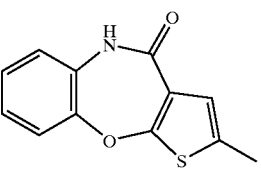

To a solution of N-(2-hydroxyphenyl)-2-bromo-5-methyl-3-thiophenecarboxamide (15 g) in dimethyl sulfoxide (100 ml) was added potassium carbonate (13 g), and the mixture was stirred at 140° C. for 1.5 hours. The reaction system was cooled to room temperature and the reaction mixture was poured into water (800 ml). After neutralization with hydrochloric acid, the mixture was extracted twice with chloroform and washed with water and saturated aqueous sodium hydrogencarbonate solution. The organic layer was dried over sodium sulfate and the solvent was evaporated under reduced pressure. To the residue was added chloroform and the crystals were collected by filtration to give 2-methylthieno[2,3-b][1,5]benzoxazepin-4(5H)-one (3.3 g).

$^1$H-NMR(400 MHz, DMSO-d$_6$) δ2.31(1H, s, CH$_3$), 6.72 (1H, s, H of thiophene ring), 7.09–7.23(4H, m, ArH), 13.12(1H, br, NH)

Example 99

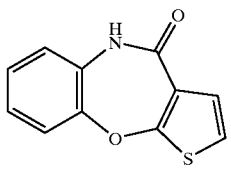

To a solution of N-(2-hydroxyphenyl)-2-bromo-3-thiophenecarboxamide (16 g) in dimethyl sulfoxide (160 ml) was added potassium carbonate (15 g) and the mixture was stirred at 150–160° C. for 25 minutes. The reaction system was cooled to room temperature and the reaction mixture was poured into water-ethyl acetate. The precipitated crystals were collected by filtration and washed with water and diisopropyl ether to give thieno[2,3-b][1,5]benzoxazepin-4 (5H)-one (5.3 g).

$^1$H-NMR(400 MHz, DMSO-d$_6$) δ7.02(2H, s, H of thiophene ring), 7.12–7.26(4H, m, ArH), 10.20(1H, br, NH)

Example 100

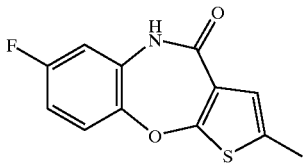

To a solution of N-(3-fluoro-6-hydroxyphenyl)-2-bromo-3-thiophenecarboxamide (3.3 g) in dimethyl sulfoxide (100 ml) was added potassium carbonate (2.8 g) and the mixture was stirred at 140° C. for 1 hour. The reaction system was cooled to room temperature and the reaction mixture was poured into diluted hydrochloric acid under ice-cooling. The precipitated crystals were collected by filtration, dissolved in chloroform, washed with saturated brine, and dried over magnesium sulfate. The solvent was evaporated under reduced pressure and the residue was purified by silica gel column chromatography (chloroform:methanol=99.5:0.5). The solvent was evaporated under reduced pressure. To the residue was added ethyl acetate and the precipitated crystals were collected by filtration to give 7-fluoro-2-methylthieno [2,3-b][1,5]benzoxazepin-4(5H)-one (350 mg).

melting point 274–275° C.

Example 101

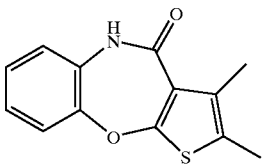

To a solution of N-(2-hydroxyphenyl)-2-bromo-4,5-dimethyl-3-thiophenecarboxamide (3.3 g) in dimethyl sulfoxide (50 ml) was added potassium carbonate (2.8 g) and the mixture was stirred at 160–170° C. for 20 minutes. The reaction system was cooled to room temperature and the reaction mixture was poured into water-ethyl acetate. The insoluble matter was filtered and the filtrate was extracted with ethyl acetate, washed with water and dried over magnesium sulfate. The solvent was evaporated under reduced pressure, and the residue was purified by silica gel column chromatography (hexane:ethyl acetate=4:1) to give 2,3-dimethylthieno[2,3-b][1,5]benzoxazepin-4(5H)-one (1.4 g).

$^1$H-NMR(400 MHz, DMSO-d$_6$) δ2.13(3H, s, CH$_3$), 2.21 (3H, s, CH$_3$), 7.11–7.22(4H, m, ArH), 10.17(1H, br, NH)

Example 102

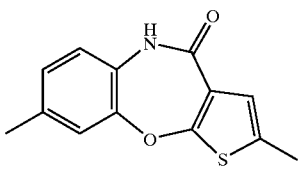

To a solution of N-(2-hydroxy-4-methylphenyl)-2-bromo-3-thiophenecarboxamide (3.4 g) in dimethyl sulfoxide (30 ml) was added potassium carbonate (2.9 g) and the mixture was stirred at 140–150° C. for 1 hour. The reaction system was cooled to room temperature and the reaction mixture was poured into water. The precipitated crystals were collected by filtration, washed with water and purified by silica gel column chromatography (chloroform) to give 2, 8-dimethylthieno[2,3-b][1,5]benzoxazepin-4(5H)-one (1.2 g).

melting point 211–215° C.

Example 103

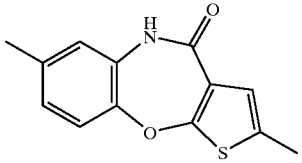

To a solution of N-(2-hydroxy-5-methylphenyl)-2-bromo-3-thiophenecarboxamide (2.9 g) in dimethyl sulfoxide (24 ml) was added potassium carbonate (2.4 g) and the mixture was stirred at 140–150° C. for 2 hours. The reaction system was cooled to room temperature and the reaction mixture was poured into ice water. The precipitated crystals were collected by filtration. The filtrate was extracted twice with chloroform and the organic layer was dried over sodium sulfate. The solvent was evaporated under reduced pressure.

The residue and the above-mentioned crystals were combined and purified by silica gel column chromatography (chloroform:methanol=20:1). The obtained solid was collected by filtration from hexane to give 2,7-dimethylthieno[2,3-b][1,5]benzoxazepin-4(5H)-one (1.0 g).

melting point 175–179° C.

Example 104

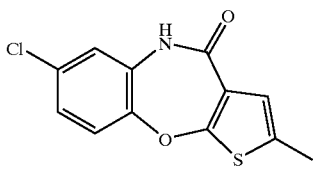

To a solution of N-(3-chloro-6-hydroxyphenyl)-2-bromo-3-thiophenecarboxamide (4.1 g) in dimethyl sulfoxide (33 ml) was added potassium carbonate (3.3 g), and the mixture was stirred at 140–150° C. for 75 minutes. The reaction system was cooled to room temperature and the reaction mixture was poured into ice water. The precipitated crystals were collected by filtration. The filtrate was extracted twice with chloroform, the organic layer was dried over sodium sulfate and the solvent was evaporated under reduced pressure. The residue and the above-mentioned crystals were combined and purified by silica gel column chromatography (chloroform:methanol=20:1, hexane:ethyl acetate=1:1-ethyl acetate:methanol=20:1). The obtained solid was collected by filtration from hexane-ethyl acetate to give 7-chloro-2-methylthieno[2,3-b][1,5]benzoxazepin-4(5H)-one (660 mg).

melting point 250–253° C.

Example 105

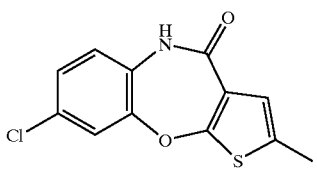

Similar reaction is carried out using N-(4-chloro-2-hydroxyphenyl)-2-bromo-5-methyl-3-thiophenecarboxamide and potassium carbonate to give 8-chloro-2-methylthieno[2,3-b][1,5]benzoxazepin-4(5H)-one.

Example 106

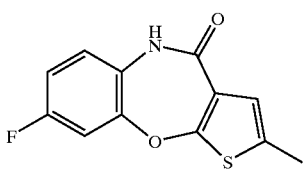

Similar reaction is carried out using N-(4-fluoro-2-hydroxyphenyl)-2-bromo-5-methyl-3-thiophenecarboxamide and potassium carbonate to give 8-fluoro-2-methylthieno[2,3-b][1,5]benzoxazepin-4(5H)-one.

Example 107

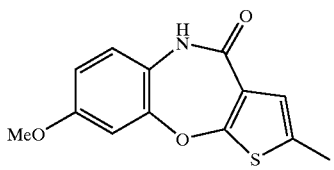

To a solution of N-(2-hydroxy-4-methoxyphenyl)-2-bromo-5-methyl-3-thiophenecarboxamide (2.1 g) in dimethyl sulfoxide (17 ml) was added potassium carbonate (1.7 g), and the mixture was stirred at 145° C. for 2 hours. The reaction system was cooled to room temperature and the reaction mixture was poured into ice water. The precipitated crystals were collected by filtration and the obtained crystals were purified by silica gel column chromatography (chloroform:methanol=20:0–20:1). The obtained solid was collected by filtration from diisopropyl ether-ethyl acetate-methanol to give 8-methoxy-2-methylthieno[2,3-b][1,5]benzoxazepin-4(5H)-one (530 mg).

$^1$H-NMR(400 MHz, DMSO-d$_6$) δ2.31(3H, s, CH$_3$), 3.72 (3H, s, OCH$_3$), 6.52(1H, s, H of thiophene ring), 6.70–7.07 (2H, m, ArH), 7.28(1H, d, ArH), 10.25(1H, br, NH)

Example 108

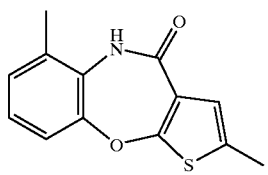

To a solution of N-(2-hydroxy-6-methylphenyl)-2-bromo-5-methyl-3-thiophenecarboxamide (3.0 g) in dimethyl sulfoxide (25 ml) was added potassium carbonate (2.5 g), and the mixture was stirred at 145° C. for 2 hours. The reaction system was cooled to room temperature and poured into ice water. The precipitated crystals were collected by filtration and the filtrate was extracted with chloroform, washed twice with water, and dried over sodium sulfate. The solvent was evaporated under reduced pressure and the residue and the crystals obtained earlier were purified by silica gel column chromatography (chloroform:methanol=20:0–20:1). The obtained solid was collected by filtration from diisopropyl ether-hexane to give 2,6-dimethylthieno[2,3-b][1,5]benzoxazepin-4(5H)-one (700 mg).

melting point 198–200° C.

Example 109

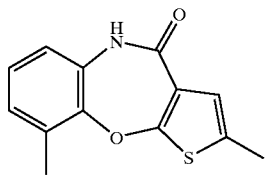

In the same manner as in Example 98 and using N-(2-hydroxy-3-methylphenyl)-2-bromo-5-methyl-3-thiophenecarboxamide and potassium carbonate, 2,9-dimethylthieno[2,3-b][1,5]benzoxazepin-4(5H)-one is obtained.

Example 110

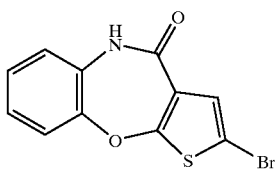

Thieno[2,3-b][1,5]benzoxazepin-4(5H)-one (2 g) was suspended in acetic acid (30 ml) and a solution of bromine (1.5 g) in acetic acid (10 ml) was added dropwise over 30 minutes. The mixture was stirred at room temperature for 35 minutes and poured into water. The precipitated crystals were collected by filtration and washed with water and diisopropyl ether to give 2-bromothieno[2,3-b][1,5]benzoxazepin-4(5H)-one (2.2 g).

$^1$H-NMR(400 MHz, DMSO-d$_6$) δ7.12–7.16(3H, m, ArH, H of thiophene ring), 7.20–7.26(2H, m, ArH), 10.29(1H, br, NH)

Example 111

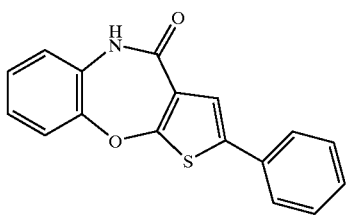

2-Bromothieno[2,3-b][1,5]benzoxazepin-4(5H)-one (1.0 g) was dissolved in 2M sodium carbonate (8 ml)-toluene (8 ml)-ethanol (8 ml) and phenyl borate (620 mg) and tetrakistriphenylphosphine palladium (390 mg) were added. The mixture was stirred under reflux with heating for 80 minutes. The reaction system was cooled to room temperature and diisopropyl ether and ethyl acetate were added. The precipitated crystals were collected by filtration and the obtained crystals were washed with ethyl acetate and water to give 2-phenylthieno[2,3-b][1,5]benzoxazepin-4(5H)-one (830 mg).

$^1$H-NMR(400 MHz, DMSO-d$_6$) δ7.18–7.46(8H, m, ArH), 7.65(2H, m, ArH), 10.34(1H, br, NH)

Example 112

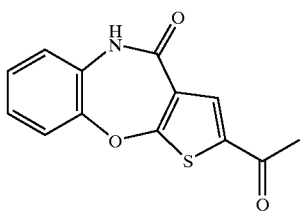

Thieno[2,3-b][1,5]benzoxazepin-4(5H)-one (5 g) was suspended to 1,2-dichloroethane (50 ml) and acetyl chloride was added (2.2 g). To this reaction system was added portionwise aluminum chloride (15 g) under ice-cooling and the mixture was stirred at room temperature for 10 minutes. The reaction system was poured into ice. Chloroform was added and the mixture was stirred for 15 minutes. The precipitated crystals were collected by filtration to give 2-acetylthieno[2,3-b][1,5]benzoxazepin-4(5H)-one (5.2 g).

$^1$H-NMR(400 MHz, CDCl$_3$) δ2.50(3H, s, CH$_3$), 6.97(1H, d, ArH), 7.17–7.20(3H, m, ArH), 7.80(1H, s, H of thiophene ring)

Example 113

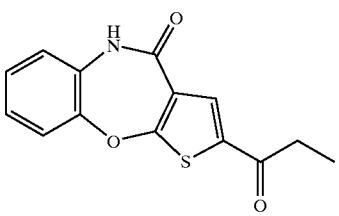

Thieno[2,3-b][1,5]benzoxazepin-4(5H)-one (1.5 g) was suspended in 1,2-dichloroethane (20 ml) and propionyl chloride (770 mg) was added. To this reaction system was added portionwise aluminum chloride (4.7 g) under ice-cooling. Insoluble matter was filtrated, and the filtrate was poured into ice water and chloroform was added. The aqueous layer was extracted twice with chloroform and the combined organic layer was dried over sodium sulfate. The solvent was evaporated under reduced pressure and the precipitated crystals were collected by filtration to give 2-propionylthieno[2,3-b][1,5]benzoxazepin-4(5H)-one (1.4 g).

melting point 205–210° C. (decomposition).

Example 114

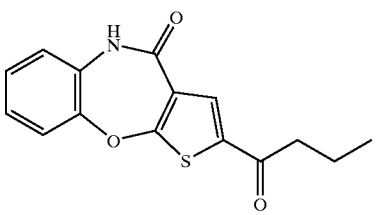

Thieno[2,3-b][1,5]benzoxazepin-4(5H)-one (1.5 g) was suspended in 1,2-dichloroethane (20 ml) and butyryl chloride (880 mg) was added. To this reaction system was added portionwise aluminium chloride (4.6 g) under ice-cooling. The mixture was stirred at room temperature for 45 minutes. Insoluble matter was filtrated and the filtrate was poured into ice water, and chloroform was added. The organic layer was washed with water and dried over sodium sulfate. The solvent was evaporated under reduced pressure and water-ethanol was added. The precipitated crystals were collected by filtration. The obtained crystals were washed with chloroform-diisopropyl ether to give 2-butyrylthieno[2,3-b][1,5]benzoxazepin-4(5H)-one (1.2 g).

$^1$H-NMR(400 MHz, DMSO-d$_6$) δ0.89(3H, t, J=7.3 Hz, CH$_3$), 1.59(2H, m, CH$_2$), 2.90(2H, t, J=7.3 Hz, CH$_2$) 7.14–7.31(4H, m, ArH), 7.93(1H, s, H of thiophene ring), 10.41(1H, br, NH)

Example 115

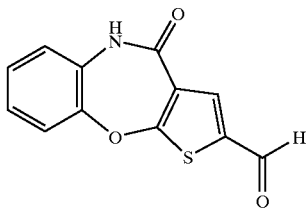

Thieno[2,3-b][1,5]benzoxazepin-4(5H)-one (1.9 g) was suspended in methylene chloride (20 ml) and dichloromethylmethyl ether (4.0 g) was added. To this reaction system was added aluminum chloride (4.6 g) under ice-cooling and the mixture was stirred for 15 minutes. The reaction mixture was poured into ice water-chloroform and the mixture was stirred at room temperature for 20 minutes. The aqueous layer was extracted 5 times with chloroform and the combined organic layer was dried over sodium sulfate. The solvent was evaporated under reduced pressure and diisopropyl ether was added to the residue. The precipitated crystals were collected by filtration to give 2-formylthieno[2,3-b][1,5]benzoxazepin-4(5H)-one (1.2 g).

$^1$H-NMR(400 MHz, DMSO-d$_6$) δ7.14–7.33(4H, m, ArH), 8.08(1H, s, H of thiophene ring), 9.81(1H, s, HC=O), 10.45(1H, br, NH)

Example 116

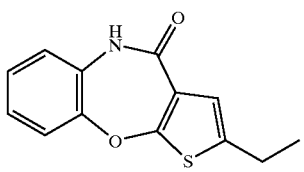

2-Acetylthieno[2,3-b][1,5]benzoxazepin-4(5H)-one (1.5 g) was dissolved in trifluoroacetic acid (20 ml) and triethylsilane (2 g) was added. The mixture was stirred at room temperature for 42 hours. The solvent was evaporated under reduced pressure and the residue was dissolved in chloroform. The mixture was washed with water and saturated aqueous sodium hydrogencarbonate solution, and dried over sodium sulfate. The solvent was evaporated under reduced pressure. To the residue were added chloroform and ethyl acetate and the precipitated crystals were collected by filtration. The obtained crystals were washed with diisopropyl ether to give 2-ethylthieno[2,3-b][1,5]benzoxazepin-4(5H)-one (1.1 g).

$^1$H-NMR(400 MHz, CDCl$_3$) δ1.26(3H, t, J=7.3 Hz, CH$_3$), 2.69(2H, q, J=7.0 Hz, 16.1 Hz, CH$_2$), 6.82(1H, s, H of thiophene ring), 6.93(1H, d, J=7.8 Hz, ArH), 7.10–7.18(3H, m, ArH)

Example 117

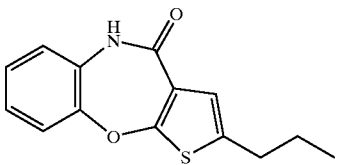

2-Propionylthieno[2,3-b][1,5]benzoxazepin-4(5H)-one (1.2 g) was dissolved in trifluoroacetic acid (20 ml) and triethylsilane (2 g) was added. The mixture was stirred at room temperature for 20 hours. The solvent was evaporated under reduced pressure and the residue was dissolved in chloroform. The mixture was washed with water and saturated aqueous sodium hydrogencarbonate solution and dried over sodium sulfate. The solvent was evaporated under reduced pressure. To the residue were added chloroform and ethyl acetate and the precipitated crystals were collected by filtration. The obtained crystals were washed with diisopropyl ether to give 2-propylthieno[2,3-b][1,5]benzoxazepin-4(5H)-one (930 mg).

$^1$H-NMR(400 MHz, CDCl$_3$) δ0.94(3H, t, J=7.3 Hz, CH$_3$), 1.61(2H, m, CH$_2$), 2.60(2H, t, J=7.3 Hz, CH$_2$), 6.79(1H, s, H of thiophene ring), 6.91(1H, d, J=7.3 Hz, ArH), 7.08–7.15 (3H, m, ArH), 7.34(br, NH)

Example 118

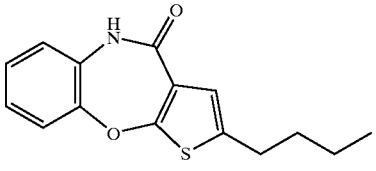

2-Butyrylthieno[2,3-b][1,5]benzoxazepin-4(5H)-one (1.1 g) was dissolved in trifluoroacetic acid (20 ml) and triethylsilane (1.3 g) was added. The mixture was stirred at room temperature for 72 hours. The solvent was evaporated under reduced pressure and the residue was dissolved in chloroform. The mixture was washed with water and saturated aqueous sodium hydrogencarbonate solution and dried over sodium sulfate. The solvent was evaporated under reduced pressure. To the residue were added chloroform and ethyl acetate and the precipitated crystals were collected by filtration. The obtained crystals were washed with diisopropyl ether to give 2-butylthieno[2,3-b][1,5]benzoxazepin-4(5H)-one (600 mg).

$^1$H-NMR(400 MHz, DMSO-d$_6$) δ0.87(3H, t, J=7.3 Hz, CH$_3$), 1.30(2H, m, CH$_2$), 1.52(2H, m, CH$_2$), 2.65(2H, t, J=7.8 Hz, CH$_2$), 6.74(1H, s, H of thiophene ring), 7.11–7.23 (4H, m, ArH), 10.14(1H, br, NH)

Example 119

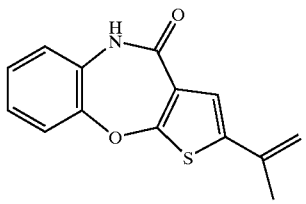

2-Acetylthieno[2,3-b][1,5]benzoxazepin-4(5H)-one (1.8 g) was suspended in ether (15 ml) and 20 equivalent amounts of magnesium methyl iodide was added under ice-cooling. The mixture was stirred at room temperature for 24 hours. The reaction mixture was poured into 1M hydrochloric acid under ice-cooling and insoluble matter was filtered off. The resulting mixture was extracted twice with chloroform. The chloroform layer was dried over sodium sulfate and the solvent was evaporated under reduced pressure. The residue was suspended in toluene and a catalytic amount of p-toluenesulfonic acid was added. The mixture was stirred under reflux with heating for 20 minutes. The reaction system was cooled to room temperature and the reaction mixture was washed with saturated aqueous sodium hydrogencarbonate solution. The solvent was evaporated under reduced pressure and diisopropyl ether was added to the residue. The precipitated crystals were collected by filtration to give 2-isopropenylthieno[2,3-b][1,5]benzoxazepin-4(5H)-one (800 mg).

$^1$H-NMR(400 MHz, DMSO-$d_6$) δ2.04(3H, s, $CH_3$), 5.00 (1H, s, olefine), 5.22(1H, s, olefine), 7.00(1H, s, H of thiophene ring), 7.14–7.27(4H, m, ArH), 10.25(1H, br, NH)

Example 120

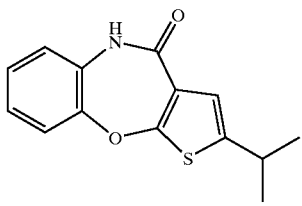

2-Isopropenylthieno[2,3-b][1,5]benzoxazepin-4(5H)-one (780 mg) was suspended in dioxane (40 ml) and 10% palladium-activated charcoal (100 mg) was added. Hydrogen was sealed in and the mixture was stirred at 40° C., 50 atm for 7.5 hours. The catalyst was filtered off and the solvent was evaporated under reduced pressure to give 2-isopropylthieno[2,3-b][1,5]benzoxazepin-4(5H)-one (600 mg).

$^1$H-NMR(400 MHz, DMSO-$d_6$) δ1.21(6H, d, J=6.8 Hz, $CH_3$), 3.01(1H, m, CH), 6.75(1H, s, H of thiophene ring), 7.10–7.23(4H, m, ArH), 10.15(1H, br, NH)

Example 121

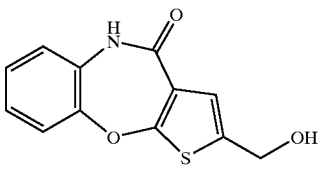

2-Formylthieno[2,3-b][1,5]benzoxazepin-4(5H)-one (1.6 g) was suspended in methanol (30 ml) and sodium borohydride (480 mg) was added. The mixture was stirred at room temperature for 1.5 hours. The reaction mixture was diluted with water and extracted 3 times with chloroform. The organic layer was dried over sodium sulfate and the solvent was evaporated under reduced pressure. To the residue were added chloroform and diisopropyl ether and the precipitated crystals were collected by filtration to give 2-hydroxymethylthieno[2,3-b][1,5]benzoxazepin-4(5H)-one (1.0 g).

$^1$H-NMR(400 MHz, DMSO-$d_6$) δ4.47(2H, d, $CH_2$), 5.52 (1H, t, OH), 6.84(1H, s, H of thiophene ring), 7.10–7.23(4H, m, ArH), 10.14(1H, br, NH)

Example 122

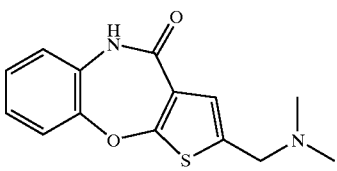

2-Hydroxymethylthieno[2,3-b][1,5]benzoxazepin-4(5H)-one (1.0 g) was dissolved in methylene chloride (10 ml) and triethylamine (450 mg) and methanesulfonyl chloride (500 mg) were added. The mixture was stirred at room temperature for 15 minutes and the solvent was evaporated under reduced pressure. Thereto was added 2M dimethylamine/methanol and the mixture was stirred at room temperature for 14 hours. The solvent was evaporated under reduced pressure and chloroform was added to the residue. After washing with water, the aqueous layer was extracted twice with chloroform. The organic layer was dried over sodium sulfate and the solvent was evaporated under reduced pressure. The residue was purified by silica gel column chromatography (ethyl acetate) to give 2-(N,N-dimethylaminomethyl)thieno[2,3-b][1,5]benzoxazepin-4(5H)-one (500 mg).

$^1$H-NMR(400 MHz, DMSO-$d_6$) δ1.98(6H, s, $CH_3$), 3.46 (2H, s, $CH_2$), 6.87(1H, s, H of thiophene ring), 7.12–7.25 (4H, m, ArH), 10.15(1H, br, NH)

Example 123

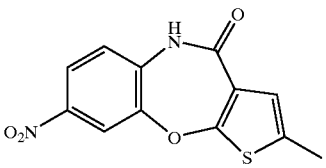

In the same manner as in Example 98 and using N-(2-hydroxy-4-nitrophenyl)-2-bromo-5-methyl-3- thiophenecarboxamide and potassium carbonate, 2-methyl-8-nitrothieno[2,3-b][1,5]benzoxazepin-4(5H)-one is obtained.

Example 124

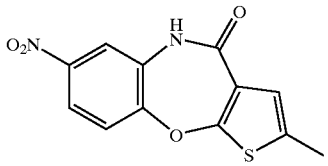

In the same manner as in Example 98 and using N-(2-hydroxy-5-nitrophenyl)-2-bromo-5-methyl-3-thiophenecarboxamide and potassium carbonate, 2-methyl-7-nitrothieno[2,3-b][1,5]benzoxazepin-4(5H)-one is obtained.

Example 125

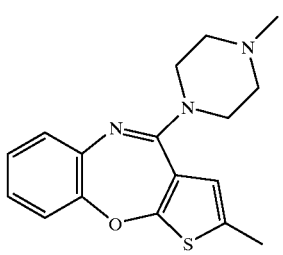

2-Methylthieno[2,3-b][1,5]benzoxazepin-4(5H)-one (1.0 g) was suspended in phosphorus oxychloride (6.4 ml) and N,N-dimethylaniline (240 mg) was added. The mixture was stirred under reflux with heating for 1 hour. The solvent was completely evaporated azeotropically with toluene under reduced pressure and 1-methylpiperazine (25 ml) was added to the residue. The mixture was stirred under reflux with heating for 40 minutes. The reaction system was cooled to room temperature and the solvent was evaporated under reduced pressure. To the residue was added chloroform, and the mixture was washed with water and saturated brine and dried over sodium sulfate. The solvent was evaporated under reduced pressure and the residue was purified by silica gel column chromatography (chloroform:methanol=100:1). The obtained compound was recrystallized from diisopropyl ether to give 2-methyl-4-(4-methylpiperazin-1-yl)thieno[2,3-b][1,5]benzoxazepine (520 mg).

melting point 132–133° C.

Example 126

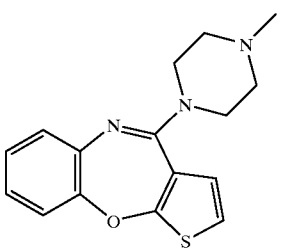

Thieno[2,3-b][1,5]benzoxazepin-4(5H)-one (1.2 g) was suspended in phosphorus oxychloride (8.5 ml) and N,N-dimethylaniline (310 mg) was added. The mixture was stirred under reflux with heating for 1 hour and the solvent was completely evaporated azeotropically with toluene under reduced pressure. To the residue was added 1-methylpiperazine (25 ml) and the mixture was stirred under reflux with heating for 30 minutes. The reaction system was cooled to room temperature and the solvent was evaporated under reduced pressure. To the residue was added chloroform, and the mixture was washed with water and saturated brine and dried over sodium sulfate. The solvent was evaporated under reduced pressure and the residue was purified by silica gel column chromatography (chloroform:methanol=100:1.5). The obtained compound was converted to fumarate, which was recrystallized from ethyl acetate-ethanol to give 4-(4-methylpiperazin-1-yl)thieno[2,3-b][1,5]benzoxazepine fumarate (650 mg).

melting point 200–202° C.

Example 127

2-Bromothieno[2,3-b][1,5]benzoxazepin-4(5H)-one (800 mg) was

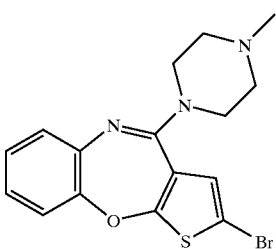

suspended in phosphorus oxychloride (5 ml) and N,N-dimethylaniline (155 mg) was added. The mixture was stirred under reflux with heating for 1 hour and the solvent was completely evaporated azeotropically with toluene under reduced pressure. To the residue was added 1-methylpiperazine (10 ml) and the mixture was stirred at room temperature for 30 minutes and then under reflux with heating for 5 minutes. The reaction system was cooled to room temperature and the solvent was evaporated under reduced pressure. To the residue was added chloroform, and the mixture was washed with water and saturated brine and dried over sodium sulfate. The solvent was evaporated under reduced pressure and the residue was purified by silica gel column chromatography (chloroform:methanol=100:1). The obtained compound was recrystallized from diisopropyl ether-ethyl acetate to give 2-bromo-4-(4-methylpiperazin-1-yl)thieno[2,3-b][1,5]benzoxazepine (300 mg).

melting point 150–151° C.

Example 128

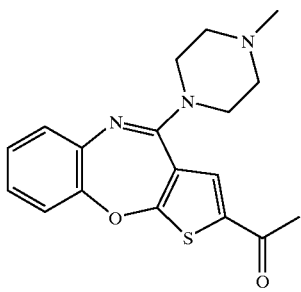

2-Acetylthieno[2,3-b][1,5]benzoxazepin-4(5H)-one (1.2 g) was suspended in phosphorus oxychloride (7 ml) and N,N-dimethylaniline (280 mg) was added. The mixture was stirred under reflux with heating for 1.5 hours. The solvent was completely evaporated azeotropically with toluene under reduced pressure. To the residue was added 1-methylpiperazine (20 ml) and the mixture was stirred at 80° C. for 15 minutes. The reaction system was cooled to room temperature and the solvent was evaporated under reduced pressure. To the residue was added chloroform, and the mixture was washed with water and saturated brine and dried over sodium sulfate. The solvent was evaporated under reduced pressure and the residue was purified by silica gel column chromatography (chloroform:methanol=100:0.5). The obtained compound was recrystallized from diisopropyl ether-ethyl acetate to give 2-acetyl-4-(4-methylpiperazin-1-yl)thieno[2,3-b][1,5]benzoxazepine (80 mg).

melting point 143–144° C.

Example 129

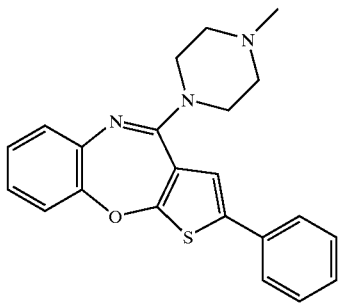

2-Phenylthieno[2,3-b][1,5]benzoxazepin-4(5H)-one (1.2 g) was suspended in phosphorus oxychloride (6.5 ml) and N,N-dimethylaniline (250 mg) was added. The mixture was stirred under reflux with heating for 1 hour. The solvent was completely evaporated azeotropically with toluene under reduced pressure and 1-methylpiperazine (20 ml) was added to the residue. The mixture was stirred under reflux with heating for 1 hour. The reaction system was cooled to room temperature and the solvent was evaporated under reduced pressure. Chloroform was added to the residue, and the mixture was washed with water and saturated brine and dried over sodium sulfate. The solvent was evaporated under reduced pressure and the residue was purified by silica gel column chromatography (chloroform:methanol=100:1). The obtained compound was recrystallized from ethyl acetate to give 4-(4-methylpiperazin-1-yl)-2-phenylthieno[2,3-b][1,5]benzoxazepine (620 mg).

melting point 163–164° C.

Example 130

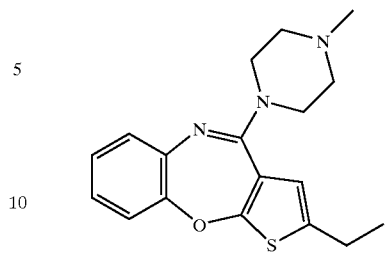

2-Ethylthieno[2,3-b][1,5]benzoxazepin-4(5H)-one (1.1 g) was suspended in phosphorus oxychloride (7 ml) and N,N-dimethylaniline (270 mg) was added. The mixture was stirred under reflux with heating for 3 hours and the solvent was completely evaporated azeotropically with toluene under reduced pressure. To the residue was added 1-methylpiperazine (13 ml) and the mixture was stirred under reflux with heating for 1 hour. The reaction system was cooled to room temperature and the solvent was evaporated under reduced pressure. To the residue was added ethyl acetate, and the mixture was washed with water and saturated brine and dried over sodium sulfate. The solvent was evaporated under reduced pressure and the residue was purified by silica gel column chromatography (chloroform:methanol=100:1). The obtained compound was recrystallized from ethyl acetate-ethanol as maleate to give 2-ethyl-4-(4-methylpiperazin-1-yl)thieno[2,3-b][1,5]benzoxazepine dimaleate (630 mg).

melting point 154–156+ C.

Example 131

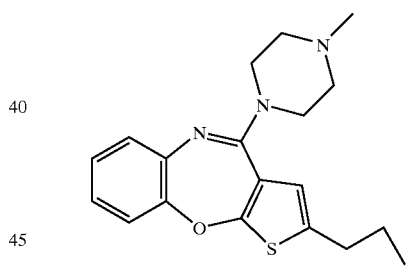

2-Propylthieno[2,3-b][1,5]benzoxazepin-4(5H)-one (910 mg) was suspended in phosphorus oxychloride (6 ml) and N,N-dimethylaniline (220 mg) was added. The mixture was stirred under reflux with heating for 1 hour. The solvent was completely evaporated azeotropically with toluene under reduced pressure and to the residue was added 1-methylpiperazine (10 ml). The mixture was stirred under reflux with heating for 40 minutes. The reaction system was cooled to room temperature and the solvent was evaporated under reduced pressure. To the residue was added ethyl acetate, and the mixture was washed with water and saturated brine and dried over sodium sulfate. The solvent was evaporated under reduced pressure and the residue was purified by silica gel column chromatography (chloroform:methanol=100:1). The obtained compound was recrystallized from ethyl acetate-ethanol as maleate to give 4-(4-methylpiperazin-1-yl)-2-propylthieno[2,3-b][1,5]benzoxazepine dimaleate (550 mg).

melting point 175–177° C.

Example 132

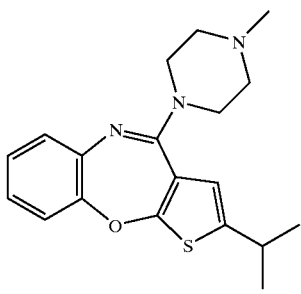

2-Isopropylthieno [2,3-b][1,5]benzoxazepin-4(5H)-one (550 mg) was suspended in phosphorus oxychloride (3 ml) and N,N-dimethylaniline (120 mg) was added. The mixture was stirred under reflux with heating for 50 minutes. The solvent was completely evaporated azeotropically with toluene under reduced pressure and to the residue was added 1-methylpiperazine (6 ml). The mixture was stirred under reflux with heating for 50 minutes. The reaction system was cooled to room temperature and the solvent was evaporated under reduced pressure. To the residue was added ethyl acetate, and the mixture was washed with water and saturated brine and dried over sodium sulfate. The solvent was evaporated under reduced pressure and the residue was purified by silica gel column chromatography (chloroform). The obtained compound was recrystallized from ethyl acetate-ethanol as maleate to give 2-isopropyl-4-(4-methylpiperazin-1-yl)thieno[2,3-b][1,5]benzoxazepine dimaleate (280 mg).

melting point 170–172° C.

Example 133

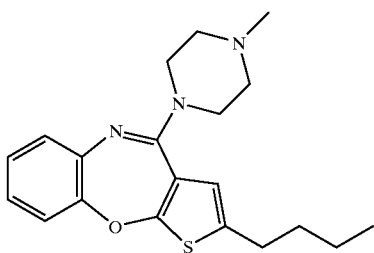

2-Butylthieno[2,3-][1,5]benzoxazepin-4(5H)-one (580 mg) was suspended in phosphorus oxychloride (4 ml) and N,N-dimethylaniline (130 mg) was added. The mixture was stirred under reflux with heating for 1 hour. The solvent was completely evaporated azeotropically with toluene under reduced pressure and to the residue was added 1-methylpiperazine (6 ml). The mixture was stirred under reflux with heating for 2 hours. The reaction system was cooled to room temperature and the solvent was evaporated under reduced pressure. To the residue was added chloroform, and the mixture was washed with water and saturated brine and dried over sodium sulfate. The solvent was evaporated under reduced pressure and the residue was purified by silica gel column chromatography (chloroform:methanol=100:1). The obtained compound was recrystallized from ethyl acetate-ethanol as fumarate to give 2-butyl-4-(4-methylpiperazin-1-yl)thieno[2,3-b][1,5] benzoxazepine fumarate (320 mg).

melting point 202–204° C.

Example 134

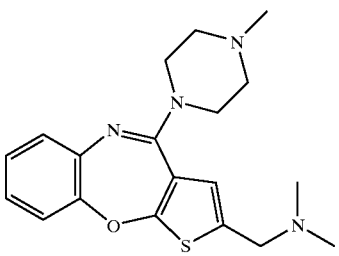

2-(N,N-Dimethylaminomethyl)thieno[2,3-b][1,5] benzoxazepin-4(5H)-one (500 mg) was suspended in phosphorus oxychloride (3 ml) and N,N-dimethylaniline (110 mg) was added. The mixture was stirred under reflux with heating for 1 hour. The solvent was completely evaporated azeotropically with toluene under reduced pressure and to the residue was added 1-methylpiperazine (6 ml). The mixture was stirred under reflux with heating for 1 hour. The reaction system was cooled to room temperature and the solvent was evaporated under reduced pressure. To the residue was added chloroform, and the mixture was washed with water and saturated brine and dried over sodium sulfate. The solvent was evaporated under reduced pressure and the residue was purified by silica gel column chromatography (chloroform:methanol=100:1). The obtained compound was recrystallized from ethyl acetate-ethanol as fumarate to give 2-(N,N-dimethylaminomethyl)-4-(4-methylpiperazin-1-yl)thieno[2,3-b][1,5]benzoxazepine 1/2 fumarate 1/5 hydrate (71 mg).

melting point 188–189° C.

Example 135

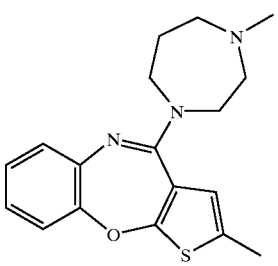

2-Methylthieno[2,3-b][1,5]benzoxazepin-4(5H)-one (800 mg) was suspended in phosphorus oxychloride (5 ml) and N,N-dimethylaniline (218 mg) was added. The mixture was stirred under reflux with heating for 1 hour. The solvent was completely evaporated azeotropically with toluene under reduced pressure and to the residue was added 1-methylhomopiperazine (10 ml). The mixture was stirred at 150° C. for 1 hour. The reaction system was cooled to room temperature and chloroform was added. The mixture was washed with water and saturated brine and dried over sodium sulfate. The solvent was evaporated under reduced pressure and the residue was purified by silica gel column chromatography (chloroform). The obtained compound was recrystallized from acetonitrile as hydrochloride to give 2-methyl-4-(4-methylhomopiperazin-1-yl)thieno[2,3-b][1, 5]benzoxazepine hydrochloride 3/4 hydrate (270 mg).

melting point 243–245° C.

Example 136

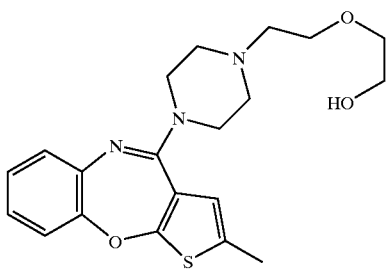

2-Methylthieno[2,3-b][1,5]benzoxazepin4(5H)-one (600 mg) was suspended in phosphorus oxychloride (4 ml) and N,N-dimethylaniline (160 mg) was added. The mixture was stirred under reflux with heating for 30 minutes. The solvent was completely evaporated azeotropically with toluene under reduced pressure and to the residue was added toluene (10 ml) and 1-[2-(2-hydroxyethoxy)ethyl]piperazine (2.5 ml). The mixture was stirred under reflux with heating for 1 hour. The reaction system was cooled to room temperature and chloroform was added. The mixture was washed with water and saturated brine and dried over sodium sulfate. The solvent was evaporated under reduced pressure and the residue was purified by silica gel column chromatography (chloroform:methanol=100:1). The obtained compound was recrystallized from hexane-ethyl acetate to give 4-[4-(2-(2-hydroxyethoxy)ethyl)piperazin-1-yl]-2-methylthieno[2,3-b][1,5]benzoxazepine (350 mg).

melting point 111–112° C.

Example 137

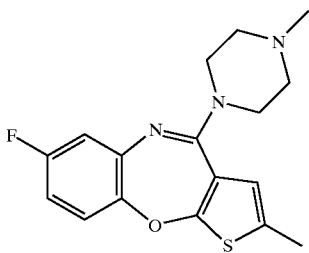

7-Fluoro-2-methylthieno[2,3-b][1,5]benzoxazepin-4(5H)-one (500 mg) was suspended in phosphorus oxychloride (5 ml) and N,N-dimethylaniline (240 mg) was added. The mixture was stirred under reflux with heating for 1.5 hours. The solvent was completely evaporated azeotropically with toluene under reduced pressure and to the residue was added 1-methylpiperazine (6 ml). The mixture was stirred under reflux with heating for 1 hour. The reaction system was cooled to room temperature and ethyl acetate was added. The mixture was washed with water and saturated brine and dried over magnesium sulfate. The solvent was evaporated under reduced pressure and the residue was purified by silica gel column chromatography (chloroform:methanol=100:1). The obtained compound was recrystallized from ethyl acetate-ethanol as maleic acid to give 7-fluoro-2-methyl-4-(4-methylpiperazin-1-yl)thieno[2,3-b][1,5]benzoxazepine dimaleate (450 mg).

melting point 137–139° C.

Example 138

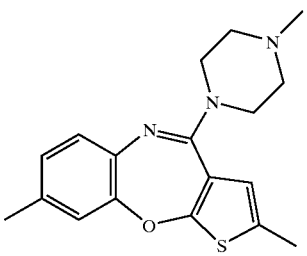

2,8-Dimethylthieno[2,3-b][1,5]benzoxazepin-4(5H)-one (1 g) was suspended in phosphorus oxychloride (6 ml) and N,N-dimethylaniline (220 mg) was added. The mixture was stirred under reflux with heating for 2.5 hours. The solvent was completely evaporated azeotropically with toluene under reduced pressure and to the residue was added 1-methylpiperazine (14 ml). The mixture was stirred under reflux with heating for 2.5 hours and the solvent was evaporated under reduced pressure. The residue was purified by silica gel column chromatography (chloroform:methanol=100:1–20:1) and the obtained compound was recrystallized from diisopropyl ether-hexane to give 2,8-dimethyl-4-(4-methylpiperazin-1-yl)thieno[2,3-b][1,5]benzoxazepine (310 mg).

melting point 149–150° C.

Example 139

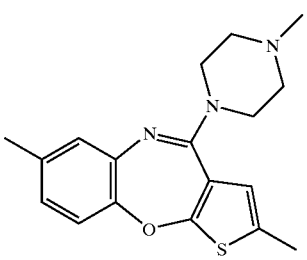

2,7-Dimethylthieno[2,3-b][1,5]benzoxazepin-4(5H)-one (1 g) was suspended in phosphorus oxychloride (6 ml) and N,N-dimethylaniline (220 mg) was added. The mixture was stirred under reflux with heating for 2 hours. The solvent was completely evaporated azeotropically with toluene under reduced pressure and to the residue was added 1-methylpiperazine (14 ml). The mixture was stirred under reflux with heating for 3.5 hours. The solvent was evaporated under reduced pressure and the residue was purified by silica gel column chromatography (chloroform:methanol=50:1–20:1) and the obtained compound was recrystallized from diisopropyl ether-hexane to give 2,7-dimethyl-4-(4-methylpiperazin-1-yl)thieno[2,3-b][1,5]benzoxazepine (330 mg).

melting point 146–148° C.

Example 140

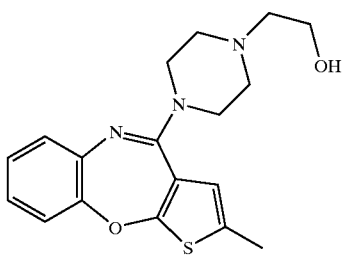

2-Methylthieno[2,3-b][1,5]benzoxazepin-4(5H)-one (1.2 g) was suspended in phosphorus oxychloride (8 ml). N,N-Dimethylaniline (280 mg) was added and the mixture was refluxed under heating for 3 hours. The solvent was completely evaporated azeotropically with toluene under reduced pressure. To the residue was added 1-(2-hydroxyethyl)piperazine (15 ml) and the mixture was stirred at 140–150° C. for 2 hours. The reaction mixture was purified by silica gel column chromatography (chloroform:methanol=50:1, ethyl acetate). The obtained compound was further recrystallized from ethyl acetate—hexane to give 4-[4-(2-hydroxyethyl)piperazin-1-yl]-2-methylthieno[2,3-b][1,5]benzoxazepine (210 mg).

melting point 87–89° C.

Example 141

7-Chloro-2-methylthieno[2,3-b][1,5]benzoxazepin-4(5H)-one (660 mg) was

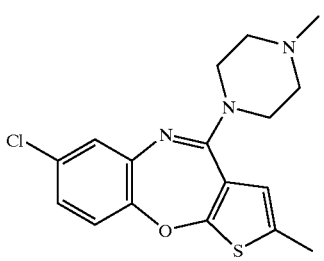

suspended in phosphorus oxychloride (4 ml). N,N-Dimethylaniline (130 mg) was added and the mixture was stirred under reflux with stirring for 4.5 hours. The solvent was completely evaporated azeotropically with toluene under reduced pressure. To the residue was added 1-methylpiperazine (10 ml) and the mixture was stirred under reflux with stirring for 2 hours. The solvent was evaporated under reduced pressure and the residue was purified by silica gel column chromatography (chloroform:methanol=20:1). The obtained compound was converted to fumarate, which was recrystallized from ethyl acetate—methanol to give 7-chloro-2-methyl-4-(4-methylpiperazin-1-yl)thieno[2,3-b][1,5]benzoxazepine fumarate (250 mg).

melting point 227–228° C.

Example 142

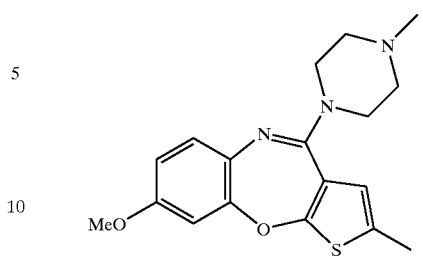

8-Methoxy-2-methylthieno[2,3-b][1,5]benzoxazepin-4(5H)-one (530 mg) was suspended in phosphorus oxychloride (3 ml). N,N-Dimethylaniline (120 mg) was added and the mixture was stirred under reflux with heating for 1.5 hours. The solvent was completely evaporated azeotropically with toluene under reduced pressure, and to the residue was added 1-methylpiperazine (9 ml). The mixture was stirred under reflux with heating for 2 hours. The solvent was evaporated under reduced pressure and the residue was purified by silica gel column chromatography (chloroform:methanol=50:1). The obtained compound was converted to fumarate, which was recrystallized from ethyl acetate-hexane-methanol methanol to give 8-methoxy-2-methyl-4-(4-methylpiperazin-1-yl)thieno[2,3-b][1,5] benzoxazepine fumarate (330 mg).

melting point 219–222° C. decomposition.

Example 143

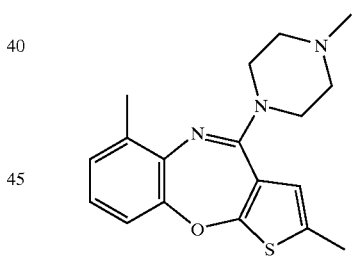

2,6-Dimethylthieno[2,3-b][1,5]benzoxazepin-4(5H)-one (860 mg) was suspended in phosphorus oxychloride (5 ml). N,N-Dimethylaniline (190 mg) was added and the mixture was stirred under reflux with heating for 1.5 hours. The solvent was completely evaporated azeotropically with toluene under reduced pressure, and to the residue was added 1-methylpiperazine (14 ml). The mixture was stirred under reflux with heating for 1.5 hours. The solvent was evaporated under reduced pressure and the residue was purified by silica gel column chromatography (chloroform:methanol= 50:1–20:1). The obtained compound was recrystallized from hexane to give 2,6-dimethyl-4-(4-methylpiperazin-1-yl)thieno[2,3-b][1,5]benzoxazepine (490 mg).

melting point 114–117° C.

Example 144

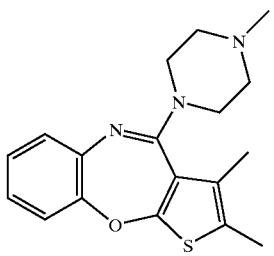

2,3-Dimethylthieno[2,3-b][1,5]benzoxazepin-4(5H)-one (1.4 g) was suspended in phosphorus oxychloride (14 ml). N,N-Dimethylaniline (340 mg) was added and the mixture was stirred under reflux with heating for 2.5 hours. The solvent was completely evaporated azeotropically with toluene under reduced pressure, and to the residue was added 1-methylpiperazine (20 ml). The mixture was stirred under reflux with heating for 1 hour. The reaction system was cooled to room temperature. Ethyl acetate was added, and the mixture was washed with water and saturated brine and dried over sodium sulfate. The solvent was evaporated under reduced pressure and the residue was purified by silica gel column chromatography (chloroform:methanol=9:1). The obtained compound was converted to fumarate, which was recrystallized from ethanol to give 2,3-dimethyl-4-(4-methylpiperazin-1-yl)thieno[2,3-b][1,5]benzoxazepine 1/2 fumarate.

$^1$H-NMR(400 MHz, DMSO-$d_6$) 2.03(3H, s, $CH_3$), 2.21 (3H, s, $CH_3$), 2.26(3H, s, $CH_3$), 2.26(3H, s, $CH_3$), 2.35–3.80 (8H, br, $CH_2$), 6.61(1H, s, fumaric acid), 6.97–7.11(4H, m, ArH)

Example 145

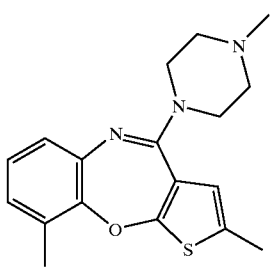

In the same manner as in Example 125 and using 2,9-dimethylthieno[2,3-b][1,5]benzoxazepin-4(5H)-one, phosphorus oxychloride, N,N-dimethylaniline and 1-methylpiperazine, 2,9-dimethyl-4-(4-methylpiperazin-1-yl)thieno[2,3-b][1,5]benzoxazepine is obtained.

Example 146

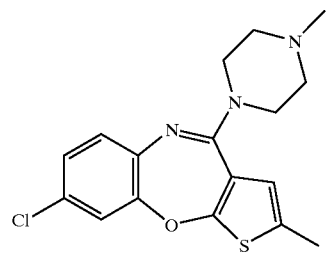

In the same manner as in Example 125 and using 8-chloro-2-methylthieno[2,3-b][1,5]benzoxazepin-4(5H)-one, phosphorus oxychloride, N,N-dimethylaniline and 1-methylpiperazine, 8-chloro-2-methyl-4-(4-methylpiperazin-1-yl)thieno[2,3-b][1,5]benzoxazepine is obtained.

Example 147

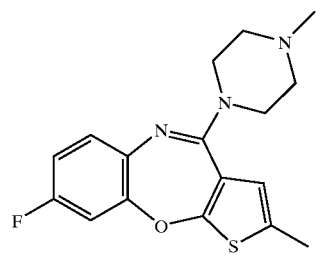

In the same manner as in Example 125 and using 8-fluoro-2-methylthieno[2,3-b][1,5]benzoxazepin-4(5H)-one, phosphorus oxychloride, N,N-dimethylaniline and 1-methylpiperazine, 8-fluoro-2-methyl-4-(4-methylpiperazin-1-yl)thieno[2,3-b][1,5]benzoxazepine is obtained.

Example 148

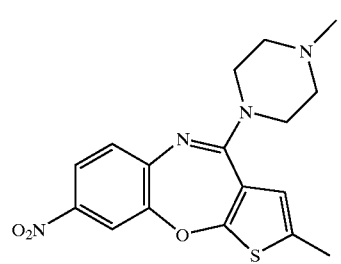

In the same manner as in Example 125 and using 2-methyl-8-nitrothieno[2,3-b][1,5]benzoxazepin-4(5H)-one, phosphorus oxychloride, N,N-dimethylaniline and 1-methylpiperazine, 2-methyl-4-(4-methylpiperazin-1-yl)-8-nitrothieno[2,3-b][1,5]benzoxazepine is obtained.

Example 149

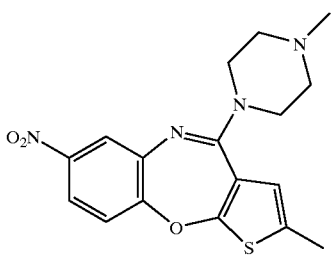

In the same manner as in Example 125 and using 2-methyl-7-nitrothieno[2,3-b][1,5]benzoxazepin-4(5H)-one, phosphorus oxychloride, N,N-dimethylaniline and 1-methylpiperazine, 2-methyl-4-(4-methylpiperazin-1-yl)-7-nitrothieno[2,3-b][1,5]benzoxazepine is obtained.

Example 150

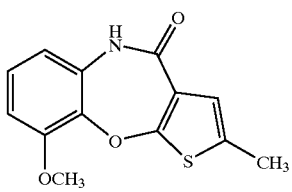

A solution of N-(2-hydroxy-3-methoxyphenyl)-2-bromo-5-methyl-3-thiophenecarboxamide (2.30 g) and sodium methoxide (549 mg) in N,N-dimethylformamide (12 ml) was stirred under reflux with heating for 19 hours. The reaction system was cooled to room temperature, and the reaction mixture was poured into water (50 ml). The mixture was neutralized with hydrochloric acid, extracted twice with chloroform and washed with water. The organic layer was dried over sodium sulfate and the solvent was evaporated under reduced pressure. The residue was purified by silica gel column chromatography (elution solvent hexane:ethyl acetate=1:1) to give 2-methyl-9-methoxythieno[2,3-b][1,5]benzoxazepin-4(5H)-one (1.87 g).

melting point 160–164° C.

$^1$H-NMR(400 MHz, DMSO-$d_6$) δ2.31(3H, s, $CH_3$), 3.81 (3H, s, $CH_3$), 6.71(1H, s, H of thiophene ring), 6.72(1H, d, J=8.3 Hz, ArH), 6.86(1H, d, J=8.3 Hz, ArH), 7.10(1H, dd, J=8.3, 8.3 Hz), 10.09(1H, br.s, NH).

MS:m/e 261.

Example 151

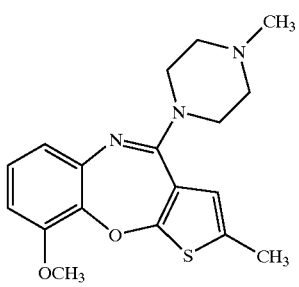

2-Methyl-9-methoxythieno[2,3-b][1,5]benzoxazepin-4(5H)-one (1.58 g) was suspended in phosphorus oxychloride (13 ml). N,N-Dimethylaniline (330 mg) was added and the mixture was stirred under reflux with heating for 2 hours. The solvent was completely evaporated azeotropically with toluene under reduced pressure. To the residue was added 1-methylpiperazine (20 ml) and the mixture was stirred under reflux with heating for 3 hours. The reaction system was cooled to room temperature and the solvent was evaporated under reduced pressure. To the residue was added chloroform and the mixture was washed with water and saturated brine and dried over sodium sulfate. The solvent was evaporated under reduced pressure and the residue was purified by silica gel column chromatography (chloroform:methanol=100:1) to give 2-methyl-9-methoxy-4-(4-methylpiperazin-1-yl)thieno[2,3-b][1,5]benzoxazepine (1.90 g) as a liquid. The obtained liquid (350 mg) and fumaric acid (77 mg) were dissolved in methanol (20 ml) and the solvent was evaporated under reduced pressure. The obtained residue was washed with hot ethyl acetate to give 2-methyl-9-methoxy-4-(4-methylpiperazin-1-yl)thieno[2,3-b][1,5]benzoxazepine fumarate (240 mg).

melting point 239–241° C.

$^1$H-NMR(400 MHz, DMSO-$d_6$) δ2.28(3H, s, $CH_3$), 2.33 (3H, s, $CH_3$), 2.50–4.50(8H, br.s, $CH_2$×4), 3.78(3H, s, $CH_3$), 6.51(1H, s, H of thiophene ring), 6.58(1H, d, J=7.8 Hz, ArH), 6.60(2H, s, fumaric acid), 6.74(1H, d, J=8.3 Hz, ArH), 6.98(1H, dd, J=7.8 Hz, 8.3 Hz, ArH).

MS:m/e 343. Anal. Calcd. for $C_{18}H_{21}N_3O_2S \cdot C_4H_4O_4 \cdot 0.2H_2O$: C, 57.06;H, 5.53; N, 9.07%. Found:C, 57.06;H, 5.51;N, 9.08%.

Example 152

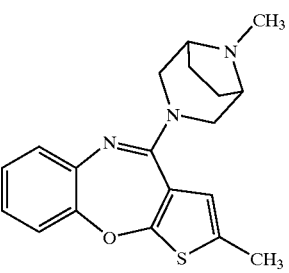

2-Methylthieno[2,3-b][1,5]benzoxazepine-4-one (370 mg) was dissolved in phosphorus oxychloride (7.3 g) and N,N-dimethylaniline (73 mg) was added. The mixture was stirred under reflux with heating for 40 minutes. The phosphorus oxychloride was completely evaporated azeotropically with toluene under reduced pressure. The residue was dissolved in toluene and the mixture was washed twice with saturated aqueous sodium hydrogencarbonate solution. The organic layer was dried over sodium sulfate and the solvent was evaporated under reduced pressure. The residue was dissolved in acetonitrile (10 ml) and thereto were added 8-methyl-3,8-diazabicyclo[3.2.1]octane 2 hydrochloride (240 mg) and diisopropylethylamine (470 mg). The mixture was stirred under reflux with heating for 4.5 hours. 8-Methyl-3,8–3,8-diazabicyclo[3.2.1]octane 2 hydrochloride (240 mg) and diisopropylethylamine (470 mg) were added and 12 hours later, 8-methyl-3,8–3,8-diazabicyclo[3.2.1]octane 2 hydrochloride (240 mg) and diisopropylethylamine (470 mg) were added. The mixture was stirred for 6 hours. The reaction system was allowed to become room temperature and the solvent was evaporated under reduced pressure. The residue was diluted with ethyl acetate and washed three times with water. The organic layer was dried over sodium sulfate and the solvent was evaporated under reduced pressure. The residue was purified by silica gel column chromatography, and the obtained compound was recrystallized from diisopropyl ether to give 2-methyl-4-(8-methyl-3,8-diazabicyclo[3.2.1]octan-3-yl)thieno[2,3-b][1,5]benzoxazepine (300 mg).

melting point: 156–159° C.

¹H-NMR(400 MHz, CDCl₃) δ1.80(2H, m), 2.01(2H, m), 2.33(3H, s), 2.35(3H, s), 3.17(4H, m), 4.00(2H, m), 6.29 (1H, s), 6.95–7.08(4H, m).

Example 153

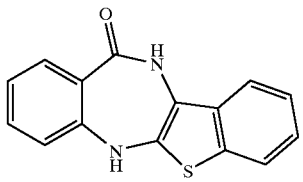

Potassium tert-butoxide (718 mg) was suspended in 1,2-dimethoxyethane (35 ml) and the mixture was refluxed under heating. Thereto was added dropwise ethyl 2-(2-aminoanilino)benzo[b]thiophene-3-carboxylate (1.0 g) dissolved in 1,2-dimethoxyethane (35 ml) over 15 minutes. After 30 minutes, potassium tert-butoxide (359 mg) was added and the mixture was refluxed under heating for 1 hour. After the completion of the reaction, the reaction mixture was allowed to cool to room temperature and poured into 0.5N hydrochloric acid. The mixed solution was extracted 3 times with chloroform, and washed with water and dried over magnesium sulfate. The solution was filtered and the solvent was evaporated under reduced pressure. The precipitated crude crystals were washed with ethyl acetate and diisopropyl ether to give 6H-[1]benzothieno[2,3-b][1,5]benzodiazepin-12(11H)-one (300 mg).

¹H-NMR(400 MHz, CDCl₃) δ7.10–7.18(3H, m), 7.36–7.44(2H, m), 7.51(1H, d, J=8.8 Hz), 7.68(1H, s), 7.88(1H, d=7.8Hz), 7.97(1H, d=7.8 Hz), 11.47(1H, br.s).

Example 154

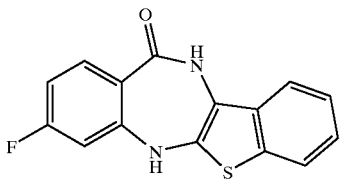

In the same manner as in Example 153 and using potassium tert-butoxide and ethyl 2-(2-aminoanilino)-5-fluorobenzo[b]thiophene-3-carboxylate, 8-fluoro-6H-[1]benzothieno[2,3-b][1,5]benzodiazepin-12(11H)-one was obtained.

melting point:249–250° C. MS:m/e=284.

¹H-NMR(270 MHz, CDCl₃) δ11.54(1H, brs), 7.97–8.00 (1H, m), 7.88–7.92(1H, m), 7.73(1H, s), 7.36–7.47(3H, m), 7.10–7.18(1H, m), 6.96–7.04(1H, m).

Formulation Example 1

Of the compounds of the present invention, a compound (50 mg) of the formula (I) is thoroughly kneaded with lactose (98 mg), corn starch (45 mg) and hydroxypropyl-cellulose (3 mg) in a kneader. The kneaded product is passed through a 200-mesh sieve, dried at 50° C. and passes through a 24-mesh sieve. The product is admixed with talc (3 mg) and magnesium stearate (1 mg) and tablets weighing 200 mg are obtained using a pounder having a diameter of 9 mm. The obtained tablets can be sugar coated or film coated as necessary.

Experimental Example 1

Effects Against MK-801-induced Neurotoxicity

Female SD rats (about 9–12 weeks old) were orally administered with the inventive compounds or vehicle (0.5% hydroxypropylmethylcellulose, 2 ml/kg). One hour later, they were subcutaneously administered with MK-801 (0.5 mg/kg, 1 ml/kg) dissolved in distilled water. Four hours after the MK-801 administration, the rats were anesthetized with pentobarbital and deblooded with saline, which was followed by perfusion/fixing of brain with formalin solution. Their brains were removed quickly after decapitation, and postfixed in the same formalin solution. The brains were embedded in paraffin and cut into coronal sections through posterior cingulate cortex. The brain sections were stained with hematoxylin/eosin (HE). The number of vacuolized cells was counted by light microscopy and calculated in % of the vehicle-treated group.

The inhibitory actions against the MK-801-induced neurotoxicity are to be determined by the potentials to prevent the nerve cell vacuolar reaction by the administration of MK-801, which is expressed as % of the vehicle-treated group. As a result of the test, it was indicated that the compounds of the formula (I) of the present invention suppressed the MK-801-induced neurotoxicity, wherein 50% effective amount to inhibit MK-801-induced neurotoxicity was not more than 10 mg/kg.

Experimental Example 2

Inhibitory Action Against Methamphetamine-induced Hyperactivity

Groups of 15 male ddY mice (20–30 g, 4 weeks old) were used. They were orally administered with the test compounds. One hour later, methamphetamine in saline at 1 mg/kg was subcutaneously administered and the mice were immediately placed in the test box (inside size: 25×15×14 (height) cm) each fitted with a pair of infra-red beams. Interruptions of the infra-red beams were counted over a 30 min period, from 10 to 40 min after the initiation of observation, and were used as an index of methamphetamine-induced hyperactivity. ED₅₀ values of the test compounds to suppress the hyperactivity were calculated. As a result of the test, it was indicated that the compounds of the formula (I) of this invention suppressed methamphetamine-induced hyperactivity, wherein 50% effective amount to suppress methamphetamine-induced hyperactivity was not more than 10 mg/kg.

Experimental Example 3

Clozapine-cued Discrimination Test

Following reduction, by limiting the diet, to 80% of the body weight under free access to diet, the rats were placed in a Skinner box equipped with two levers. Therein, they were trained to consecutively press 10 times either the right or left lever for feed pellet reward reinforcement. Subsequently, they were injected intraperitoneally with clozapine or saline in a random-alternation sequence once (one session) each day, wherein the drug or saline administration was not given for more than 3 consecutive days. When clozapine was administered at 5 mg/kg, one of the levers was paired with the reward and when saline was administered, the other lever was paired with the reward, whereby the rats were made to acquire discrimination ability. After the acquisition of the discrimination ability, the compound of the present invention was administered to confirm generalization against clozapine. As a result of the test, it was indicated that the compounds of the formula (I) of this invention generalized to the clozapine discrimination stimulus.

Experimental Example 4
MK-801-cued Discrimination Test

Following reduction, by limiting the diet, to 80% of the body weight under free access to diet, the rats were placed in a Skinner box equipped with two levers. Therein, they were trained to consecutively press 10 times either the right or left lever for feed pellet reward reinforcement. Subsequently, they were injected intraperitoneally with MK-801 or saline in a random-alternation sequence once (one session) each day, wherein the drug or saline administration was not given for more than 3 consecutive days. When MK-801 was administered at 0.1 mg/kg, one of the levers was paired with the reward and when saline was administered, the other lever was paired with the reward, whereby the rats were made to acquire discrimination ability. After the acquisition of the discrimination ability, the compound of the present invention was administered to confirm antagonism against MK-801 discrimination. As a result of the test, it was indicated that the compounds of the formula (I) of this invention had antagonistic activity against the effect of MK-801 discrimination stimulus.

Experimental Example 5
Anti-apomorphine Action

Groups of 15 male ddY mice (20–30 g, 4 weeks old) were used. They were orally administered with the compounds of the present invention. One hour later, an aqueous solution of apomorphine in ascorbic acid at 0.5 mg/kg was subcutaneously administered and the mice were immediately placed in the test box (inner size: 25×15×14 (height) cm) each fitted with a pair of infra-red beams. Interruptions of the infra-red beams immediately after the initiation of observation to 30 min later were used as an index of apomorphine-induced hyperactivity. The compounds of the formula (I) of this invention suppressed apomorphine-induced hyperactivity, wherein 50% effective amount to suppress apomorphine-induced hyperactivity was not more than 10 mg/kg.

Experimental Example 6
Conditioned Avoidance Response Inhibitory Action

Male Wistar rats (250–400 g, 14–25 weeks old) were placed in the test box (30×30×35 (height) cm) fitted with a pole (diameter 2.5 cm) in its center and grid on the floor and given 5 seconds of sound stimulus (conditioned stimulus) and then 10 seconds of electrical shock (AC 400V, 0.6 mA), thereby forcing them to learn to avoid the electric shock by climbing the pole during the sound stimulus. Each session consisted of 10 sequences of the conditioned stimulus and electric shock at 2-min intervals. The rats (10 per group) capable of stably showing at least 80% on the avoidance response were used for the study of conditioned avoidance response inhibitory action by the compound of the present invention. The conditioned avoidance response at 1, 3, 5 and 24 hours after administration of the compounds of the present invention was determined with the lapse of time and 50% effective amount to inhibit conditioned avoidance response by the compounds of the present invention in each time was determined. As a result of the test, 50% effective amount to inhibit the conditioned avoidance response by the compounds of the formula (I) of this invention was not more than 20 mg/kg.

Experimental Example 7
Catalepsy Induction

Groups of 8 male ddY mice (20–30 g, 4 weeks old) were used for the test. They were administered with the test compounds and the time during which the mice could keep putting their forelimbs over a bar fixed horizontally at 4 cm height with a body posture at an angle of 45° (catalepsy time) was measured up to 30 sec maximum at 1, 3, 5 and 7 hours after the administration. The strength of the catalepsy induction by the test compounds was determined by totalling the time at the four determination points at each dose (sum value) and regressively determining the dose that made the average time 10 sec, based on which $ED_{10S}$ values were calculated. As a result of the test, the $ED_{10S}$ value of the compounds of the formula (I) of this invention was not less than 100 mg/kg.

Experimental Example 8
Analysis of Intermediate in Oxidation by Horseradish Peroxidase A solution (10 μL) of 16 mM inventive compounds in dimethyl sulfoxide, a solution (100 μL) of 5 mM diethylenetriaminepentaacetic acid in phosphate buffer (50 mM, pH 7.4), a solution (100 μL) of 100 mM glutathione in phosphate buffer (50 mM, pH 7.4), 50 mM phosphate buffer (750 μL) and 5,5-dimethyl-1-pyroline N-oxide (1.1 μL) were mixed, and a solution (50 μL) of 0.5 mg/mL horseradish peroxidase in phosphate buffer (50 mM, pH 7.4) was added. The mixture was incubated at 25° C. for 4.5 min. The reaction mixture was subjected to ESR spectroscopy. As a result, it was indicated that the compounds of the formula (I) of this invention did not produce cation radical intermediate during oxidation by horseradish peroxidase.

From the above-mentioned Experimental Examples, it is suggested that the compounds of the formula (I) of the present invention, particularly, the compounds of the formulas (IA) and (IB), showed anti-methamphetamine activity, anti-apomorphine activity, suppression of conditioned avoidance response, suppression of MK-801-induced neurotoxicity, antagonism of MK-801 discrimination and generalization of clozapine discrimination in test animals such as mouse and rats, and are useful as antipsychotics. It is also suggested that they cause less side effects on extrapyramidal system such as catalepsy induction. Furthermore, it was demonstrated that the compounds of the formula (I) of this invention did not produce reaction intermediate corresponding to cation radical intermediate, which is possibly involved in agranulocytosis induced by clozapine, when the reaction intermediate thereof was analyzed using the oxidation by horseradish peroxidase analyzed by ESR spectroscopy as a model reaction of the metabolism of the inventive compounds.

The compounds of the formula (I) of the present invention, particularly, the compounds of the formulas (IA) and (IB), are effective for both the positive symptoms and negative symptoms of schizophrenia, are associated with less side effects such as extrapyramidal motor disorder and the like, are less associated with serious side effects such as agranulocytosis, and are useful as novel antipsychotic agents. These compounds are also useful as therapeutic agents for Alzheimer's disease and manic-depressive illness.

In addition, the compounds of the formulas (IIA) and (IIB) are useful as important synthetic intermediates of the compounds of the formulas (IA) and (IB), respectively.

This application is based on application Nos. 236700/1997, 277771/1997 and 165725/1998 filed in Japan, the contents of which are incorporated hereinto by reference.

What is claimed is:

1. A condensed thiophene compound of formula (IA)

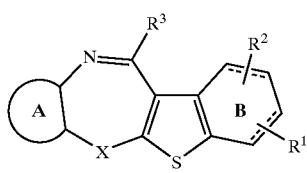
(IA)

wherein

X is O, S, SO or SO$_2$;

R$^1$ and R$^2$ are the same or different and each is hydrogen, alkyl, alkoxy, hydroxyl or halogen;

ring A is a benzene ring having 1 to 4 the same or different substituents thereon selected from the group consisting of alkyl, cycloalkyl, alkoxy, alkoxyalkyl, halogen, alkyl halide, nitro, amino, monoalkylamino, dialkylamino, acylamino, hydroxyl and cyano or a benzene ring without a substituent;

ring B is a benzene ring wherein the bond shown by a dotted line and a solid line is a double bond; and R$^3$ is a group of the formula (1), formula (2), formula (3), formula (26), formula (27), formula (28), formula (29) or formula (30)

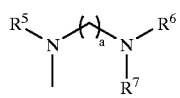
(1)

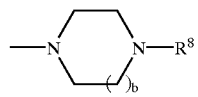
(2)

(3)

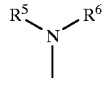
(26)

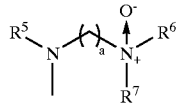
(27)

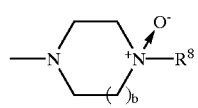
(28)

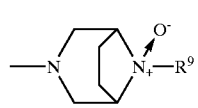
(29)

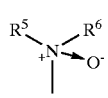
(30)

in the formula (1), formula (26), formula (27) and formula (30), R$^5$, R$^6$ and R$^7$ are the same or different and each is hydrogen, alkyl, cycloalkyl, aryl, heteroaryl, aralkyl, hydroxyalkyl, hydroxyalkoxyalkyl, aminoalkyl, monoalkylaminoalkyl, dialkylaminoalkyl or alkoxyalkyl and a is an integer of 2–4, in the formula (2) and formula (28), R$^8$ is hydrogen, alky, cycloalkyl, aryl, heteroaryl, aralkyl, hydroxyalkyl, hydroxyalkoxyalkyl, aminoalkyl, monoalkylaminoalkyl, dialkylaminoalkyl, acyl, alkoxycarbonyl or alkoxyalkyl, b is 1 or 2, in the formula (3) and formula (29), R$^9$ is hydrogen, alkyl, cycloalkyl, aryl, heteroaryl, aralkyl, hydroxyalkyl, hydroxyalkoxyalkyl, aminoalkyl, monoalkylaminoalkyl, dialkylaminoalkyl, acyl, alkoxycarbonyl or alkoxyalkyl;

or a pharmaceutically acceptable salt thereof or a hydrate thereof.

2. The condensed thiophene compound of claim 1, wherein X is O or S.

3. The condensed thiophene compound of claim 1, wherein R$^1$ and R$^2$ are the same or different and each is hydrogen, halogen, alkoxy or alkyl.

4. The condensed thiophene compound of claim 1, wherein ring A is a benzene ring having 1 to 4 the same or different substituents thereon selected from the group consisting of alkyl, alkoxy, halogen, and alkyl halide, or a benzene ring without a substituent.

5. The condensed thiophene compound of claim 1, wherein R$^3$ is a group of the formula (2) wherein R$^8$ is hydroxyalkoxyalkyl, methyl or ethyl and b is 1.

6. The condensed thiophene compound of claim 1, wherein X is O or S, R$^1$ and R$^2$ are the same or different and each is hydrogen, halogen, alkoxy or alyl, ring A is a benzene ring having 1 to 4 the same or different substituents thereon selected from the group consisting of alkyl, alkoxy, halogen and alkyl halide, or a benzene ring without a substituent, ring B is a benzene ring wherein the bond shown by a dotted line and a solid line is a double bond, and R$^3$ is a group of the formula (2) wherein R$^8$ is hydroxyalkoxyalkyl, methyl or ethyl and b is 1, or a pharmaceutically acceptable salt thereof or a hydrate thereof.

7. A pharmaceutical composition, comprising the condensed thiophene compound of claim 1, a pharmaceutically acceptable salt thereof or a hydrate thereof and a pharmaceutically acceptable additive.

8. A benzothiophene compound of the formula (IIA)

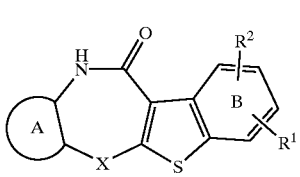
(IIA)

wherein

X is O, S, SO or SO$_2$;

R$^1$ and R$^2$ are the same or different and each is hydrogen, alkyl, alkoxy, hydroxyl or halogen;

ring A is a benzene ring having 1 to 4 the same or different substituents thereon selected from the group consisting of alkyl, cycloalkyl, alkoxy, alkoxyalkyl, halogen, alkyl halide, nitro, amino, monoalkylamino, dialkylamino, acylamino, hydroxyl and cyano or a benzene ring without a substituent; and ring B is a benzene ring wherein the bond shown by a dotted line and a solid line is a double bond.

9. The benzothiophene compound of claim 8, wherein X is O or S.

10. The benzothiophene compound of claim 8, wherein $R^1$ and $R^2$ are the same or different and each is hydrogen, halogen, alkoxy or alkyl.

11. The benzothiophene compound of claim 8, wherein ring A is a benzene ring having 1 to 4 the same or different substituents thereon selected from the group consisting of alkyl, alkoxy, halogen, and alkyl halide, or a benzene ring without a substituent.

12. The benzothiophene compound of claim 8, wherein X is O or S, $R^1$ and $R^2$ are the same or different and each is hydrogen, halogen, alkoxy or alkyl, ring A is a benzene ring having 1 to 4 the same or different substituents thereon selected from the group consisting of alkyl, alkoxy, halogen, hydroxyl and alkyl halide, or a benzene ring without a substituent, and ring B is a benzene ring wherein the bond shown by a dotted line and a solid line is a double bond.

13. The benzothiophene compound of claim 8, which is selected from the group consisting of 1,2,3,4-tetrahydro-[1]benzothieno[2,3-b][1,5]benzoxazepin-12(11H)-one,
1,2,3,4-tetrahydro-8-methyl-[1]benzothieno[2,3-b][1,5]benzoxazepin-12(11H)-one,
8-fluoro-1,2,3,4-tetrahydro-[1]benzothieno[2,3-b][1,5]benzoxazepin-12(11H)-one,
[1]benzothieno[2,3-b][1,5]benzoxazepin-12(11H)-one,
8-methyl-[1]benzothieno[2,3-b][1,5]benzoxazepin-12(11H)-one,
8-fluoro-[1]benzothieno[2,3-b][1,5]benzoxazepin-12(11H)-one,
1,2,3,4-tetrahydro-[1]benzothieno[2,3-b][1,5]benzothiazepin-12(11H)-one,
1,2,3,4-tetrahydro-8-methyl-[1]benzothieno[2,3-b][1,5]benzothiazepin-12(11H)-one,
8-fluoro-1,2,3,4-tetrahydro-[1]benzothieno[2,3-b][1,5]benzothiazepin-12(11H)-one,
[1]benzothieno[2,3-b][1,5]benzothiazepin-12(11H)-one,
8-methyl-[1]benzothieno[2,3-b][1,5]benzothiazepin-12(11H)-one, and
8-fluoro-[1]benzothieno[2,3-b][1,5]benzothiazepin-12(11H)-one.

14. A method for treating a patient suffering from schizophrenia, which comprises administering a therapeutically effective amount of the compound of claim 1 to the patient.

15. A method for treating a patient suffering from Alzheimer's disease, which comprises administering a therapeutically effective amount of the compound of claim 1 to the patient.

16. A method for treating a patient suffering from manic-depressive illness, which comprises administering a therapeutically effective amount of the compound of claim 1 to the patient.

* * * * *

UNITED STATES PATENT AND TRADEMARK OFFICE
CERTIFICATE OF CORRECTION

| | |
|---|---|
| PATENT NO. | : 6,455,521 B1 |
| APPLICATION NO. | : 09/837424 |
| DATED | : September 24, 2002 |
| INVENTOR(S) | : Koji Seio et al. |

It is certified that error appears in the above-identified patent and that said Letters Patent is hereby corrected as shown below:

Item 62 on the cover page of this patent is requested to be amended to read:

Division of application No. 09/341,317, filed on Jul. 8, 1999, now Pat. No. 6,271,225, which is a U.S. national stage of International Application No. PCT/JP98/03915 filed July 8, 1999.

Signed and Sealed this

Twenty-second Day of August, 2006

JON W. DUDAS
*Director of the United States Patent and Trademark Office*